US011771684B2

(12) United States Patent
Romero et al.

(10) Patent No.: US 11,771,684 B2
(45) Date of Patent: Oct. 3, 2023

(54) INHIBITORS OF DIHYDROCERAMIDE DESATURASE FOR TREATING DISEASE

(71) Applicant: Centaurus Therapeutics, Half Moon Bay, CA (US)

(72) Inventors: Donna L. Romero, Half Moon Bay, CA (US); John M. McCall, Half Moon Bay, CA (US); Jeremy Blitzer, Half Moon Bay, CA (US)

(73) Assignee: Centaurus Therapeutics, Half Moon Bay, CA (US)

( * ) Notice: Subject to any disclaimer, the term of this patent is extended or adjusted under 35 U.S.C. 154(b) by 186 days.

(21) Appl. No.: 17/477,953

(22) Filed: Sep. 17, 2021

(65) Prior Publication Data

US 2022/0079926 A1    Mar. 17, 2022

Related U.S. Application Data

(63) Continuation of application No. 16/468,637, filed as application No. PCT/US2017/066172 on Dec. 13, 2017, now Pat. No. 11,135,207.

(60) Provisional application No. 62/433,625, filed on Dec. 13, 2016.

(51) Int. Cl.
| | |
|---|---|
| *A61K 9/00* | (2006.01) |
| *A61K 39/395* | (2006.01) |
| *A61K 31/44* | (2006.01) |
| *A61K 31/167* | (2006.01) |
| *A61K 31/416* | (2006.01) |
| *A61K 31/444* | (2006.01) |
| *A61K 31/496* | (2006.01) |
| *A61P 9/10* | (2006.01) |
| *A61P 3/06* | (2006.01) |
| *A61P 3/10* | (2006.01) |
| *A61P 11/00* | (2006.01) |
| *A61P 35/00* | (2006.01) |
| *C07C 233/65* | (2006.01) |
| *C07D 213/73* | (2006.01) |
| *C07D 231/56* | (2006.01) |
| *C07D 401/12* | (2006.01) |
| *C07D 401/14* | (2006.01) |

(52) U.S. Cl.
CPC ............ *A61K 31/44* (2013.01); *A61K 9/0053* (2013.01); *A61K 31/167* (2013.01); *A61K 31/416* (2013.01); *A61K 31/444* (2013.01); *A61K 31/496* (2013.01); *A61K 39/3955* (2013.01); *A61P 3/06* (2018.01); *A61P 3/10* (2018.01); *A61P 9/10* (2018.01); *A61P 11/00* (2018.01); *A61P 35/00* (2018.01); *C07C 233/65* (2013.01); *C07D 213/73* (2013.01); *C07D 231/56* (2013.01); *C07D 401/12* (2013.01); *C07D 401/14* (2013.01)

(58) Field of Classification Search
CPC .. A61K 9/0053; A61K 39/3955; A61K 31/44; A61K 31/167; A61K 31/416; A61K 31/444; A61K 31/496; A61P 9/10; A61P 3/06; A61P 3/10; A61P 11/00; A61P 35/00; C07C 233/65; C07D 213/73; C07D 231/56; C07D 401/12; C07D 401/14
See application file for complete search history.

(56) References Cited

U.S. PATENT DOCUMENTS

| | | |
|---|---|---|
| 6,258,953 B1 | 7/2001 | Howard et al. |
| 2003/0162789 A1 | 8/2003 | Park et al. |
| 2020/0339535 A1 | 10/2020 | Romero et al. |

FOREIGN PATENT DOCUMENTS

| | | |
|---|---|---|
| WO | 2015196258 | 12/2015 |
| WO | 2018112077 | 6/2018 |

OTHER PUBLICATIONS

Moore, et al., Heterocyclic Studies. VII. The Preparation and Reactions of 2-Amino-5-hydroxypyridines; the Formation of an Azaquinone (1959). (Year: 1959).*
International Application No. PCT/US2017/066172; International Preliminary Report on Patentability, dated Jun. 18, 2019; 6 pages.
International Application No. PCT/US2017/066172; International Search Report and Written Opinion of the International Searching Authority, dated Apr. 12, 2018; 10 pages.
Moore, et al, (1959) Heterocyclic Studies, VII. The Preparation and Reactions of 2-Amino-5-hydroxypyridines; the Formation of an Azaquinone.
Prime, M. et al., "Discovery and Structure-Activity Relationship of Potent and Selective Covalent Inhibitors of Transglutaminase 2 for Huntington's Disease", J Med Chem., 55(3):1021-46, (2012).
PubChem CID 221792, Create dale Mar. 26, 2005 (Mar. 26, 2005) pp. 1-23.

* cited by examiner

*Primary Examiner* — Erich A Leeser
(74) *Attorney, Agent, or Firm* — Bozicevic, Field & Francis LLP; Edward J. Baba; Michael J. Blessent

(57) ABSTRACT

Disclosed herein are dihydroceramide desaturase 1 (Des1) inhibitor compounds and compositions, which are useful in the treatment of diseases, such as metabolic, cardiovascular, fibrotic, autoimmune/chronic inflammatory diseases, cystic fibrosis, various cancers, neurodegenerative diseases, lipid storage disorders, and ischemia/reperfusion injury, where inhibition of Des1 is expected to be therapeutic to a patient. Methods of inhibition of Des1 activity in a human or animal subject are also provided.

42 Claims, No Drawings

INHIBITORS OF DIHYDROCERAMIDE DESATURASE FOR TREATING DISEASE

CROSS REFERENCE TO RELATED APPLICATIONS

This application is a continuation of U.S. application Ser. No. 16/468,637, filed Jun. 11, 2019, which is a U.S. National Stage Entry of International Application US2017/066172, filed Dec. 13, 2017, which claims the benefit of U.S. Provisional Application No. 62/433,625, filed Dec. 13, 2016, the entirety of which applications are hereby incorporated by reference as if written herein in their entirety.

STATEMENT REGARDING FEDERALLY SPONSORED RESEARCH OR DEVELOPMENT

This invention was made with government support under grant number 1R43DK116450-01, awarded by the National Institutes of Health. The government has certain rights in the invention.

The present disclosure relates to new dihydroceramide desaturase (Des) inhibitor compounds and compositions, and their application as pharmaceuticals for the treatment of disease. Methods of inhibition of dihydroceramide desaturase 1 (Des1) and/or Des2 activity in a human or animal subject are also provided for the treatment of metabolic, cardiovascular, fibrotic, autoimmune/chronic inflammatory diseases, cystic fibrosis, various cancers, neurodegenerative diseases, lipid storage disorders, and ischemia/reperfusion injury.

Dihydroceramide desaturases catalyze the formation of ceramide by introducing a 4, 5-trans double bond into the sphinogoid base backbone of dihydroceramide. Studies using cultured cells and isolated muscles revealed that endogenous ceramides and glucosylceramides antagonize insulin-stimulated glucose uptake and anabolism, and thus could mimic the effects of exogenous sphingolipid analogs. Additionally, studies in rodent models of obesity revealed that genetic or pharmacological inhibition of ceramide or glucosylceramide biosynthesis is insulin sensitizing. Therefore, the excessive production of ceramides is now appreciated as an important nutrient metabolite that accumulates in obesity, altering cellular metabolism and promoting apoptosis, and thus giving rise to many of the hallmark events associated with metabolic disease.

There are at least two isoforms of the human dihydroceramide desaturase proteins, Des1 and Des2. Des1 was identified first and is more broadly expressed; therefore most of the published research to date concerns this isoform. The published data suggest inhibitors of ceramide synthesis, i.e., inhibitors of dihydroceramide desaturases (e.g., Des1), may prove efficacious as therapeutics to treat insulin resistance and metabolic disease. Moreover, the published data suggest that inhibitors of dihydroceramide desaturases (e.g., Des1), may also prove efficacious as therapeutics to treat various cancers, cystic fibrosis, fibrotic diseases, cardiovascular disease, autoimmune/chronic inflammatory diseases, neurodegenerative diseases, lipid storage disorders, and ischemia reperfusion injury.

Novel compounds and pharmaceutical compositions, certain of which have been found to inhibit dihydroceramide desaturase have been discovered, together with methods of synthesizing and using the compounds including methods for the treatment of metabolic disorders in a patient by administering the compounds.

DETAILED DESCRIPTION

Accordingly, the inventors herein disclose new compositions and methods for inhibiting dihydroceramide desaturase activity.

Provided is a compound of structural Formula I:

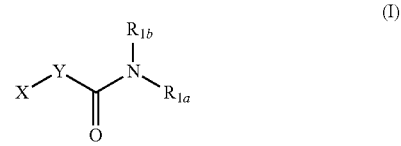

(I)

or a salt thereof, wherein:
$R_{1a}$ and $R_{1b}$ are independently selected from hydrogen, cycloalkylalkyl, aryl, and heteroaryl, and is optionally substituted with 1, 2, or 3 $R_2$ groups, or
$R_{1a}$ and $R_{1b}$, together with the intervening atoms, form a 5-7 membered heterocyclic ring, and is optionally substituted with 1, 2, or 3 $R_2$ groups;
at least one of $R_{1a}$ and $R_{1b}$ is not hydrogen;
X is selected from ethenyl, alkyl, aryl, biaryl, (aryl)cycloalkyl, (aryl)heterocycloalkyl, (aryl)heteroaryl, cycloalkyl, (cycloalkyl)aryl, (cycloalkyl)cycloalkyl, (cycloalkyl)heterocycloalkyl, (cycloalkyl)heteroaryl, heterocycloalkyl, (hetercycloalkyl)aryl, (heterocycloalkyl)cycloalkyl, (heterocycloalkyl)heteroaryl, (heterocycloalkyl)heterocycloalkyl, heteroaryl, (heteroaryl)aryl, (heteroaryl)cycloalkyl, (heteroaryl)heterocycloalkyl, and (heteroaryl)heteroaryl, any of which is optionally substituted with 1, 2, 3, or 4 $R_3$ groups;
Y is selected from a bond, —$CHR_4$—, —$CHR_4CHR_4$—, —$CR_4$=$CR_4$—, and

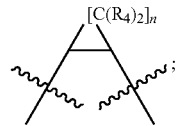

each $R_2$ is independently selected from alkyl, alkoxy, amino, cycloalkyl, heterocycloalkyl, (heterocycloalkyl)alkyl, halogen, hydroxy, S-sulfonamido, and oxo, and is optionally substituted with 1, 2, or 3 $R_5$;
n is selected from 1, 2, 3, 4, and 5;
each $R_3$ is independently selected from alkyl, alkoxy, cyano, haloalkyl, hydroxy, halogen, and oxo; and
each $R_4$ is independently selected from hydrogen, alkyl, alkylamino, halo, and hydroxyl; and
each $R_5$ is independently selected from hydroxy and alkoxy.

Certain compounds disclosed herein possess useful Des inhibiting activity, and may be used in the treatment or prophylaxis of a disease or condition in which Des plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting Des1. Other embodiments provide methods for treating a Des1-mediated disorder in a patient in need of such treatment, comprising administering to said patient a therapeutically effective amount of a compound or composition as disclosed herein. Also provided is the use of certain compounds disclosed herein for use in the manufacture of a medicament for the treatment of a disease or condition ameliorated by the inhibition of Des1.

In certain embodiments, at least one of $R_{1a}$ and $R_{1b}$ is hydrogen.

In certain embodiments, at least one of $R_{1a}$ and $R_{1b}$ is selected from phenyl, pyridinyl, pyridazinyl, pyrimidinyl, pyrazinyl, imidazolyl, quinolinyl, isoquinolinyl, and diazanaphthalenyl.

In embodiments, at least one $R_2$ is hydroxyl.

In certain embodiments, at least one of $R_{1a}$ and $R_{1b}$ is selected from

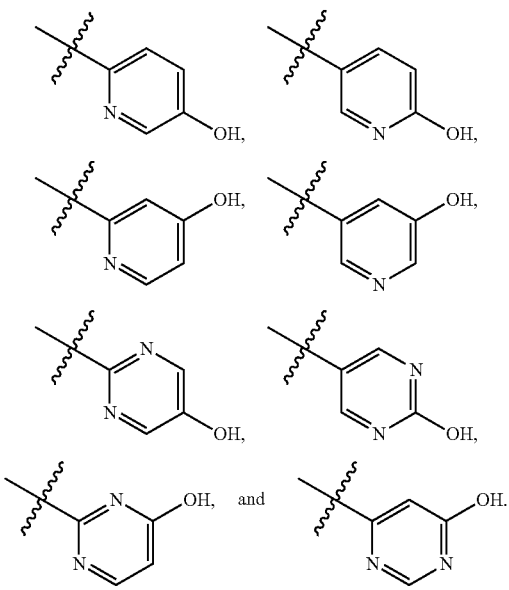

In certain embodiments, at least one of $R_{1a}$ and $R_{1b}$ is selected from phenyl and pyridinyl.

In certain embodiments, at least one of $R_{1a}$ and $R_{1b}$ is

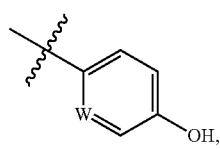

wherein W is selected from CH and N.

In certain embodiments, at least one of $R_{1a}$ and $R_{1b}$ is 5-hydroxypyridin-2-yl.

In certain embodiments, X is selected from phenyl, cycloalkylphenyl, biphenyl, naphthyl, quinolinyl, isoquinolinyl, benzofuranyl, indolyl, indazolyl, and benzotriazolyl, any of which is optionally substituted with 1, 2, 3, or 4 $R_3$ groups.

In certain embodiments, Y is selected from —$CHR_4CHR_4$—, —$CR_4$=$CR_4$—, and

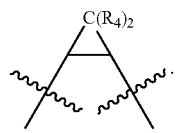

In certain embodiments, Y is a bond.
In certain embodiments, Y is —$CHR_4$—.
In certain embodiments, Y is —$CH_2$—.
In certain embodiments, Y is

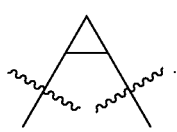 [SMILES: *C1CC1*]

In certain embodiments, $R_4$ is selected from hydrogen and $C_{1-4}$alkyl.

In certain embodiments, $R_4$ is selected from hydrogen and methyl.

In certain embodiments, the compound has structural Formula II:

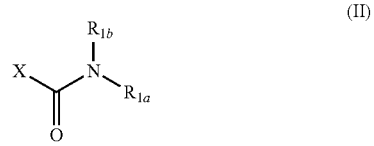

or a salt thereof, wherein:
$R_{1a}$ and $R_{1b}$ are independently selected from hydrogen, aryl, and heteroaryl, and is optionally substituted with 1, 2, or 3 $R_2$ groups, or
$R_{1a}$ and $R_{1b}$, together with the intervening atoms, form a 5-7 membered heterocyclic ring, and is optionally substituted with 1, 2, or 3 $R_2$ groups;
at least one of $R_{1a}$ and $R_{1b}$ is not hydrogen;
X is selected from ethenyl, cycloalkyl, aryl, biaryl, and heteroaryl, any of which may be optionally substituted with 1, 2, 3, or 4 $R_3$ groups;
each $R_2$ is independently selected from alkyl, alkoxy, amino, cycloalkyl, heterocycloalkyl, (heterocycloalkyl)alkyl, halogen, hydroxy, S-sulfonamido, and oxo, and is optionally substituted with 1, 2, or 3 $R_5$;
n is selected from 1, 2, 3, 4, and 5;
each $R_3$ is independently selected from alkyl, alkoxy, halogen, and oxo; and
each $R_5$ is independently selected from hydroxy and alkoxy.

In certain embodiments, the compound has structural Formula III:

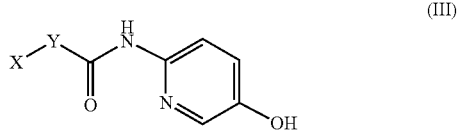

or a salt thereof, wherein:

X is selected from ethenyl, alkyl, aryl, (aryl)cycloalkyl, (aryl)heterocycloalkyl, (aryl)heteroaryl, biaryl, cycloalkyl, (cycloalkyl)aryl, (cycloalkyl)cycloalkyl, (cycloalkyl)heteroaryl, (cycloalkyl)heterocycloalkyl, heteroaryl, (heteroaryl)aryl, (heteroaryl)cycloalkyl, (heteroaryl)heteroaryl, (heteroaryl)heterocycloalkyl, heterocycloalkyl, (hetercycloalkyl)aryl, (heterocycloalkyl)cycloalkyl, (heterocycloalkyl)heteroaryl, (heterocycloalkyl)heterocycloalkyl, any of which is optionally substituted with 1, 2, 3, or 4 $R_3$ groups;

Y is selected from a bond, —$CHR_4CHR_4$—, —$CR_4$=$CR_4$—, and

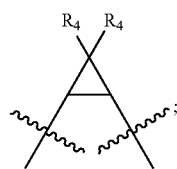

each $R_3$ is independently selected from alkyl, alkoxy, halogen, and oxo; and each $R_4$ is independently selected from hydrogen, alkyl, alkylamino, halo, and hydroxyl.

In certain embodiments, the compound has structural Formula IV:

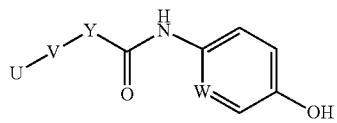

(IV)

or a salt thereof, wherein:

U is selected from aryl, cycloalkyl, heterocycloalkyl, and heteroaryl, any of which is optionally substituted with 1 or 2 $R_3$ groups;

V is selected from a bond, arylene, cycloalkylene, heterocycloalkylene, and heteroarylene, and is optionally substituted with 1 or 2 $R_3$ groups;

W is selected from CH and N;

Y is selected from a bond, —$CHR_4$—, —$CHR_4CHR_4$—, —$CR_4$=$CR_4$—,

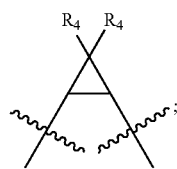

each $R_3$ is independently selected from each $R_3$ is independently selected from alkyl, haloalkyl, hydroxy, alkoxy, haloalkoxy, halogen, cyano, and oxo; and each $R_4$ is independently selected from hydrogen, alkyl, alkylamino, halo, and hydroxyl.

In certain embodiments, Y is selected from a bond, —$CHR_4$—, —$CHR_4CHR_4$—, and —$CR_4$=$CR_4$—.

In certain embodiments, U is selected from aryl, cycloalkyl, heterocycloalkyl, and heteroaryl, and is optionally substituted with 1 or 2 $R_3$ groups.

In certain embodiments, U is selected from phenyl, cyclohexyl, and pyridinyl, and is optionally substituted with 1 or 2 $R_3$ groups.

In certain embodiments, U is selected from phenyl, cyclohexyl, and pyridinyl.

In certain embodiments, V is selected from arylene, cycloalkylene, heterocycloalkylene, and heteroarylene, and is optionally substituted with 1 or 2 $R_3$ groups;

In certain embodiments, V is selected from phenylene, cyclohexylene, piperidinylene, and piperazinylene, and is optionally substituted with 1 or 2 $R_3$ groups.

In certain embodiments, V is selected from

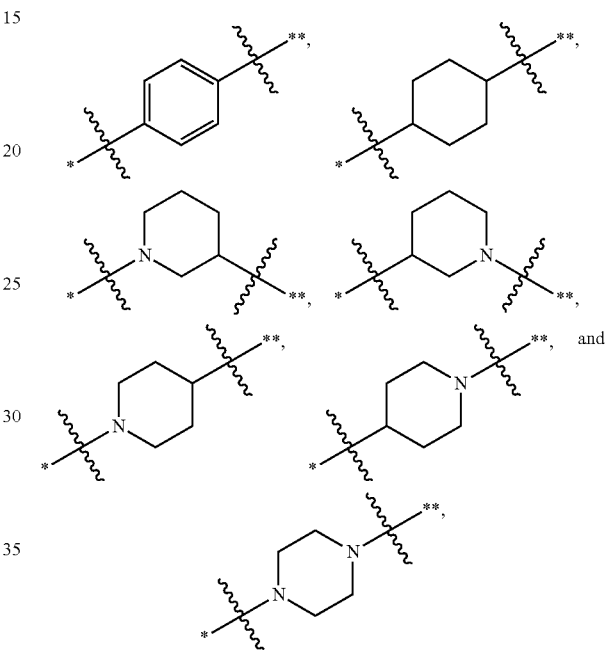

wherein:

* represents the point of attachment to Y; and
** represents the point of attachment to U.

In certain embodiments, W is CH.

In certain embodiments, W is N.

In certain embodiments, Y is selected from a bond and —$CHR_4$—.

In certain embodiments, Y is selected from a bond and —$CH_2$—.

In certain embodiments, each $R_3$ is independently selected from hydroxy, alkoxy, and halogen.

In certain embodiments:
W is N;
U is selected from aryl, cycloalkyl, heterocycloalkyl, and heteroaryl, any of which is substituted with 1 or 2 $R_3$ groups;
V is bond; and each $R_3$ is independently selected from alkyl, haloalkyl, hydroxy, alkoxy, haloalkoxy, halogen, cyano, and oxo.

In certain embodiments, Y is selected from a bond and —$CH_2$—.

In certain embodiments:
U is aryl, and is optionally substituted with 1 or 2 $R_3$ groups; and
each $R_3$ is independently selected from hydroxy, alkoxy, and halogen.

In certain embodiments, the compound has structural Formula V:

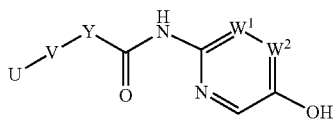
(V)

or a salt thereof, wherein:

U is selected from cycloalkyl, heterocycloalkyl, aryl, and heteroaryl, any of which is optionally substituted with 1 or 2 $R_3$ groups;

V is selected from

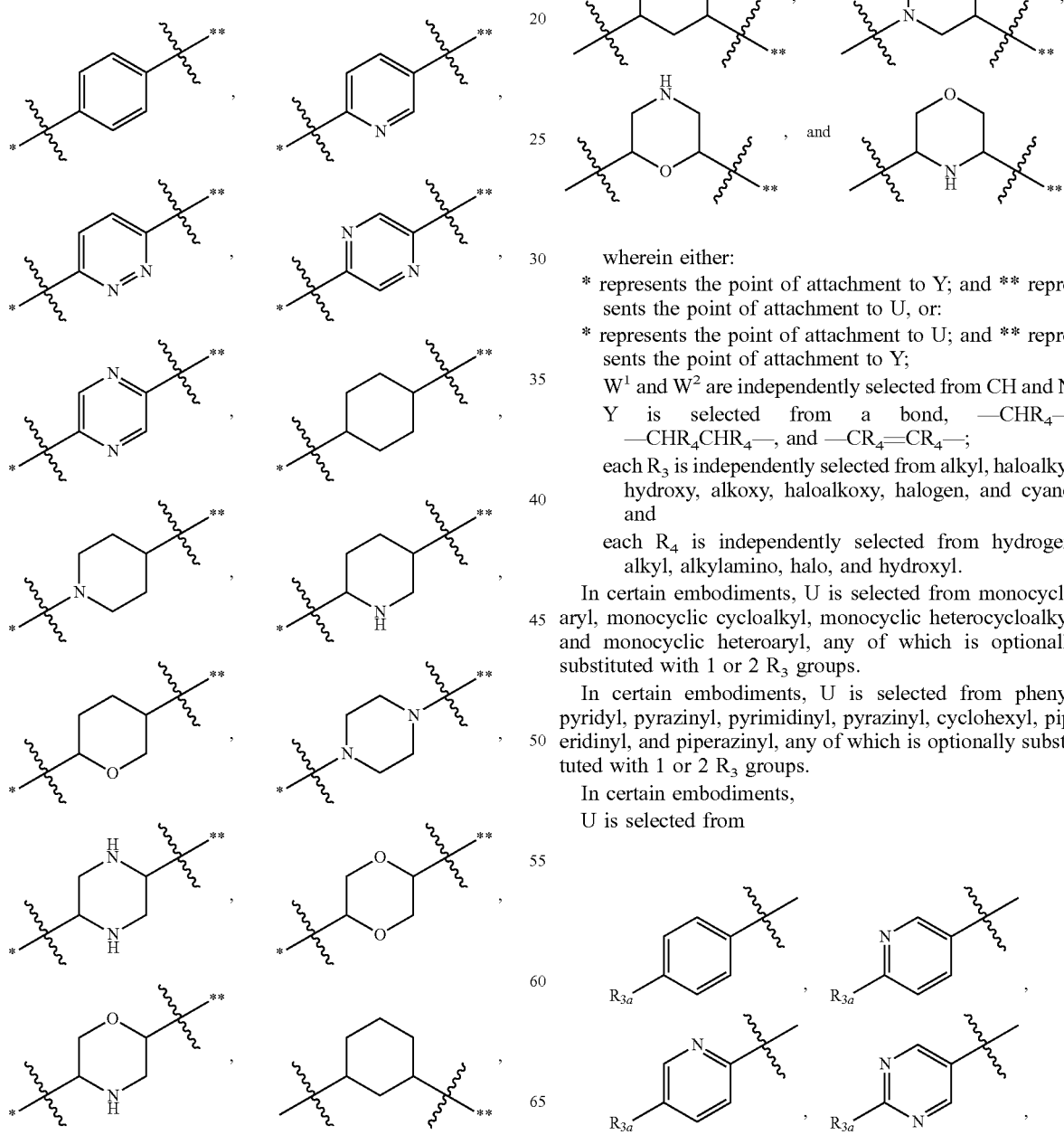

wherein either:
- * represents the point of attachment to Y; and ** represents the point of attachment to U, or:
- * represents the point of attachment to U; and ** represents the point of attachment to Y;

$W^1$ and $W^2$ are independently selected from CH and N;

Y is selected from a bond, —$CHR_4$—, —$CHR_4CHR_4$—, and —$CR_4$=$CR_4$—;

each $R_3$ is independently selected from alkyl, haloalkyl, hydroxy, alkoxy, haloalkoxy, halogen, and cyano; and each $R_4$ is independently selected from hydrogen, alkyl, alkylamino, halo, and hydroxyl.

In certain embodiments, U is selected from monocyclic aryl, monocyclic cycloalkyl, monocyclic heterocycloalkyl, and monocyclic heteroaryl, any of which is optionally substituted with 1 or 2 $R_3$ groups.

In certain embodiments, U is selected from phenyl, pyridyl, pyrazinyl, pyrimidinyl, pyrazinyl, cyclohexyl, piperidinyl, and piperazinyl, any of which is optionally substituted with 1 or 2 $R_3$ groups.

In certain embodiments, U is selected from

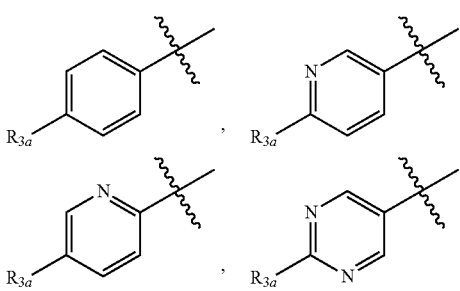

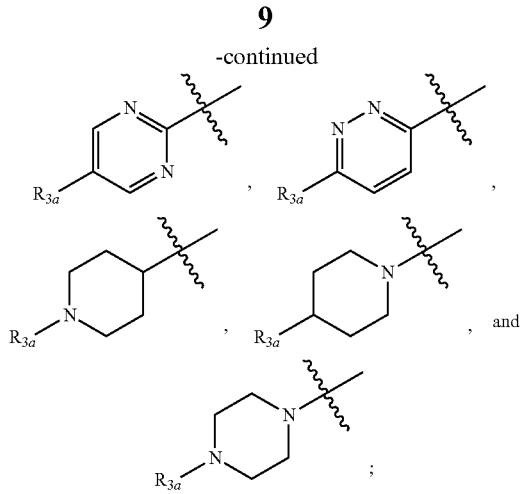

and

R$_{3a}$ is selected from hydrogen, alkyl, haloalkyl, hydroxy, alkoxy, haloalkoxy, halogen, and cyano.

In certain embodiments, the compound has structural Formula VI:

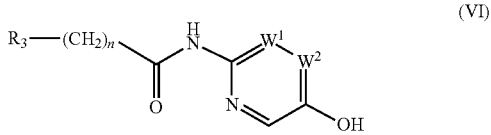

(VI)

or a salt thereof, wherein:

n is selected from 4, 5, 6, 7, 8, 9, and 10;

W$^1$ and W$^2$ are independently selected from CH and N; and

R$_3$ is selected from C$_{2-10}$alkyl, haloalkyl, hydroxy, alkoxy, haloalkoxy, halogen, and cyano.

In certain embodiments, W$^1$ and W$^2$ are CH.

In certain embodiments, R$_3$ is selected from C$_{2-10}$alkyl, hydroxy, C$_{1-4}$alkoxy, and haloalkoxy.

In certain embodiments, R$_3$ is selected from C$_{2-10}$alkyl and C$_{1-4}$alkoxy.

In certain embodiments, the compound has structural Formula VII:

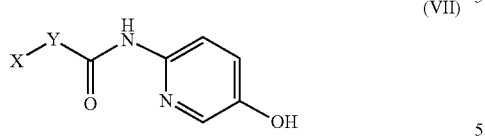

(VII)

or a salt thereof, wherein:

X is selected from

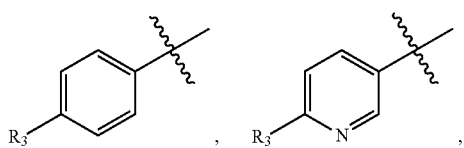

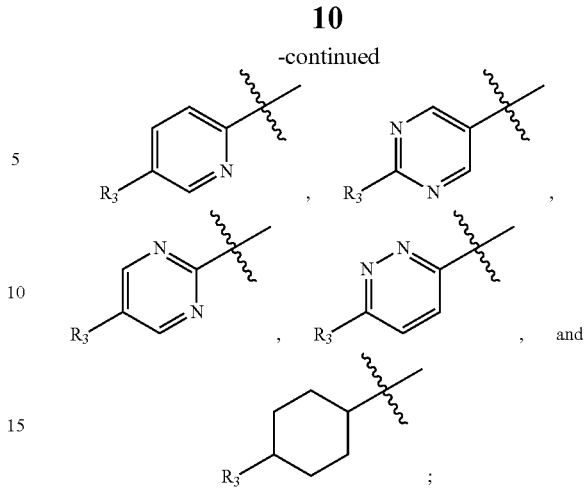

Y is selected from a bond, —CHR$_4$—, —CHR$_4$CHR$_4$—, and —CR$_4$=CR$_4$—;

R$_3$ is selected from alkyl, haloalkyl, hydroxy, alkoxy, haloalkoxy, halogen, cyano, and oxo; and each R$_4$ is independently selected from hydrogen, alkyl, alkylamino, halo, and hydroxyl.

In certain embodiments, Y is a bond.

In certain embodiments, R$_3$ is selected from alkyl, haloalkyl, hydroxy, alkoxy, and haloalkoxy.

Provided is a composition comprising a compound of Formula I and a pharmaceutically acceptable carrier, adjuvant, or vehicle.

Provided is a method of inhibiting Des activity in a biological sample comprising contacting the biological sample with a compound of Formula I.

Provided is a method of treating a Des-mediated disorder in a subject in need thereof, comprising the step of administering to the subject a compound of Formula I.

Provided is a method of treating a Des-mediated disorder in a subject in need thereof, comprising the sequential or co-administration of a compound of Formula I or a pharmaceutically acceptable salt thereof, and another therapeutic agent.

Provided is a compound of any of Formula I for use in human therapy.

Provided is a compound of any of Formula I for use in treating a Des-mediated disease.

Provided is a use of a compound of Formula I for the manufacture of a medicament to treat a Des-mediated disease.

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values that it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include fornyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, the alkyl will comprise from 1 to 10 carbon atoms. In further embodiments, the alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "straight-chain alkyl" refers to an alkyl radical containing from 1 to 20 carbon atoms in a linear sequence without branches. Examples of straight-chain alkyl radicals include n-octyl (—CH$_2$CH$_2$CH$_2$CH$_2$CH$_2$CH$_2$CH$_2$CH$_2$—), n-butyl (—CH$_2$CH$_2$CH$_2$CH$_2$—), and ethyl (—CH$_2$CH$_2$—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl" as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylene," as used herein, alone or in combination, refers to an aryl group attached at two or more positions, such as phenylene (—C$_6$H$_4$—, which encompasses

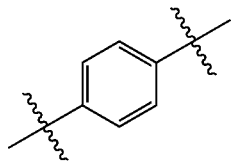 [SMILES: *c1ccc(*)cc1]

and the corresponding meta- and para-isomers). Unless otherwise specified, the term "aryl" may include "arylene" groups.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$=derived from benzene. Examples include benzothiophene and benzimidazole.

The term "biaryl," as used herein, refers to a first aryl group attached to the parent molecular moiety, with the first aryl group substituted with a second aryl group. Examples of biaryl groups include biphenyl, 2-(2-pyridyl)phenyl, and 5-(2-naphthyl)-thien-1-yl.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "cycloalkylene," refers to a cycloalkyl group attached at two or more positions, such as cyclohexylene (—C$_6$H$_{10}$—, which encompasses,

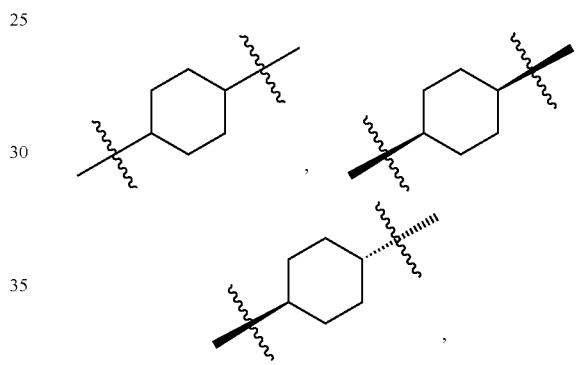

and the corresponding 1,2- and 1,4-isomers). Unless otherwise specified, the term "cycloalkyl" may include "cycloalkylene" groups.

The term "diazanaphthalene," as used herein, alone or in combination, refers to analogues of naphthalene, having formula C$_8$H$_6$N$_2$, in which two >CH groups have been replaced with two >N groups. Examples of diazanaphthalene include cinnoline, phthalazine, and 1,8-diazanaphthalene.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, the heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimnidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The term "heteroarylene," as used herein, alone or in combination, refers to a heteroaryl group attached at two or more positions, such as pyrimidinylene (—C$_5$H$_3$N—, which encompasses the 2,3 isomer:

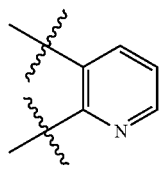 [SMILES: *c1cccnc1*]

as well as the 2,4-, 2,5-, 2,6-, 3,4-, and 3,5-isomers). Unless otherwise specified, the term "heteroaryl" may include "heteroarylene" groups.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each the heteroatom may be independently selected from the group consisting of nitrogen, oxygen, and sulfur In certain embodiments, the hetercycloalkyl will comprise from 1 to 4 heteroatoms as ring members. In further embodiments, the hetercycloalkyl will comprise from 1 to 2 heteroatoms as ring members. In certain embodiments, the hetercycloalkyl will comprise from 3 to 8 ring members in each ring. In further embodiments, the hetercycloalkyl will comprise from 3 to 7 ring members in each ring. In yet further embodiments, the hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "heterocycloalkylene," refers to a heterocycloalkyl group attached at two or more positions, such as piperazinylene (—C$_4$H$_8$N$_2$—). Unless otherwise specified, the term "heterocycloalkyl" may include "heterocycloalkylene" groups.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, alkylcarbonyl, lower carboxyester, lower carboxamido, cyano, hydrogen, halogen, hydroxy, amino, alkylamino, arylamino, amido, nitro, thiol, alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Compounds containing hydroxypyridine groups may contain to varying degrees the pyridone tautomer. Both hydroxypyridine and pyridone tautomeric forms are provided by this disclosure.

Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "Des" means dihydroceramide desaturase, and includes Des1 and Des2 isoforms. Where Des1 modulation by compounds is referenced, it should be understood that unless specifically stated to be selective for Des1, compounds may also modulate other isoforms.

The term Des inhibitor (including Des1 inhibitor) is used herein to refer to a compound that exhibits an $IC_{50}$ with respect to Des activity of no more than about 100 μM and more typically not more than about 50 μM, for example as measured in the Des1 cellular assay described generally herein below. $IC_{50}$ is that concentration of inhibitor that reduces the activity of an enzyme (e.g., Des) to half-maximal level. Certain compounds disclosed herein have been discovered to exhibit inhibition against Des. In certain embodiments, compounds will exhibit an $IC_{50}$ with respect to Des of no more than about 10 μM; in further embodiments, compounds will exhibit an $IC_{50}$ with respect to Des of no more than about 5 M; in yet further embodiments, compounds will exhibit an $IC_{50}$ with respect to Des of not more than about 1 μM; in yet further embodiments, compounds will exhibit an $IC_{50}$ with respect to Des of not more than about 200 nM; in yet further embodiments, compounds will exhibit an $IC_{50}$ with respect to Des of not more than about 100 nM; in yet further embodiments, compounds will exhibit an $IC_{50}$ with respect to Des of not more than about 50 nM; in yet further embodiments, compounds will exhibit an $IC_{50}$ with respect to Des of not more than about 25 nM; in yet further embodiments, compounds will exhibit an $IC_{50}$ with respect to Des of not more than about 10 nM.

The term "fibrosis" describes the development of fibrous connective tissue as a reparative response to injury or damage. When referred to herein as a disease to be treated, fibrosis means the pathological formation/deposition of excess fibrous connective tissue in an organ or tissue, which interferes with normal organ or bodily function.

The term "therapeutically acceptable" refers to those compounds (or salts, prodrugs, tautomers, zwitterionic forms, etc. thereof) which are suitable for use in contact with the tissues of patients without undue toxicity, irritation, and allergic response, are commensurate with a reasonable benefit/risk ratio, and are effective for their intended use.

The phrase "therapeutically effective" is intended to qualify the amount of active ingredients used in the treatment of a disease or disorder or on the effecting of a clinical endpoint.

As used herein, "treating," "treatment," and the like means ameliorating a disease, so as to reduce, ameliorate, or eliminate its cause, its progression, its severity, or one or more of its symptoms, or otherwise beneficially alter the disease in a subject. Reference to "treating," or "treatment" of a patient is intended to include prophylaxis. Treatment may also be preemptive in nature, i.e., it may include prevention of disease in a subject exposed to or at risk for the disease. Prevention of a disease may involve complete protection from disease, for example as in the case of prevention of infection with a pathogen, or may involve prevention of disease progression, for example from prediabetes to diabetes. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

In the present disclosure, the term "radiation" means ionizing radiation comprising particles or photons that have sufficient energy or can produce sufficient energy via nuclear interactions to produce ionization (gain or loss of electrons).

An exemplary and preferred ionizing radiation is an x-radiation. Means for delivering x-radiation to a target tissue or cell are well known in the art. The amount of ionizing radiation needed in a given cell generally depends on the nature of that cell. Means for determining an effective amount of radiation are well known in the art. Used herein, the term "an effective dose" of ionizing radiation means a dose of ionizing radiation that produces an increase in cell damage or death.

The term "radiation therapy" refers to the use of electromagnetic or particulate radiation in the treatment of neoplasia and includes the use of ionizing and non-ionizing radiation.

The term "patient" is generally synonymous with the term "subject" and includes all mammals including humans. Examples of patients include humans, livestock (farm animals) such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Compounds described herein can be administered as follows:

Oral Administration

The compounds of the present invention may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Parenteral Administration

Compounds of the present invention may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions. Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present invention may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Rectal, Buccal, and Sublingual Administration

Suppositories for rectal administration of the compounds of the present invention can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Administration by Inhalation

For administration by inhalation, compounds may be conveniently delivered from an insufflator, nebulizer pressurized packs or other convenient means of delivering an aerosol spray or powder. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the invention may be prepared by any of the well-known techniques of pharmacy, such as effective formulation and administration procedures. Preferred unit dosage formulations are those containing an effective dose, as herein recited, or an appropriate fraction thereof, of the active ingredient. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks.

Methods of Treatment

The present disclosure provides compounds and pharmaceutical compositions that inhibit Des activity and are thus useful in the treatment or prevention of disorders associated with Des. Compounds and pharmaceutical compositions of the present disclosure inhibit Des and are thus useful in the treatment or prevention of a range of disorders associated with Des1.

Metabolic Disorders

In some embodiments, the compounds and pharmaceutical compositions of the present disclosure are useful in the treatment or prevention of metabolic disorders.

In some embodiments, the metabolic disorder is chosen from metabolic syndrome, diabetes, dyslipidemia, hypertriglyceridemia, hypercholesterolemia, fatty liver disease, non-alcoholic steatohepatitis, obesity, and insulin resistance.

In some embodiments, the compounds and pharmaceutical compositions of the present disclosure are useful in the treatment or prevention of lipid storage disorders. In some embodiments, the lipid storage disorder is chosen from Farber's disease, Niemann-Pick disease, Fabry disease, Krabbe disease, Gaucher disease, Tay-Sachs disease, and Metachromatic leukodystrophy.

In some embodiments, the compounds and pharmaceutical compositions may demonstrate efficacy towards a condition chosen from dyslipidemia, type II diabetes, atherosclerosis, obesity, cardiovascular diseases, and liver disease.

In some embodiments, the compounds and pharmaceutical compositions may demonstrate efficacy towards a liver disease chosen from NASH and NAFLD.

In some embodiments, the compounds and pharmaceutical compositions may demonstrate efficacy towards insulin resistance.

In some embodiments, the compounds and pharmaceutical compositions may demonstrate efficacy towards hyperglycemia.

Cardiovascular Disorders

In some embodiments, the compounds and pharmaceutical compositions of the present disclosure may be useful in the treatment or prevention of atherosclerosis, including coronary artery disease and peripheral vascular disease, hypertension, and cardiomyopathy.

In some embodiments, the compounds and pharmaceutical compositions may be useful in the treatment of atherosclerosis.

Cystic Fibrosis

In some embodiments, the compounds and pharmaceutical compositions of the present disclosure may be useful in the treatment or prevention of cystic fibrosis. Various studies have demonstrated that sphingolipids, particularly ceramide, accumulate in the lungs of humans with cystic fibrosis, as well as the corresponding mouse models of cystic fibrosis, including the mice with genetic ablation of the cystic fibrosis transmembrane conductance regulator. This accumulation has been shown to cause inflammation, increased susceptibility to bacterial infections (Grassme et al. 2013 Ceramide in cystic fibrosis. Handb. Exp. Pharmacol. 216, 265-274), as well as lung fibrosis (Ziobro et al. 2013 Ceramide mediates lung fibrosis in cystic fibrosis. Biochem. Biophys. Res. Commun. 434, 705-709).

In some embodiments, the compounds and pharmaceutical compositions of the present disclosure are useful in the treatment or prevention of autoimmune diseases or disorders of inflammation, including acute and chronic inflammatory diseases.

Inflammatory conditions include, without limitation: arthritis, including sub-types and related conditions such as rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis; osteoporosis, tendonitis, bursitis, and other related bone and joint disorders; gastrointestinal conditions such as reflux esophagitis, diarrhea, inflammatory bowel disease, Crohn's disease, gastritis, irritable bowel syndrome, ulcerative colitis, acute and chronic inflammation of the pancreas; pulmonary inflammation, such as that associated with viral infections and cystic fibrosis; skin-related conditions such as psoriasis, eczema, burns, sunburn, dermatitis (such as contact dermatitis, atopic dermatitis, and allergic dermatitis), and hives; pancreatitis, hepatitis, pruritis and vitiligo. In addition, compounds of invention are also useful in organ transplant patients either alone or in combination with conventional immunomodulators. Autoimmune disorders are often classified as inflammatory disorders, as well.

Autoimmune disorders include Crohn's disease, ulcerative colitis, dermatitis, dermatomyositis, diabetes mellitus type 1, Goodpasture's syndrome, Graves' disease, Guillain-Barré syndrome (GBS), autoimmune encephalomyelitis (AE), Hashimoto's disease, idiopathic thrombocytopenic purpura, lupus erythematosus, mixed connective tissue disease, multiple sclerosis (MS), myasthenia gravis, narcolepsy, pemphigus vulgaris, pernicious anemia, psoriasis, psoriatic arthritis, polymyositis, primary biliary cirrhosis, rheumatoid arthritis (RA), Sjögren's syndrome, scleroderma, temporal arteritis (also known as "giant cell arteritis"), vasculitis, and Wegener's granulomatosis.

In some embodiments, the autoimmune disease or chronic inflammatory disease is chosen from arthritis, multiple sclerosis, psoriasis, Crohn's disease, inflammatory bowel disease, lupus, Grave's disease and Hashimoto's thyroiditis, ankylosing spondylitis, and cystic fibrosis.

In certain embodiments, the compounds and pharmaceutical compositions of the present disclosure may have synergistic activity against multiple sclerosis upon coadministration with a therapeutic chosen from fingolimod, a sphingosine-1-phosphate receptor modulator, teriflunomide, dimethyl fumarate, a PAD4 inhibitor, an anti-CD20 mAb, an anti-CD52 mAb, natalizumab, glatiramer acetate, and interferon-β.

In some embodiments, the autoimmune disease inflammatory disease is autoimmune arthritis.

In some embodiments, the autoimmune disease inflammatory disease is rheumatoid arthritis.

In certain embodiments, the compounds and pharmaceutical compositions of the present disclosure may have synergistic activity against arthritis upon coadministration with a therapeutic chosen from analgesics (including traditional NSAIDs and COX2-selective inhibitors), steroids, methotrexate, gold salts, hydroxychloroquine, PAD4 inhibitors, sulfasalazine, leflunomide, anti-TNFα, inhibitors of janus kinases, abatacept, rituximab, and anakinra.

In some embodiments, the compounds and pharmaceutical compositions of the present disclosure can be useful in the treatment or prevention of cardiovascular disease. In some embodiments, the cardiovascular disease is chosen from atherosclerosis, hypertension, and cardiomyopathy.

In some embodiments, the compounds and pharmaceutical compositions of the present disclosure can be useful in the treatment or prevention of ischemia/reperfusion injury. In some embodiments, ischemia/reperfusion injury occurs in organ transplantation, acute kidney injury, cardiopulmonary bypass, pulmonary hypertension, sickle cell disease, myocardial infarction, stroke, surgical resections and reconstructive surgery, reattachment of an appendage or other body part, skin grafting, or trauma.

Proliferative Disorders, e.g. Cancers

In some embodiments, the compounds and pharmaceutical compositions of the present disclosure can be useful in the treatment or prevention of cancer.

In some embodiments, the cancer is chosen from a leukemia, a lymphoma, ovarian cancer, breast cancer, endometrial cancer, colon cancer (colorectal cancer), rectal cancer, bladder cancer, lung cancer (non-small cell lung cancer, adenocarcinoma of the lung, squamous cell carcinoma of the lung), bronchial cancer, bone cancer, prostate cancer, pancreatic cancer, gastric cancer, hepatocellular carcinoma, gall bladder cancer, bile duct cancer, esophageal cancer, renal cell carcinoma, thyroid cancer, squamous cell carcinoma of the head and neck (head and neck cancer), testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, medulloblastoma, astrocytoma, glioma, meningioma, gastrinoma, neuroblastoma, melanoma, myelodysplastic syndrome, and a sarcoma.

In certain embodiments, the compounds and pharmaceutical compositions of the present disclosure are effective against tumor growth, angiogenesis, and chemoresistance, and potentially can facilitate tumor killing either by direct cytotoxicity (including induction of apoptosis) or indirectly by enhancing the immune system's ability to kill the tumor.

In certain embodiments, the compounds and pharmaceutical compositions of the present disclosure may have synergistic activity against cancer upon coadministration with immune check-point inhibitors.

In certain embodiments, the compounds and pharmaceutical compositions of the present disclosure may have synergistic activity against cancer upon coadministration with monoclonal antibodies directed at a target chosen from PD1, PD-L1, CTLA-4, CD47, and OX40.

In certain embodiments, the compounds and pharmaceutical compositions of the present disclosure may have synergistic activity against cancer upon coadministration with small molecules directed at a target chosen from indoleamine-2,3-dioxygenase 1 and arginase-1.

In some embodiments, the compounds and pharmaceutical compositions of the present disclosure can be useful in the treatment or prevention of fibrosis and related diseases. Fibrosis is a pathologic condition involving excessive extracellular matrix production of connective tissue. Consequences can include tissue dysfunction and organ failure.

In some embodiments, the fibrosis affects a site chosen from lungs, kidney, liver, heart, skin, and connective tissues.

In some embodiments, the fibrosis can be: of the lungs, for example pulmonary fibrosis or cystic fibrosis; of the liver, for example cirrhosis; of the heart, for example atrial fibrosis, endomyocardial fibrosis, or fibrosis resulting from myocardial infarction; of the brain, for example a glial scar; kidney fibrosis, such as resulting from diabetic nephropathy; gall bladder fibrosis, skin or dermal fibrosis, such as scleroderma, hypertrophic scarring and keloids; bone marrow fibrosis such as in myelofibrosis; intestinal fibrosis, such as Crohn's disease; or from some other wound, in which case it may be referred to as scarring. The fibrosis may also be chosen from arthrofibrosis, Dupuytren's contracture, mediastinal fibrosis, myelofibrosis, Peyronie's disease, nephrogenic systemic fibrosis, progressive massive fibrosis, a complication of coal workers' pneumoconiosis, retroperitoneal fibrosis, scleroderma, systemic sclerosis, and adhesive capsulitis, and abdominal adhesions secondary to abdominal surgery.

In some embodiments, the compounds and pharmaceutical compositions of the present disclosure may be used to prevent, treat or ameliorate heart attack.

In some embodiments, the compounds and pharmaceutical compositions of the present disclosure may be used to prevent, treat or ameliorate a neurodegenerative disease. Elevated ceramide levels are often found associated with various neurodegenerative diseases.

In some embodiments, the neurodegenerative disease is chosen from Alzheimer's disease, vascular dementia, Parkinson's disease, Huntington's disease, amyotrophic lateral sclerosis, Lewy Body disease, spinal muscular atrophy, Friedrich's ataxia, and spinocerebellar ataxia.

In certain embodiments, the compounds and pharmaceutical compositions of the present disclosure may have synergistic activity against a neurodegenerative disease upon coadministration with a therapeutic agent chosen from cholinesterase inhibitors and memantine.

In certain embodiments, the compounds and pharmaceutical compositions of the present disclosure may have synergistic activity against ALS upon coadministration with a second therapeutic agent for ALS. In certain embodiments, the second therapeutic agent for ALS is chosen from riluzole and edavarone.

Combinations and Combination Therapy

The compounds of the present invention can be used, alone or in combination with other pharmaceutically active compounds, to treat conditions such as those previously described hereinabove. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-metabolic disorder drugs, including metformin, inhibitors of HMG-CoA reductase, inhibitors of sodium/glucose co-transporters, fibrates, omega-3 fatty acids, glucagon-like peptide-1 analogs, and agonists of the glucagon-like peptide-1 receptor, FXR agonists, LXR ligands, PPAR agonists, FGF19 analogs, FGF21 analogs, inhibitors of acetyl CoA carboxylase, inhibitors of stearoyl CoA desaturase-1, CCR2/CCR5 antagonists, and inhibitors of ASK1.

Additional non-limiting examples of possible combination therapies include use of a compound as disclosed herein, and at least one other agent selected from the group comprising: a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidinedione derivative (glitazone) such as pioglitazone or rosiglitazone; and a non-glitazone type PPAR delta agonist e.g. GI-262570; b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin; c) an anti-obesity agent or appetite regulating agent such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine or cannabinoid receptor antagonists; d) anti-hypertensive agents, e.g., loop diuretics such as ethacrynic acid, furosemide and torsemide; diuretics such as thiazide derivatives, chlorothiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutral endopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin n antagonists such as candesartan, eprosartan, irbesartan, losartan, tehnisartan and valsartan, in particular valsartan; renin inhibitors such as aliskiren, terlakiren, ditekiren, RO 66-1132, RO-66-1168; quadrature.-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors; e) an HDL increasing compound; f) cholesterol absorption modulator such as ezetimibe and KT6-971;

g) Apo-A1 analogues and mimetics; h) thrombin inhibitors such as Ximelagatran; aldosterone inhibitors such as anastrazole, fadrazole, and eplerenone; inhibitors of platelet aggregation such as aspirin, and clopidogrel bisulfate.

In another embodiment, the one or more additional pharmaceutically active compounds is selected from the group consisting of anti-cancer drugs, including chemotherapeutics: thiotepa and cyclophosphamide; alkyl sulfonates such as busulfan, improsulfan and piposulfan; aziridines such as benzodepa, carboquone, meturedopa, and uredopa; ethylenimines and methylamelamines including altretamine, triethylenemelamine, triethylenephosphoramide, triethylenethiophosphoramide and trimethylol melamine; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; desosamine; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; cytosine arabinoside (Ara-C); cyclophosphamide; thiotepa; taxoids, e.g., paclitaxel and docetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including both selective estrogen receptor modulators and selective estrogen receptor degraders), including for example tamoxifen, raloxifene, aromatase-inhibiting 4(5)-imidazoles, 4-hydroxytamoxifen, trioxifene, keoxifene, onapristone, toremifene, and fulvestrant; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Chemotherapeutic agents also include signal transduction inhibitors (STI). The term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol and palbociclib); and (vi) phosphatidyl inositol kinase inhibitors.

Chemotherapeutic agents also include various immune-modulating agents, including checkpoint inhibitors (e.g. anti-PD1, anti-PDL1, anti-CTLA4, anti-OX40, and anti-CD47 monoclonal antibodies), IDO1 inhibitors, arginase-1 inhibitors, inhibitors of regulatory T cells, and inhibitors of myeloid-derived suppressor cells.

In another embodiment, the one or more additional pharmaceutically active compounds is selected from the group consisting of disease modifying anti-rheumatic drugs (DMARDs), including steroids, methotrexate, sulfasalazine, as well as anti-TNF, anti-IL1, anti-IL6, and Janus kinase inhibitors.

In another embodiment, the one or more additional pharmaceutically active compounds is selected from the group consisting of multiple sclerosis drugs, including interferon-beta1a, interferon-beta1b, glatiramer acetate, mitoxantrone, fingolimod, teriflunomide, dimethyl fumarate, anti-alpha4 integrin monoclonal antibody, anti-CD52 monoclonal antibody, anti-CD25 monoclonal antibody, and anti-CD20 monoclonal antibody.

In another embodiment, the one or more additional pharmaceutically active compounds is selected from the group consisting enzyme replacement therapies. Enzyme replacement therapy may, for example, include recombinant human acid ceramidase.

In another embodiment, the one or more additional pharmaceutically active compounds is selected from the group consisting of pancreatic enzyme supplements, multivitamins, mucolytics, antibiotics, bronchodilators, anti-inflammatory agents, insulin, bisphosphonates, ivacaftor, and lumacaftor/ivacaftor.

In another embodiment, the one or more additional pharmaceutically active compounds is selected from the group consisting of donepezil, galantamine, rivastigmine, memantine, riluzole, levodopa/carbidopa, pramipexole, ropinirole, rotigotine, apomorphine, selegiline, rasagiline, entacapone, tolcapone, benzotropine, trihexyphenidyl, amantadine, tetrabenazine, haloperidol, risperidone, quetiapine, levetiracetam, clonazepam, edaravone.

Des inhibitor compounds and compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer a Des1 inhibitor compound, as described herein, in combination with another therapeutic agent. By way of example only, the therapeutic effectiveness of a Des1 inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a Des inhibitor as described herein) may be administered in any order, or simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses.

If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time between the multiple administration steps ranges from a few minutes to several hours, depending upon the properties of each pharmaceutical agent, such as potency, solubility, bioavailability, plasma half-life and kinetic profile of the pharmaceutical agent.

In another embodiment, a Des inhibitor is optionally used in combination with procedures that provide additional benefit to the patient. A Des inhibitor and any additional therapies are optionally administered before, during or after the occurrence of a disease or condition, and the timing of administering the composition containing a Des inhibitor varies in some embodiments. Thus, for example, a Des inhibitor is used as a prophylactic and is administered continuously to subjects with a propensity to develop conditions or diseases in order to prevent the occurrence of the disease or condition. A Des inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

Compound Synthesis

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art.

LIST OF ABBREVIATIONS

Ac$_2$O=acetic anhydride; AcCl=acetyl chloride; AcOH=acetic acid; AIBN=azobisisobutyronitrile; aq.=aqueous; Bu$_3$SnH=tributyltin hydride; CD$_3$OD=deuterated methanol; CDCl$_3$=deuterated chloroform; CDI=1,1'-Carbonyldiimidazole; DBU=1,8-diazabicyclo[5.4.0]undec-7-ene; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-d$_6$=deuterated dimethyl sulfoxide; DMSO=dimethyl sulfoxide; DPPA=diphenylphosphoryl azide; EDC.HCl=EDCI.HCl=1-ethyl-3-(3-dimethylaminopropyl)carbodiimide hydrochloride; Et$_2$O=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; i-PrOH=isopropanol; LAH=lithium aluminium hydride; LiHMDS=Lithium bis(trimethylsilyl)amide; MeCN=acetonitrile; MeOH=methanol; MP-carbonate resin=macroporous triethylammonium methylpolystyrene carbonate resin; MsCl=mesyl chloride; MTBE=methyl tertiary butyl ether; MW=microwave irradiation; n-BuLi=n-butyllithium; NaHMDS=Sodium bis(trimethylsilyl)amide; NaOMe=sodium methoxide; NaOtBu=sodium t-butoxide; NBS=N-bromosuccinimide; NCS=N-chlorosuccinimide; NMP=N-Methyl-2-pyrrolidone; Pd(Ph$_3$)$_4$=tetrakis(triphenylphosphine)palladium(0); Pd$_2$(dba)$_3$=tris(dibenzylideneacetone)dipalladium(0); PdCl$_2$(PPh$_3$)$_2$=bis(triphenylphosphine)palladium(II) dichloride; PG=protecting group; prep-HPLC=preparative high-performance liquid chromatography; PyBop=(benzotriazol-1-yloxy)-tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; t-BuOH=tert-butanol; T3P=Propylphosphonic Anhydride; TBS=tert-butyldimethylsilyl; TBSCl=tert-butyldimethylchlorosilane; TEA=Et$_3$N=triethylamine; TFA=trifluoroacetic acid; TFAA=trifluoroacetic anhydride; THF=tetrahydrofuran; Tol=toluene; TsCl=tosyl chloride; XPhos=2-dicyclohexylphosphino-2',4',6'-triisopropylbiphenyl.

General Synthetic Methods for Preparing Compounds

The following schemes can generally be used to practice the present invention.

Scheme I

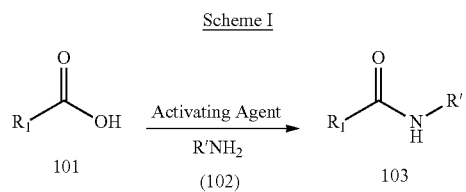

Scheme I describes coupling of an organic acid with an amine. Carboxylic acid 101 is dissolved in an appropriate solvent (e.g. THF or methylene chloride) and treated with an activating agent (e.g. carbonyl diimidazole) at temperatures between 0° C. and room temperature. In certain cases, amine 102 is present in the reaction mixture at essentially the same time. In certain cases, amine 102 is added after a period of time. The reactions are stirred until coupling is complete (30 minutes to 8 hours) to produce amide 103. The reaction mixtures are concentrated and then partitioned between methylene chloride and aqueous sodium bicarbonate. The

Scheme II

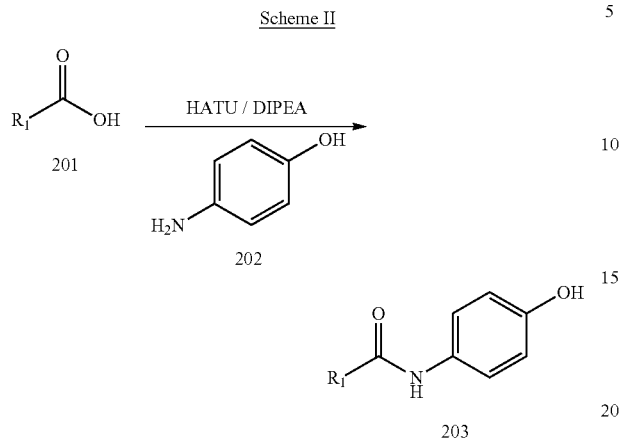

Scheme II can be employed to form N-(4-hydroxyphenyl) amides. A mixture of 4-aminophenol (202, 1.0 mmol), DIPEA (2 mmol), HATU (1.5 mmol) and acid (201, 1.0 mmol) in N,N-dimethylformamide (5 mL) was stirred for 16 hours at ambient temperature. The mixture was concentrated and the residue was purified by Prep-HPLC with the following condition: Column: XBridge Prep OBD C18 Column 30×150 mm 5 um; Mobile Phase A:Water (0.1% FA), Mobile Phase B: ACN; Flow rate: 60 mL/min; Gradient: 10% B to 45% B in 7 min; 254/220 nm, to afford amide 203.

Scheme III

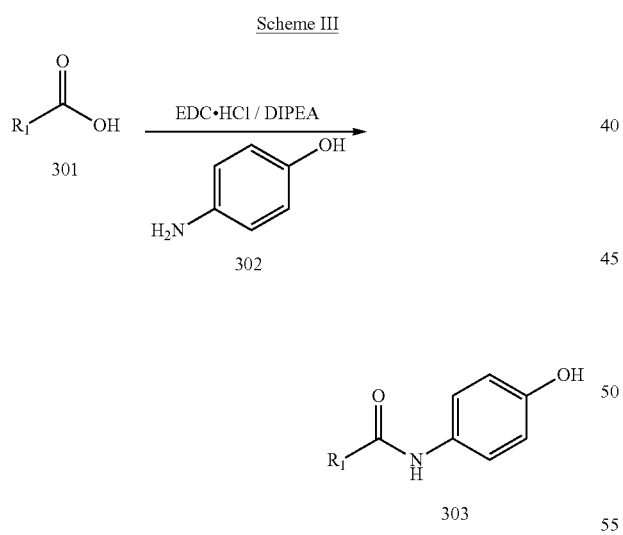

Scheme III can be employed to form N-(4-hydroxyphenyl)amides. A mixture of 4-aminophenol (302, 1.0 mmol), DMAP (2.0 mmol), EDC.HCl (2.0 mmol) and acid (301, 1.0 mmol) in DCM (5 mL) was stirred for 16 hours at ambient temperature. The mixture was concentrated and the residue was purified by Prep-HPLC with the following condition: Column: XBridge Prep OBD C18 Column 30×150 mm 5 um; Mobile Phase A:Water (0.1% FA), Mobile Phase B: ACN; Flow rate: 60 mL/min; Gradient: 10% B to 45% B in 7 min; 254/220 nm, to afford amide 303.

Scheme IV

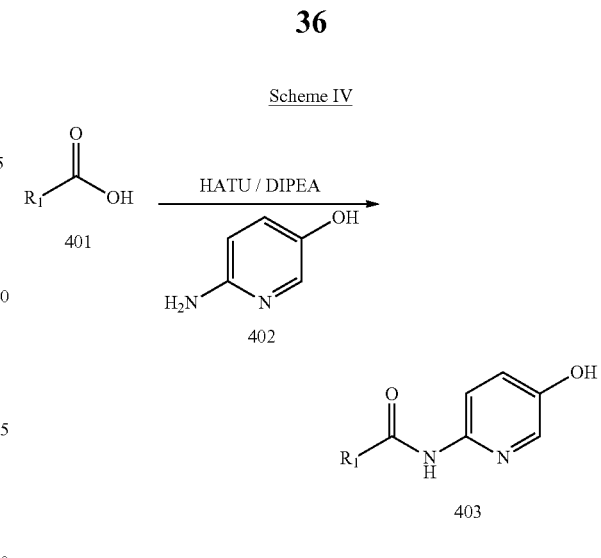

Scheme IV can be employed to form N-(5-hydroxypyridin-2-yl)amides. A mixture of 6-aminopyridin-3-ol (402, 1.0 mmol), DIPEA (2 mmol), HATU (1.5 mmol) and acid 401 (1.0 mmol) in N,N-dimethylformamide (5 mL) was stirred for 16 hours at ambient temperature. The mixture was concentrated and the residue was purified by Prep-HPLC with the following condition: Column: SunFire Prep C18 OBD Column 19×150 mm 5 um 10 nm; Mobile Phase A:Water (0.1% FA), Mobile Phase B: ACN; Flow rate: 17 mL/min; Gradient: 19% B to 23% B in 8 min; 254 nm, to afford amide 403.

Scheme V

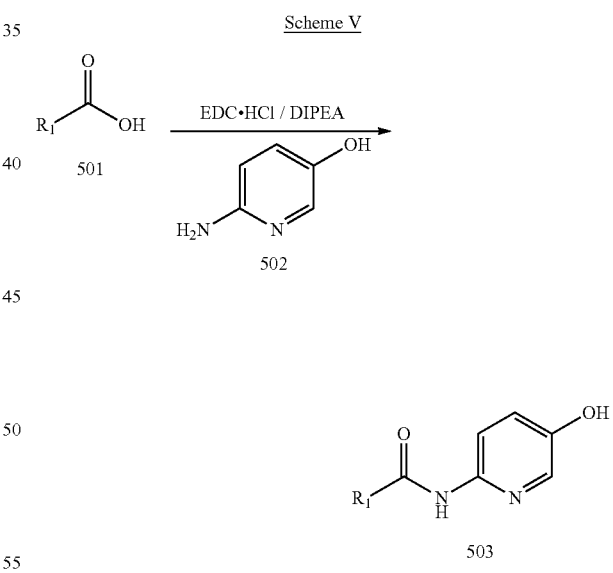

Scheme V can be employed to form N-(5-hydroxypyridin-2-yl)amides. The mixture of 6-aminopyridin-3-ol (502, 1.0 mmol), DMAP (2 mmol), EDC.HCl (1.5 mmol) and acid 501 (1.0 mmol) in DCM (5 mL) was stirred for 16 hours at ambient temperature. The mixture was concentrated and the residue was purified by Prep-HPLC with the following condition: Column: XBridge Prep OBD C18 Column 30×150 mm 5 um; Mobile Phase A: Water (0.1% FA), Mobile Phase B: ACN; Flow rate: 60 mL/min; Gradient: 10% B to 45% B in 7 min; 254/220 nm; to afford amide 503.

Scheme VI

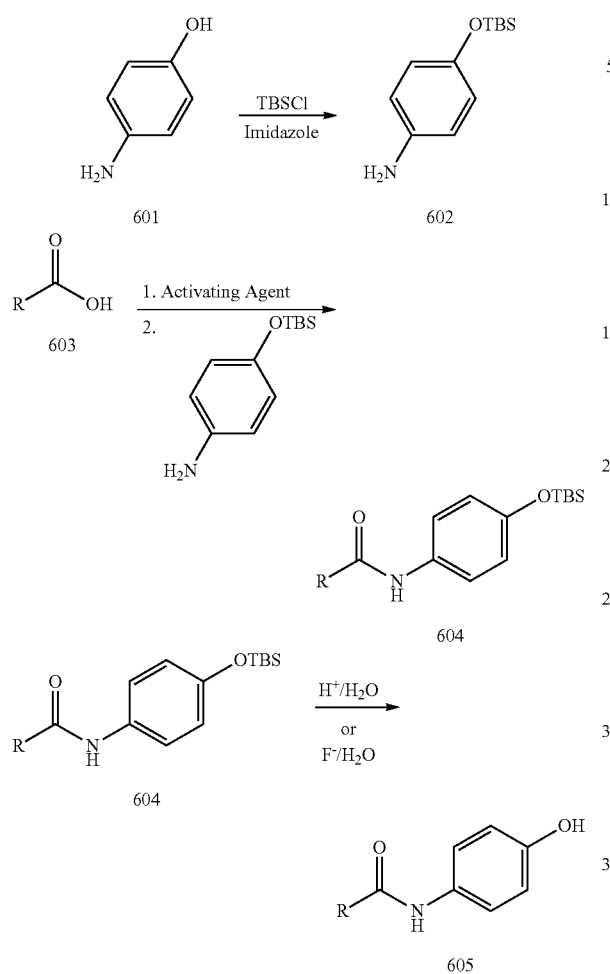

Scheme VI can be used for certain examples utilizing a hydroxy amine for which protection of the hydroxy group is required. The scheme as drawn above utilizes 4-aminophenol as the hydroxy amine 601 for illustrative purposes. In a first step, the hydroxy amine 601 is protected as its TBS ether 602 by reaction with TBS chloride under standard conditions. In a second step, the carboxylic acid 603 is dissolved in an appropriate solvent (e.g. THF or methylene chloride) and treated with an activating agent (e.g. carbonyl diimidazole) at temperatures between 0° C. and room temperature. The TBS ether-amine 402 from the first step is then added. The reactions are stirred until coupling is complete (30 minutes to 8 hours) to produce TBS ether-amide 604. In a third step, the TBS ether group is removed to produce hydroxy amide 605. Certain compounds will require treatment with fluoride anion to accomplish TBS ether cleavage. In certain cases, it may be advantageous to isolate and purify compound 604 before the next step. In certain cases, compound 604 may be taken forward to the next step without purification. Certain examples will undergo cleavage of the TBS group under normal workup conditions. The reaction mixtures are concentrated and then partitioned between methylene chloride and aqueous sodium bicarbonate. The organic phase is concentrated. The amide product can be purified by silica gel chromatography.

The following example compound was prepared by the method of Scheme VI:

Example 1

N-(5-hydroxypyridin-2-yl)-1H-indazole-5-carboxamide (1)

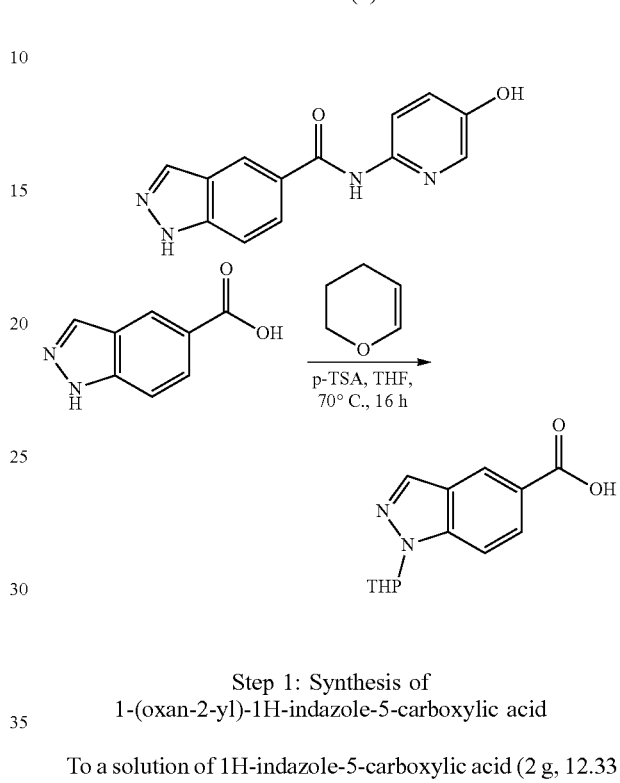

Step 1: Synthesis of
1-(oxan-2-yl)-1H-indazole-5-carboxylic acid

To a solution of 1H-indazole-5-carboxylic acid (2 g, 12.33 mmol) and 4-methylbenzenesulfonic acid (400 mg, 2.32 mmol) in THF (50 mL) was added dropwise 3,4-dihydro-2H-pyran (3 g, 35.66 mmol) with stirring. The resulting solution was stirred for 16 h at 70° C., then diluted with 50 mL $H_2O$. The resulting solution was extracted with 3×50 mL of EtOAc, and the combined organic layers were washed with 20 mL NaCl, dried over $Na_2SO_4$, concentrated under vacuum, and purified with silica gel chromatography using EtOAc petroleum ether (1/5) to afford 1 g (33%) of the title compound as a yellow solid.

LC-MS (ES, m/z): 247.1

Step 2: Synthesis of N-(5-methoxypyridin-2-yl)-1-(oxan-2-yl)-1H-indazole-5-carboxamide A solution of the product from the previous step (200 mg, 0.81 mmol), 5-methoxypyridin-2-amine (101 mg, 0.81 mmol), EDC.HCl (187 mg, 0.97 mmol), and 4-DMAP (99 mg, 0.81 mmol) in $CH_2Cl_2$ (10 mL) was stirred overnight at room temperature. The resulting mixture was concentrated under vacuum, then purified with silica gel chromatography using EtOAC/petroleum ether (1/3) to afford 183 mg (64%) of the title compound as a light yellow solid.

LC-MS (ES, m/z): 353.1

Step 3: Synthesis of N-(5-hydroxypyridin-2-yl)-1H-indazole-5-carboxamide

A solution of the product from the previous step (183 mg, 0.52 mmol) in HBr/AcOH (5 mL) was stirred for 5 h at 100° C., then concentrated under vacuum. The pH was adjusted to 7-8 with $Et_3N$. The crude product was purified by Prep-HPLC under the following conditions (2 #-Analyse HPLC-SHIMADZU (HPLC-10)): Column, XSelect CSH Prep C18 OBD Column, 5 um, 19×150 mm; mobile phase, Water (0.1% FA) and ACN (3.0% ACN up to 22.0% in 7 min); Detector, UV 254/220 nm, to afford 19 mg (14%) of the title compound as an off-white solid.

LC-MS (ES, m/z): 255.0.

$^1$H-NMR: (400 MHz, DMSO-$d_6$) δ 13.31 (s, 1H), 10.48 (s, 1H), 9.72 (s, 1H), 8.57-8.51 (m, 1H), 8.23 (s, 1H), 8.03-7.91 (m, 3H), 7.60 (d, J=8.9 Hz, 1H), 7.26 (dd, J=8.9, 3.0 Hz, 1H).

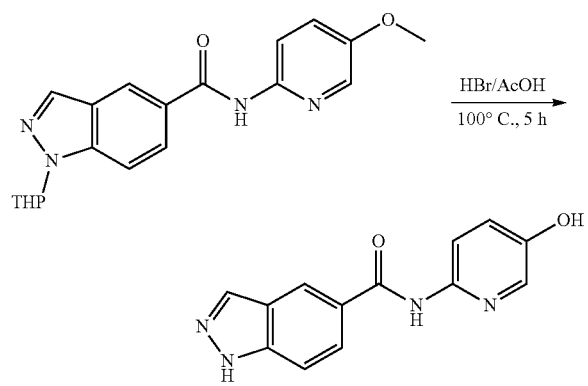

The following example compounds were prepared by the methods set forth above (Ex=example number; Sch=synthetic scheme number).

TABLE 1

| Ex | Sch | IUPAC Name | Structure | Spectral data |
|---|---|---|---|---|
| 2 | I | N-(4-hydroxy-phenyl)-2-naphthamide | 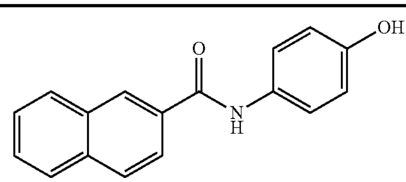 | 1H NMR (400 MHz, DMSO-$d_6$) δ 10.19 (s, 1H), 9.26 (s, 1H), 8.56-8.50 (m, 1H), 8.09-7.94 (m, 4H), 7.67-7.52 (m, 4H), 6.79-6.70 (m, 2H). LC/MS: [(M + 1)]+ = 264.0. |
| 3 | I | (E)-N-(4-hydroxy-phenyl)-3-phenylbut-2-enamide | 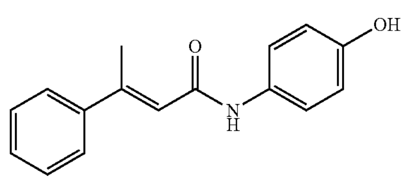 [SMILES: C/C(=C\C(=O)Nc1ccc(O)cc1)c1ccccc1] | 1H NMR (400 MHz, DMSO-$d_6$) δ: 9.84 (s, 1H), 9.16 (s, 1H), 7.54 (d, J = 7.6 Hz, 2H), 7.46-7.36 (m, 5H), 6.70 (d, J = 7.6 Hz, 2H), 6.38 (s, 1H), 2.50 (s, 3H). LC/MS: [(M + 1)]+ = 254.1. |
| 4 | I | N-(4-hydroxy-phenyl)-cinnamide | 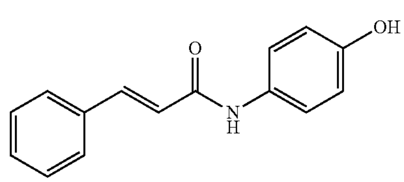 [SMILES: O=C(/C=C/c1ccccc1)Nc1ccc(O)cc1] | 1H NMR (400 MHz, DMSO-$d_6$) δ 9.97 (s, 1H), 9.24 (s, 1H), 7.60 (d, J = 6.8 Hz, 2H), 7.55-7.38 (m, 6H), 6.79 (d, J = 15.6 Hz, 1H), 6.74-6.70 (m, 2H). LC/MS: [(M + 1)]+ = 240.1. |
| 5 | I | N-(4-hydroxy-phenyl)-[1,1'-biphenyl]-4-carboxamide | 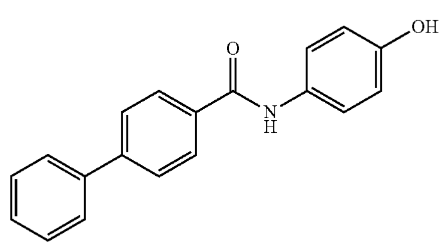 [SMILES: O=C(Nc1ccc(O)cc1)c1ccc(-c2ccccc2)cc1] | 1H NMR (400 MHz, DMSO-$d_6$) δ 10.08 (s, 1H), 9.26 (s, 1H), 8.03 (d, J = 8.4 Hz, 2H), 7.82 (d, J = 8.4 Hz, 2H), 7.75 (d, J = 7.6 Hz, 2H), 7.57-7.49 (m, 4H), 7.44-7.40 (m, 1H), 6.75 (d, J = 8.8 Hz, 2H). LC/MS: [(M + 1)]+ = 290.0. |

TABLE 1-continued

Synthesized examples 2-45

| Ex | Sch | IUPAC Name | Structure | Spectral data |
|---|---|---|---|---|
| 6 | I | (trans)-N-(4-hydroxyphenyl)-2-phenyl-cyclopropane-carboxamide | 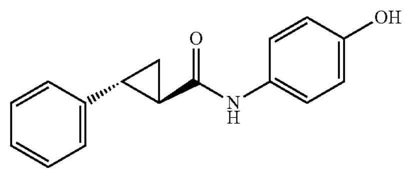 [SMILES: O=C(Nc1ccc(O)cc1)[C@@H]1C[C@H]1c1ccccc1] | 1H NMR (400 MHz, DMSO-d$_6$) δ 9.95 (s, 1H), 9.16 (s, 1H), 7.38-7.37 (m, 2H), 7.28-7.26 (m, 2H), 7.19-7.16 (m, 3H), 6.69-6.65 (m, 2H), 2.34-2.29 (m, 1H), 2.03-1.98 (m, 1H), 1.47-1.42 (m, 1H), 1.33-1.28 (m, 1H). LC/MS: [(M + 1)]+ = 254.0. |
| 7 | II | N-(5-hydroxy-pyridin-2-yl)-2-naphth-amide | 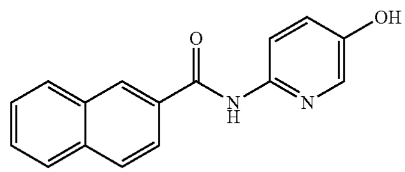 [SMILES: O=C(Nc1ccc(O)cn1)c1ccc2ccccc2c1] | 1H NMR (300 MHz, DMSO-d$_6$) δ 10.66 (s, 1H), 9.74 (s, 1H), 8.67 (s, 1H), 8.08-7.94 (m, 6H), 7.61-7.58 (m, 2H), 7.27 (dd, J = 3.0, 8.7 Hz, 1H). LC/MS: [(M + 1)]+ = 265.0. |
| 8 | II | N-(5-hydroxy-pyridin-2-yl)-cinnamide | 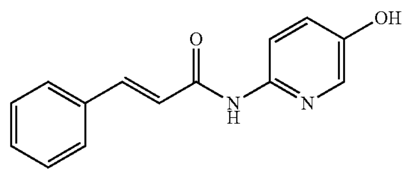 [SMILES: O=C(/C=C/c1ccccc1)Nc1ccc(O)cn1] | 1H NMR (400 MHz, DMSO-d$_6$) δ 10.43 (s, 1H), 9.68 (br s, 1H), 8.07 (d, J = 8.8 Hz, 1H), 7.88 (d, J = 2.8 Hz, 1H), 7.60-7.56 (m, 3H), 7.47-7.40 (m, 3H), 7.23 (dd, J = 2.8, 8.8 Hz, 1H), 7.00 (d, J = 16 Hz, 1H). LC/MS: [(M + 1)]+ = 241.0. |
| 9 | II | N-(5-hydroxy-pyridin-2-yl)-(1,1'-biphenyl)-4-carboxamide | 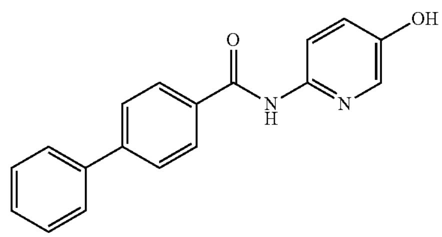 [SMILES: O=C(Nc1ccc(O)cn1)c1ccc(-c2ccccc2)cc1] | 1H NMR (400 MHz, DMSO-d$_6$) δ 10.56 (s, 1H), 9.73 (s, 1H), 8.10-8.08 (m, 2H), 7.99 (d, J = 9.2 Hz, 1H), 7.92 (d, J = 2.8 Hz, 1H), 7.79-7.69 (m, 4H), 7.50-7.47 (m, 2H), 7.42-7.38 (m, 1H), 7.24-7.23 (m, 1H). LC/MS: [(M + 1)]+ = 291.1. |
| 10 | II | (trans)-N-(5-hydroxy-pyridin-2-yl)-2-phenyl-cyclopropane-carboxamide | 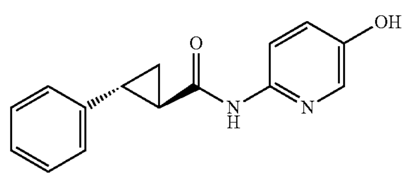 [SMILES: O=C(Nc1ccc(O)cn1)[C@@H]1C[C@H]1c1ccccc1] | 1H NMR (300 MHz, DMSO-d$_6$) δ 10.49 (s, 1H), 9.59 (s, 1H), 7.91 (d, J = 9.3 Hz, 1H), 7.83 (d, J = 2.7 Hz, 1H), 7.31-7.26 (m, 2H), 7.21-7.14 (m, 4H), 2.37-2.26 (m, 2H), 1.47-1.41 (m, 1H), 1.34-1.27 (m, 1H). LC/MS: [(M + 1)]+ = 255.0. |
| 11 | III | N-(4-hydroxy-phenyl)-3-methyl-2-butenamide | 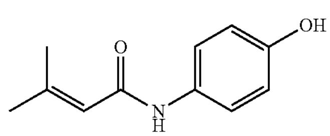 | 1H NMR (300 MHz, DMSO-d$_6$) δ 9.55 (s, 1H), 9.12 (s, 1H), 7.44-7.32 (m, 2H), 6.72-6.60 (m, 2H), 5.84-5.76 (m, 1H), 2.12 (d, J = 1.2 Hz, 3H), 1.83 (d, J = 1.3 Hz, 3H). LC/MS: [(M + 1)]+ = 192. |
| 12 | III | N-(4-hydroxy-phenyl)-phenyl-acetamide | 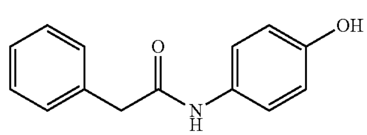 [SMILES: O=C(Cc1ccccc1)Nc1ccc(O)cc1] | 1H NMR (300 MHz, DMSO-d$_6$) δ 9.89 (s, 1H), 9.16 (s, 1H), 7.41-7.16 (m, 7H), 6.72-6.60 (m, 2H), 3.56 (s, 2H). LC/MS: [(M + 1)]+ = 228. |

TABLE 1-continued

Synthesized examples 2-45

| Ex | Sch | IUPAC Name | Structure | Spectral data |
|---|---|---|---|---|
| 13 | III | N-(4-hydroxy-phenyl)-1-napthamide | 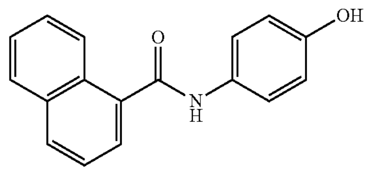 [SMILES: O=C(Nc1ccc(O)cc1)c1cccc2ccccc12] | 1H NMR (400 MHz, DMSO-$d_6$) δ 10.33 (s, 1H), 9.29 (s, 1H), 8.23-8.14 (m, 1H), 8.10-7.97 (m, 2H), 7.72 (dd, J = 7.1, 1.3 Hz, 1H), 7.60 (dt, J = 9.1, 3.3 Hz, 5H), 6.82-6.73 (m, 2H). LC/MS: [(M + 1)]+ = 264. |
| 14 | III | N-(4-hydroxy-phenyl)-1H-indazole-5-carboxamide | 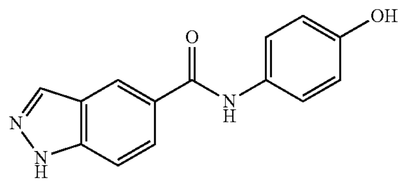 [SMILES: O=C(Nc1ccc(O)cc1)c1ccc2[nH]ncc2c1] | 1H NMR (DMSO) δ: 13.35-13.28 (s, 1H), 10.06-10.00 (s, 1H), 9.27-9.20 (s, 1H), 8.47-8.39 (d, J = 1.3 Hz, 1H), 8.27-8.20 (s, 1H), 7.97-7.87 (dd, J = 8.8, 1.6 Hz, 1H), 7.66-7.49 (m, 3H), 6.79-6.67 (m, 2H). LC/MS: [(M + 1)]+ = 254. |
| 15 | III | N-(4-hydroxy-phenyl)-4-cyclohexyl-benzamide | 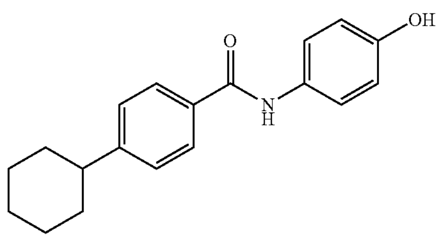 [SMILES: O=C(Nc1ccc(O)cc1)c1ccc(C2CCCCC2)cc1] | 1H NMR (DMSO) δ: 9.95-9.89 (s, 1H), 9.25-9.19 (s, 1H), 7.88-7.79 (m, 2H), 7.57-7.45 (m, 2H), 7.39-7.30 (m, 2H), 6.78-6.66 (m, 2H), 2.60-2.54 (s, 1H), 1.85-1.66 (dd, J = 25.7, 11.0 Hz, 5H), 1.53-1.19 (tq, J = 24.5, 24.5, 11.5, 11.5, 11.3 Hz, 5H). LC/MS: [(M + 1)]+ = 296. |
| 16 | III | N-(4-hydroxy-phenyl)-4'-hydroxy-biphenyl-4-carboxamide | 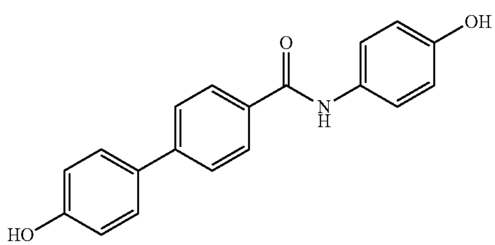 | 1H NMR (DMSO) δ: 10.05-10.00 (s, 1H), 9.71-9.66 (s, 1H), 9.28-9.23 (s, 1H), 8.02-7.95 (d, J = 8.4 Hz, 2H), 7.76-7.69 (m, 2H), 7.63-7.51 (m, 4H), 6.92-6.84 (m, 2H), 6.78-6.71 (m, 2H). LC/MS: [(M + 1)]+ = 306. |
| 17 | | | This example intentionally left empty. | |
| 18 | IV | N-(5-hydroxy-pyridin-2-yl)-phenyl-acetamide | 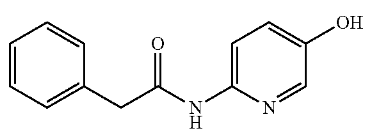 [SMILES: O=C(Cc1ccccc1)Nc1ccc(O)cn1] | 1H NMR (400 MHz, DMSO-$d_6$) δ 10.74 (s, 1H), 8.13-7.77 (m, 2H), 7.33-7.21 (m, 6H), 3.68 (s, 2H). LC/MS: [(M + 1)]+ = 229. |
| 19 | V | N-(5-hydroxy-pyridin-2-yl)-1-napthamide | 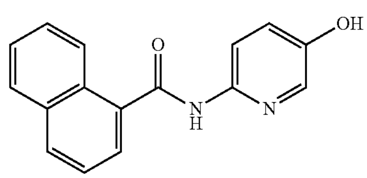 | 1H NMR (DMSO) δ: 8.85-8.75 (m, 1H), 8.46-8.36 (dd, J = 7.3, 1.3 Hz, 1H), 8.33-8.24 (d, J = 8.2 Hz, 1H), 8.13-8.04 (m, 1H), 7.97-7.90 (d, J = 2.8 Hz, 1H), 7.77-7.58 (m, 3H), 7.49-7.39 (dd, J = 8.9, 2.9 Hz, 1H), 6.58-6.49 (d, J = 8.9 Hz, 1H), 6.04-5.97 (s, 2H). LC/MS: [(M + 1)]+ = 265. |

TABLE 1-continued

Synthesized examples 2-45

| Ex | Sch | IUPAC Name | Structure | Spectral data |
|---|---|---|---|---|
| 20 | V | N-(5-hydroxy-pyridin-2-yl)-4-cyclohexyl-benzamide | 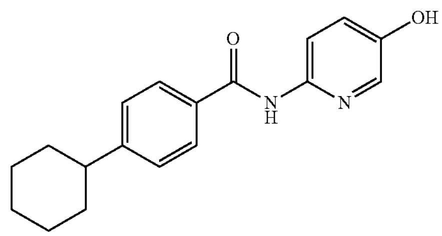 [SMILES: O=C(Nc1ccc(O)cn1)c1ccc(C2CCCCC2)cc1] | 1H NMR (DMSO) δ: 8.07-7.97 (m, 2H), 7.89-7.81 (d, J = 2.8 Hz, 1H), 7.50-7.35 (m, 3H), 6.61-6.51 (d, J = 9.0 Hz, 1H), 2.69-2.55 (t, J = 11.0, 11.0 Hz, 1H), 1.85-1.66 (dd, J = 26.4, 11.1 Hz, 5H), 1.54-1.19 (m, 5H). LC/MS: [(M + 1)]+ = 297. |
| 21 | V | N-(5-hydroxy-pyridin-2-yl)-4'-hydroxy-biphenyl-4-carboxamide | 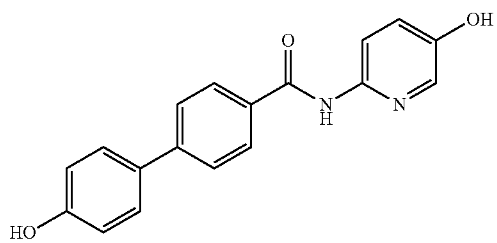 | 1H NMR (DMSO) δ: 8.20-8.06 (m, 2H), 7.88-7.76 (m, 3H), 7.68-7.57 (m, 2H), 7.40-7.29 (dd, J = 8.9, 2.9 Hz, 1H), 6.95-6.83 (m, 2H), 6.55-6.45 (dd, J = 8.9, 0.7 Hz, 1H), 6.01-5.94 (s, 2H). LC/MS: [(M + 1)]+ = 307. |
| 22 | V | N-(5-hydroxy-pyridin-2-yl)-4'-methoxy-biphenyl-4-carboxamide | 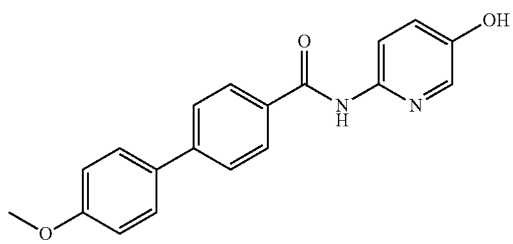 [SMILES: COc1ccc(-c2ccc(C(=O)Nc3ccc(O)cn3)cc2)cc1] | 1H NMR (DMSO) δ: 8.19-8.11 (m, 2H), 7.90-7.82 (m, 3H), 7.80-7.71 (m, 2H), 7.40-7.33 (dd, J = 8.9, 2.9 Hz, 1H), 7.13-7.04 (m, 2H), 6.56-6.48 (d, J = 8.9 Hz, 1H), 6.02-5.97 (s, 2H), 3.85-3.80 (s, 3H). LC/MS: [(M + 1)]+ = 321. |
| 23 | V | N-(5-hydroxy-pyridin-2-yl)-4'-cyano-biphenyl-4-carboxamide | 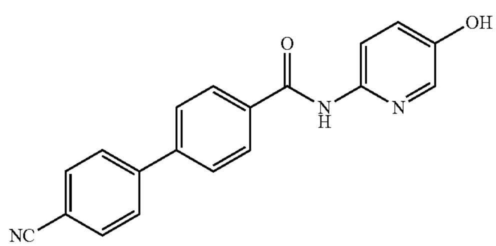 | 1H NMR (DMSO) δ: 8.27-8.18 (m, 2H), 8.06-7.95 (d, J = 8.9 Hz, 6H), 7.91-7.85 (d, J = 2.8 Hz, 1H), 7.42-7.34 (dd, J = 8.9, 2.9 Hz, 1H), 6.56-6.48 (d, J = 8.9 Hz, 1H), 6.04-5.99 (s, 2H). LC/MS: [(M + 1)]+ = 316. |
| 24 | V | N-(5-hydroxy-pyridin-2-yl)-4'-chloro-biphenyl-4-carboxamide | 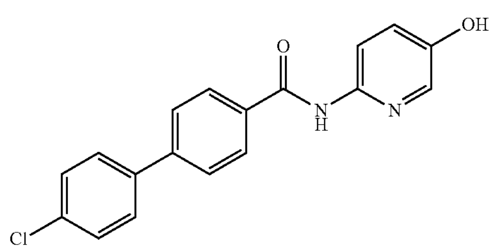 [SMILES: O=C(Nc1ccc(O)cn1)c1ccc(-c2ccc(Cl)cc2)cc1] | 1H NMR (DMSO) δ: 8.23-8.15(m, 2H), 7.96-7.78 (m, 5H), 7.63-7.55 (m, 2H), 7.41-7.33 (dd, J = 8.9, 2.9 Hz, 1H), 6.56-6.48 (d, J = 8.9 Hz, 1H), 6.03-5.98 (s, 2H). LC/MS: [(M + 1)]+ = 325. |
| 25 | V | N-(5-hydroxy-pyridin-2-yl)-benzamide | 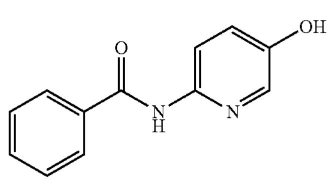 [SMILES: O=C(Nc1ccc(O)cn1)c1ccccc1] | 1H NMR (DMSO) δ: 8.16-8.05 (m, 2H), 7.88-7.68 (m, 2H), 7.66-7.53 (m, 2H), 7.39-7.29 (dd, J = 8.9, 2.9 Hz, 1H), 6.54-6.45 (dd, J = 8.9, 0.7 Hz, 1H), 6.01-5.95 (s, 2H). LC/MS: [(M + 1)]+ = 215. |

TABLE 1-continued

Synthesized examples 2-45

| Ex | Sch | IUPAC Name | Structure | Spectral data |
|---|---|---|---|---|
| 26 | V | N-(5-hydroxy-pyridin-2-yl)-4-methoxy-benzamide | 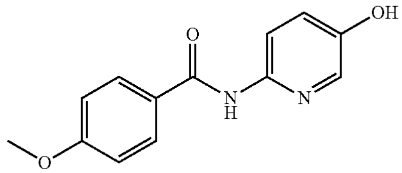 [SMILES: COc1ccc(C(=O)Nc2ccc(O)cn2)cc1] | 1H NMR (DMSO) δ: 8.11-7.99 (m, 2H), 7.85-7.77 (m, 1H), 7.36-7.25 (dd, J = 8.9, 2.9 Hz, 1H), 7.16-7.05 (m, 2H), 6.53-6.43 (dd, J = 8.9, 0.7 Hz, 1H), 5.99-5.92 (s, 2H), 3.89-3.83 (s, 3H). LC/MS: [(M + 1)]+ = 245. |
| 27 | VI | N-(5-hydroxy-pyridin-2-yl)-4-isopropyl-benzamide | 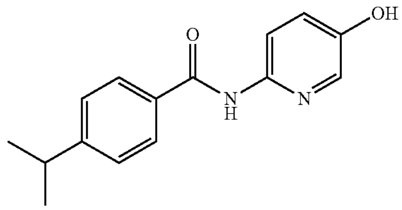 [SMILES: CC(C)c1ccc(C(=O)Nc2ccc(O)cn2)cc1] | 1H NMR (400 MHz, DMSO-$d_6$) δ 10.41 (s, 1H), 9.73 (s, 1H), 8.02-7.89 (m, 4H), 7.40-7.32 (m, 2H), 7.25 (dd, J = 8.9, 3.0 Hz, 1H), 2.96 (h, J = 6.9, 6.9, 6.9, 6.9, 6.9 Hz, 1H), 1.23 (d, J = 6.9 Hz, 6H). LC-MS: (ES, m/z): 257.1 |
| 28 | VI | (1r,4r)-N-(5-hydroxy-pyridin-2-yl)-4-phenyl-cyclohexane-1-carboxamide | 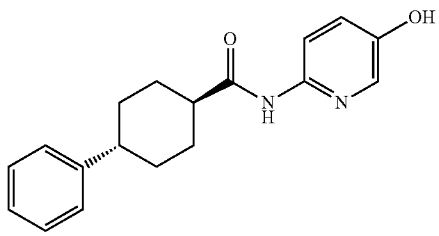 [SMILES: O=C(Nc1ccc(O)cn1)[C@H]1CC[C@H](c2ccccc2)CC1] | 1H NMR (400 MHz, DMSO-$d_6$) δ 10.11 (s, 1H), 9.58 (s, 1H), 7.93 (d, J = 8.9 Hz, 1H), 7.85 (d, J = 2.9 Hz, 1H), 7.34-7.21 (m, 4H), 7.18 (ddd, J = 8.8, 6.2, 2.2 Hz, 2H), 2.64-2.44 (m, 1H), 1.90 (ddd, J = 17.9, 13.0, 3.6 Hz, 4H), 1.69-1.52 (m, 2H), 1.46 (qd, J = 13.1, 13.1, 12.6, 2.8 Hz, 2H). LC-MS: (ES, m/z): 297.1 |
| 29 | VI | N-(5-hydroxy-pyridin-2-yl)-octanamide | 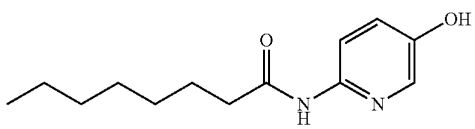 [SMILES: CCCCCCCC(=O)Nc1ccc(O)cn1] | 1H NMR: (400 MHz, DMSO-$d_6$) δ 10.10 (s, 1H), 9.57 (s, 1H), 7.90 (d, J = 8.9 Hz, 1H), 7.83 (d, J = 2.9 Hz, 1H), 7.16 (dd, J = 8.9, 3.0 Hz, 1H), 2.31 (t, J = 7.4, 7.4 Hz, 2H), 1.55 (p, J = 7.1, 7.1, 7.1, 7.1 Hz, 2H), 1.26 (td, J = 6.6, 6.2, 4.2 Hz, 8H), 0.90-0.82 (m, 3H). LC-MS: (ES, m/z): 237.2 |
| 30 | VI | N-(5-hydroxy-pyridin-2-yl)-cyclohexane-carboxamide | 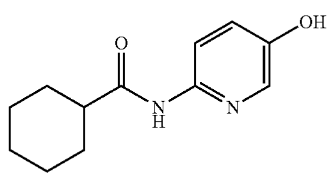 [SMILES: O=C(Nc1ccc(O)cn1)C1CCCCC1] | 1H NMR: (400 MHz, DMSO-$d_6$) δ 10.02 (s, 1H), 9.56 (s, 1H), 7.90 (d, J = 8.9 Hz, 1H), 7.83 (d, J = 2.9 Hz, 1H), 7.16 (dd, J = 8.9, 3.0 Hz, 1H), 2.43 (tt, J = 11.6, 11.6, 3.4, 3.4 Hz, 1H), 1.80-1.68 (m, 4H), 1.68-1.58 (m, 1H), 1.38 (qd, J = 13.3, 13.3, 12.5, 3.5 Hz, 2H), 1.31-1.09 (m, 3H). LC-MS: (ES, m/z): 221.1 |
| 31 | VI | N-(5-hydroxy-pyridin-2-yl)-7-methyloctan-amide | 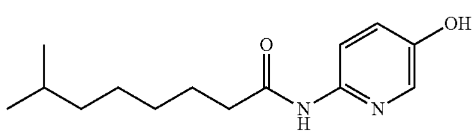 [SMILES: CC(C)CCCCCC(=O)Nc1ccc(O)cn1] | 1H NMR (DMSO): δ (400 MHz, DMSO-$d_6$) 10.10 (s, 1H), 9.56 (s, 1H), 7.90 (d, J = 8.9 Hz, 1H), 7.83 (dd, J = 2.9, 0.7 Hz, 1H), 7.17 (dd, J = 8.9, 3.0 Hz, 1H), 2.31 (t, J = 7.4, 7.4 Hz, 2H), 1.53 (dh, J = 26.6, 6.9, 6.9, 6.6, 6.6, 6.6 Hz, 3H), 1.26 (pd, J = 7.5, 7.5, 7.5, 6.8, 3.0 Hz, 4H), 1.20-1.09 (m, 2H), 0.85 (d, J = 6.6 Hz, 6H). LC-MS:(ES, m/z): 251.1 |

TABLE 1-continued

Synthesized examples 2-45

| Ex | Sch | IUPAC Name | Structure | Spectral data |
|---|---|---|---|---|
| 32 | VI | (1r,4r)-4-(4-chlorophenyl)-N-(5-hydroxy-pyridin-2-yl)-cyclohexane-1-carboxamide | 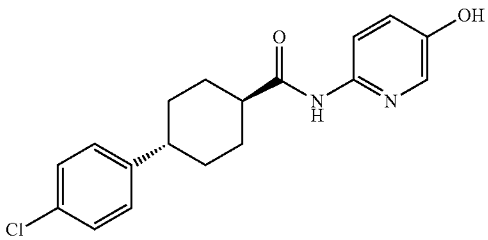 [SMILES: O=C(Nc1ccc(O)cn1)[C@H]1CC[C@H](c2ccc(Cl)cc2)CC1] | 1H NMR (400 MHz, DMSO-$d_6$): δ 10.12 (s, 1H), 9.58 (s, 1H), 7.92 (d, J = 8.9 Hz, 1H), 7.89-7.80 (m, 1H), 7.38-7.31 (m, 2H), 7.30-7.24 (m, 2H), 7.17 (dd, J = 8.9, 3.0 Hz, 1H), 2.56 (dt, J = 12.3, 3.6, 3.6 Hz, 1H), 2.48 (d, J = 4.5 Hz, 1H), 1.96-1.80 (m, 4H), 1.59 (qd, J = 12.6, 12.1, 12.1, 2.9 Hz, 2H), 1.51-1.35 (m, 2H). LC-MS: (ES, m/z): 331.1 |
| 33 | VI | N-(5-hydroxy-pyridin-2-yl)-4-(pyridin-2-yl)benzamide | 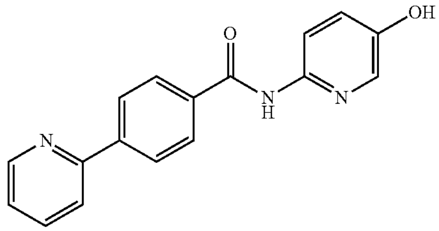 [SMILES: O=C(Nc1ccc(O)cn1)c1ccc(-c2ccccn2)cc1] | 1H NMR (400 MHz, DMSO-$d_6$) δ 10.61 (s, 1H), 10.17-9.33 (m, 1H), 8.72 (d, J = 4.7 Hz, 1H), 8.36-7.74 (m, 8H), 7.47-7.14 (m, 2H). LC-MS: (ES, m/z): 261 |
| 34 | VI | N-(5-hydroxy-pyridin-2-yl)-4-(pyridin-3-yl)benzamide | 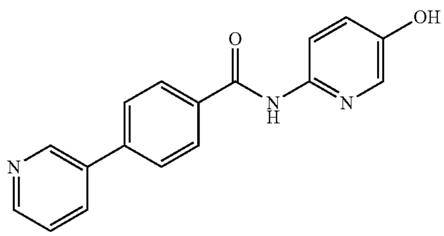 [SMILES: O=C(Nc1ccc(O)cn1)c1ccc(-c2cccnc2)cc1] | 1H NMR (400 MHz, DMSO-$d_6$) δ 10.62 (s, 1H), 9.80 (s, 1H), 8.99 (d, J = 2.4 Hz, 1H), 8.63 (d, J = 4.7, 1.5 Hz, 1H), 8.22-8.11 (m,3H), 8.02-7.87 (m, 7H), 7.53 (d, J = 8.0, 4.8 Hz, 1H), 7.27 (d, J = 8.9, 3.0 Hz, 1H). LC-MS: (ES, m/z): 261 |
| 35 | VI | 4-(tert-butyl)-N-(5-hydroxy-pyridin-2-yl)-benzamide | 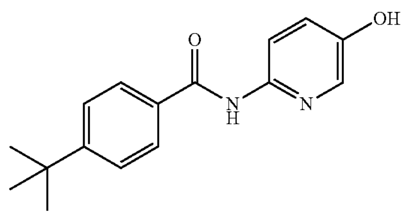 [SMILES: CC(C)(C)c1ccc(C(=O)Nc2ccc(O)cn2)cc1] | 1H NMR (400 MHz, DMSO-$d_6$) δ 10.41 (s, 1H), 8.02-7.90 (m, 4H), 7.55-7.47 (m, 2H), 7.25 (dd, J = 8.9, 3.0 Hz, 1H), 1.32 (s, 9H). LC-MS: (ES, m/z): 271 |
| 36 | VI | N-(5-hydroxy-pyridin-2-yl)-6-methoxy-hexanamide | 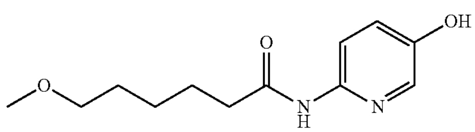 [SMILES: COCCCCCC(=O)Nc1ccc(O)cn1] | 1H NMR (300 MHz, DMSO-$d_6$) δ 10.22 (s, 1H), 9.68 (s, 1H), 7.87 (m, 2H), 7.21 (dd, J = 8.9, 3.0 Hz, 1H), 3.29 (t, J = 6.4, 6.4 Hz, 2H), 3.21 (s, 3H), 2.33 (t, J = 7.3, 7.3 Hz, 2H), 1.54 (dp, J = 21.0, 7.0, 7.0, 6.6, 6.6 Hz, 4H), 1.31 (m, 2H). LC-MS (ES, m/z): 239.1 |
| 37 | VI | N-(5-hydroxy-pyridin-2-yl)-5-isopropoxy-pentanamide | 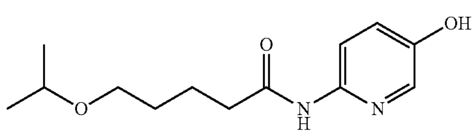 [SMILES: CC(C)OCCCCC(=O)Nc1ccc(O)cn1] | 1H NMR (300 MHz, DMSO-$d_6$) δ 10.12 (s, 1H), 9.59 (s, 1H), 7.91 (d, J = 8.9 Hz, 1H), 7.83 (d, J = 2.9 Hz, 1H), 7.17 (d, J = 8.9, 3.0 Hz, 1H), 3.50 (m, J = 6.1 Hz, 1H), 3.37 (s, 2H), 2.33 (t, J = 7.3 Hz, 2H), 1.66-1.55 (m, 2H), 1.55-1.40 (m, 2H), 1.07 (d, J = 6.1 Hz, 6H). LC-MS: (ES, m/z): 253 |

TABLE 1-continued

Synthesized examples 2-45

| Ex | Sch | IUPAC Name | Structure | Spectral data |
|---|---|---|---|---|
| 38 | VI | 2'-chloro-N-(5-hydroxy-pyridin-2-yl)-[1,1'-biphenyl]-4-carboxamide | 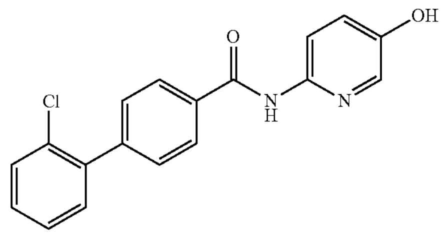 [SMILES: O=C(Nc1ccc(O)cn1)c1ccc(-c2ccccc2Cl)cc1] | 1H NMR (400 MHz, DMSO-$d_6$) δ 10.69 (s, 1H), 9.87 (s, 1H), 8.12 (m, 2H), 7.99 (m, 2H), 7.59 (m, 3H), 7.46 (m, 3H), 7.32 (dd, J = 8.9, 3.0 Hz, 1H). LC-MS: (ES, m/z): 324.90 |
| 39 | VI | 2',6'-dichloro-N-(5-hydroxy-pyridin-2-yl)-[1,1'-biphenyl]-4-carboxamide | 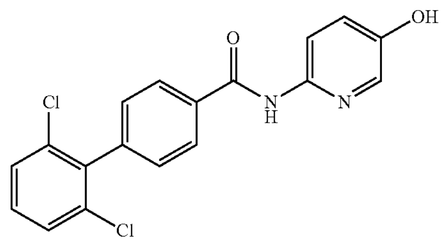 [SMILES: O=C(Nc1ccc(O)cn1)c1ccc(-c2c(Cl)cccc2Cl)cc1] | 1H NMR (300 MHz, DMSO-$d_6$) δ 10.71 (s, 1H), 9.84 (s, 1H), 8.13 (d, J = 8.2 Hz, 2H), 7.98 (m, 2H), 7.63 (d, J = 8.0 Hz, 2H), 7.49 (m, 1H), 7.42 (d, J = 8.1 Hz, 2H), 7.31 (dd, J = 8.9, 3.0 Hz, 1H). LC-MS (ES, m/z): 285.85 |
| 40 | VI | (1r,4r)-N-(5-hydroxypyridin-2-yl)-4-isopropoxycyclohexane-1-carboxamide | 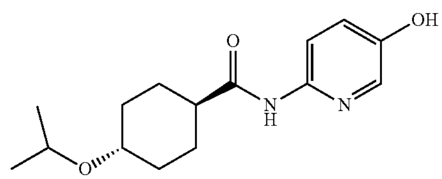 [SMILES: CC(C)O[C@H]1CC[C@H](C(=O)Nc2ccc(O)cn2)CC1] | 1H NMR (300 MHz, DMSO-$d_6$) δ 10.05 (s, 1H), 9.58 (s, 1H), 7.92-7.78 (m, 2H), 7.15 (dd, J = 8.9, 3.0 Hz, 1H), 3.68 (hept, J = 6.1 Hz, 1H), 3.25 (ddt, J = 10.5, 8.0, 4.0 Hz, 1H), 2.37 (tt, J = 12.0, 3.5 Hz, 1H), 1.93 (dd, J = 12.6, 4.1 Hz, 2H), 1.85-1.73 (m, 2H), 1.44 (qd, J = 13.1, 3.1 Hz, 2H), 1.20-1.00 (m, 8H). LC-MS: (ES, m/z): 279 |
| 41 | VI | (1s,4s)-N-(5-hydroxypyridin-2-yl)-4-isopropoxycyclohexane-1-carboxamide | 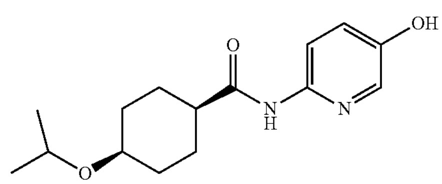 [SMILES: CC(C)O[C@H]1CC[C@@H](C(=O)Nc2ccc(O)cn2)CC1] | 1H NMR (300 MHz, DMSO-$d_6$) δ 10.00 (s, 1H), 9.50 (s, 1H), 7.93-7.78 (m, 2H), 7.15 (dd, J = 8.9, 3.0 Hz, 1H), 3.59 (dt, J = 11.7, 5.7 Hz, 2H), 2.52-2.36 (m, 1H), 1.83-1.63 (m, 4H), 1.55-1.30 (m, 4H), 1.06 (d, J = 6.1 Hz, 6H). LC-MS: (ES, m/z): 279 |
| 42 | VI | 4-ethyl-N-(5-hydroxy-pyridin-2-yl)-benzamide | 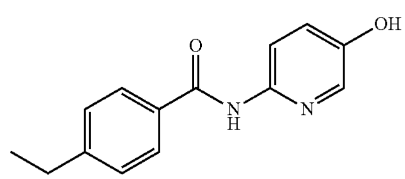 [SMILES: CCc1ccc(C(=O)Nc2ccc(O)cn2)cc1] | 1H NMR (400 MHz, DMSO-$d_6$) δ 10.46 (s, 1H), 9.78 (s, 1H), 8.02-7.91 (m, 4H), 7.36-7.24 (m, 3H), 2.67 (q, J = 7.6 Hz, 2H), 1.21 (t, J = 7.6 Hz, 3H). LC-MS: (ES, m/z): 243 |
| 43 | VI | N-(5-hydroxy-pyridin-2-yl)-4-methylbenzamide | 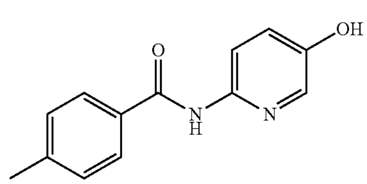 [SMILES: Cc1ccc(C(=O)Nc2ccc(O)cn2)cc1] | 1H NMR (400 MHz, DMSO-$d_6$) δ 10.40 (s, 1H), 9.74 (s, 1H), 7.98 (d, J = 8.9 Hz, 1H), 7.92 (m, 3H), 7.30 (d, J = 8.0 Hz, 2H), 7.25 (d, J = 8.9, 3.0 Hz, 1H), 2.37 (s, 3H). LC-MS: (ES, m/z): 229.1 |

TABLE 1-continued

Synthesized examples 2-45

| Ex | Sch | IUPAC Name | Structure | Spectral data |
|---|---|---|---|---|
| 44 | VI | N-(5-hydroxy-pyridin-2-yl)-4-(trifluoro-methyl)-benzamide | 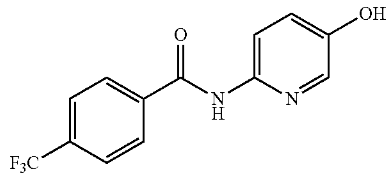 [SMILES: O=C(Nc1ccc(O)cn1)c1ccc(C(F)(F)F)cc1] | 1H NMR (400 MHz, DMSO-d$_6$) δ 10.81 (s, 1H), 9.80 (s, 1H), 8.19 (d, J = 8.1 Hz, 2H), 8.00 (d, J = 8.9 Hz, 1H), 7.96 (d, J = 2.9 Hz, 1H), 7.86 (d, J = 8.1 Hz, 2H), 7.28 (d, J = 8.9 Hz, 1H). LC-MS (ES, m/z): 283.0 |
| 45 | VI | N-(5-hydroxy-pyridin-2-yl)-4-(1,1,1-trifluoro-propan-2-yl)-benzamide | 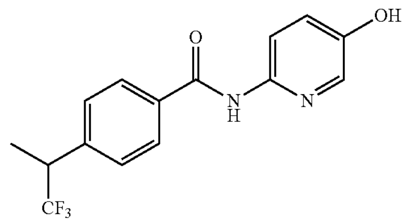 [SMILES: CC(c1ccc(C(=O)Nc2ccc(O)cn2)cc1)C(F)(F)F] | 1H NMR (300 MHz DMSO-d$_6$) δ 10.54 (s, 1H), 9.76 (s, 1H), 8.06-7.89 (m, 4H), 7.51 (d, J = 8.0 Hz, 2H), 7.25 (dd, J = 8.9, 3.0 Hz, 1H), 4.02-3.78 (m, 1H), 1.47 (d, J = 7.2 Hz, 3H). LC-MS (ES, m/z): 311 |

Example 46

N-(5-hydroxypyridin-2-yl)-2-[1-[4-(trifluoromethyl)phenyl]piperidin-4-yl]acetamide

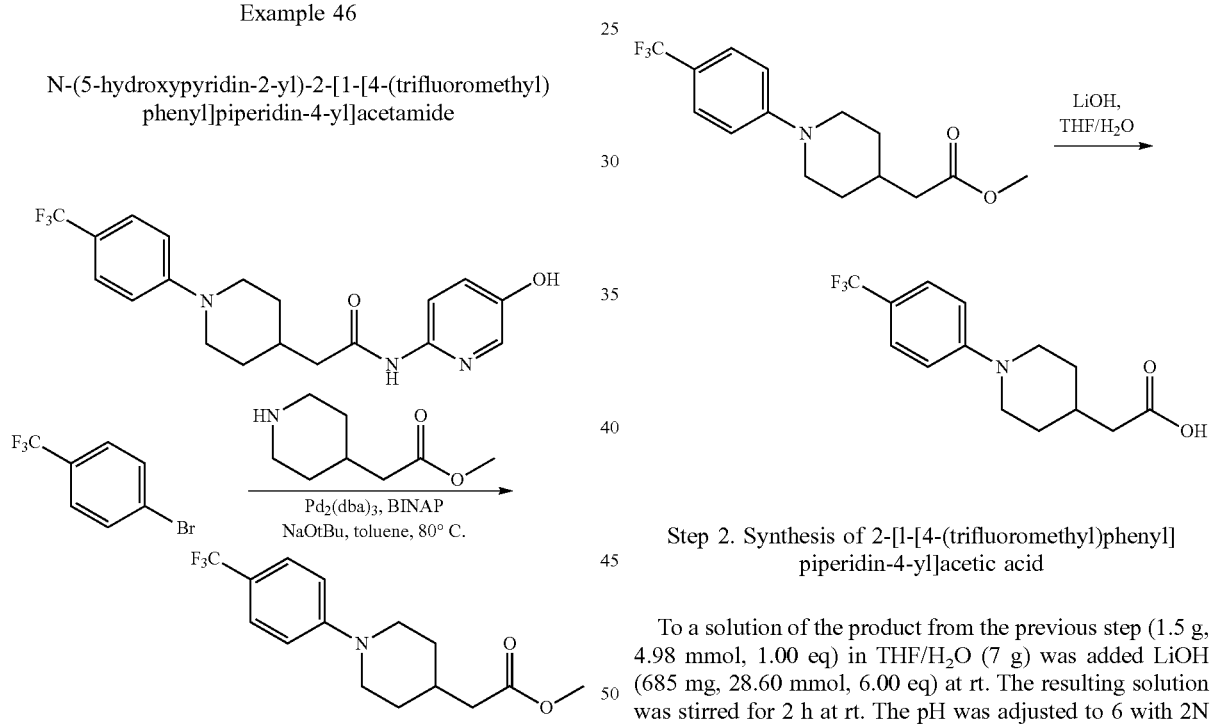

Step 1. Synthesis of methyl 2-[1-[4-(trifluoromethyl)phenyl]piperidin-4-yl]acetate A solution of 1-bromo-4-(trifluoromethyl)benzene (2.2 g, 9.78 mmol, 1.00 eq), methyl 2-(piperidin-4-yl)acetate (2 g, 9.66 mmol, 1.00 eq), NaOtBu (1.4 g, 1.50 eq), BINAP (0.30 g, 0.05 eq), Pd$_2$(dba)$_3$ (440 mg, 0.48 mmol, 0.05 eq) in toluene (25 mL) was stirred for 16 h at 80° C., then cooled and extracted with 2×60 mL of EtOAc. The combined organic layers were concentrated under vacuum and purified with silica gel chromatography using EtOAc/hexane (1/2) to afford 1.5 g (51%) of the title compound as an off-white solid.

Step 2. Synthesis of 2-[1-[4-(trifluoromethyl)phenyl]piperidin-4-yl]acetic acid

To a solution of the product from the previous step (1.5 g, 4.98 mmol, 1.00 eq) in THF/H$_2$O (7 g) was added LiOH (685 mg, 28.60 mmol, 6.00 eq) at rt. The resulting solution was stirred for 2 h at rt. The pH was adjusted to 6 with 2N HCl. The resulting solution was extracted with 2×50 mL of EtOAc. The combined organic layers were concentrated under vacuum and purified with silica gel chromatography using EtOAc/hexane (2:1) to afford 800 mg (56%) of the title compound as an off-white solid. LC-MS: (ES, m/z): 288.

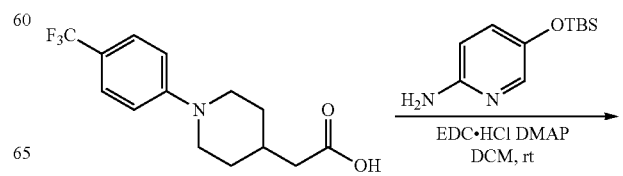

-continued

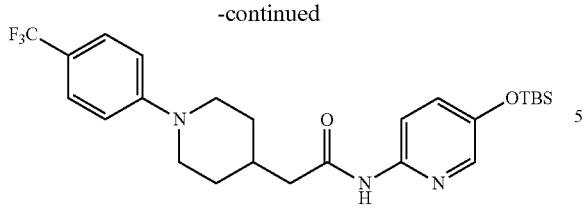

Step 3. Synthesis of N-[5-[(tert-butyldimethylsilyl)oxy]pyridin-2-yl]-2-[1-[4-(trifluoromethyl)phenyl]piperidin-4-yl]acetamide A solution of the product from the previous step (287 mg, 1.00 mmol, 1.00 eq), EDC.HCl (230 mg, 1.20 eq), 5-[(tert-butyldimethylsilyl)oxy]pyridin-2-amine (224 mg, 1.00 mmol, 1.00 eq), DMAP (122 mg, 1.00 eq), CH$_2$Cl$_2$ (5 mL). The resulting solution was stirred for 16 min at room temperature. The resulting solution was extracted with 2×20 mL of EtOAc and the organic layers combined and concentrated under vacuum. The residue was applied onto a silica gel column with EtOAc/hexane (2/1) to afford 150 mg (30%) of the title compound as an off-white solid. LC-MS: (ES, m/z): 494.

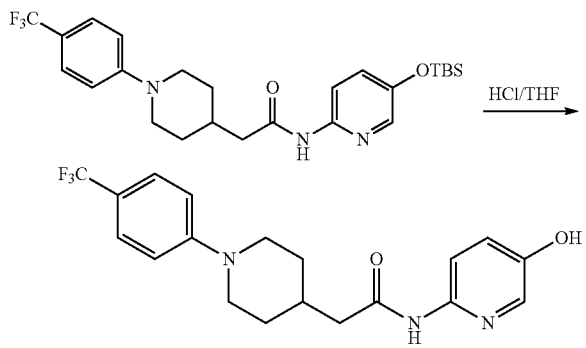

Step 4. Synthesis of N-(5-hydroxypyridin-2-yl)-2-[1-[4-(trifluoromethyl)phenyl]piperidin-4-yl] acetamide Into a 100-mL round-bottom flask, was placed the product from the previous step (150 mg, 0.30 mmol, 1.00 eq), THF (2 mL). This was followed by the addition of 2N HCl (1 mL) dropwise with stirring at room temperature. The resulting solution was stirred for 2 h at room temperature. The resulting mixture was concentrated under vacuum. The crude product (150 mg) was purified by Prep-HPLC with the following conditions (2 #SHIMADZU (HPLC-01)): Column, XBridge Prep OBD C18 Column, 30×150 mm 5 um; mobile phase, Water (10 MMOL/L NH4HCO3) and ACN (35.0% ACN up to 66.0% in 8 min); Detector, UV 254/220 nm. This resulted in 58.8 mg (51%) of the title compound as an off-white solid.

$^1$H NMR (400 MHz, DMSO-d$_6$) δ 10.17 (s, 1H), 9.64 (s, 1H), 7.92 (d, J=8.9 Hz, 1H), 7.83 (d, J=2.9 Hz, 1H), 7.46 (d, J=8.5 Hz, 2H), 7.17 (dd, J=8.9, 3.0 Hz, 1H), 7.03 (d, J=8.6 Hz, 2H), 3.85 (d, J=12.6 Hz, 2H), 2.81 (t, J=12.0 Hz, 2H), 2.29 (d, J=7.1 Hz, 2H), 2.13-1.87 (m, 1H), 1.77-1.68 (m, 2H), 1.25 (tt, J=12.2, 6.8 Hz, 2H).
LC-MS: (ES, m/z): 380

Example 47

N-(5-hydroxypyridin-2-yl)-2-[4-[4-(trifluoromethyl)phenyl]piperazin-1-yl]acetamide

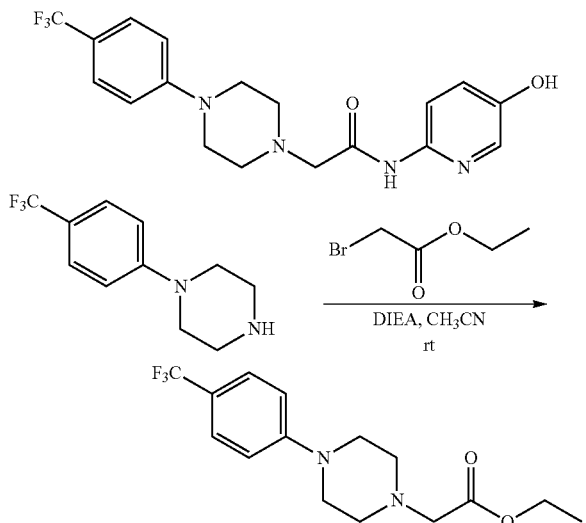

Step 1. Synthesis of ethyl 2-[4-[4-(trifluoromethyl)phenyl]piperazin-1-yl]acetate A solution of 1-[4-(trifluoromethyl)phenyl]piperazine (500 mg, 2.17 mmol). ethyl 2-bromoacetate (545 mg, 3.26 mmol), and DIEA (421 mg) in CH$_3$CN (20 mL) was stirred for 2 h at RT. The resulting mixture was concentrated under vacuum. The residue was purified by silica gel column chromatography using EtOAc/petroleum ether (1/3) to afford 600 mg (87%) of the title compound as a colorless oil. LC-MS: (ES, n/z): 317.3

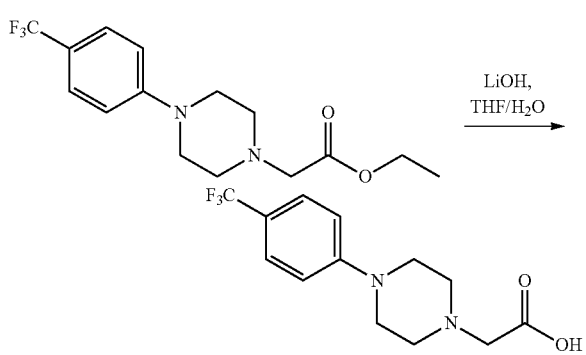

Step 2. Synthesis of 2-[4-[4-(trifluoromethyl)phenyl]piperazin-1-yl]acetic acid To a solution of the product from the previous step (600 mg, 1.90 mmol) in THF/MeOH/H$_2$O (10 mL) was added LiOH (204 mg, 8.50 mmol). The resulting solution was stirred for 2 h at RT. The pH was adjusted to 2-3 with 2N HCl. The resulting solution was extracted with EtOAc and the combined organic layers were concentrated under vacuum to afford 450 mg (82%) of the title compound as a white solid. LC-MS: (ES, m/z): 289.2

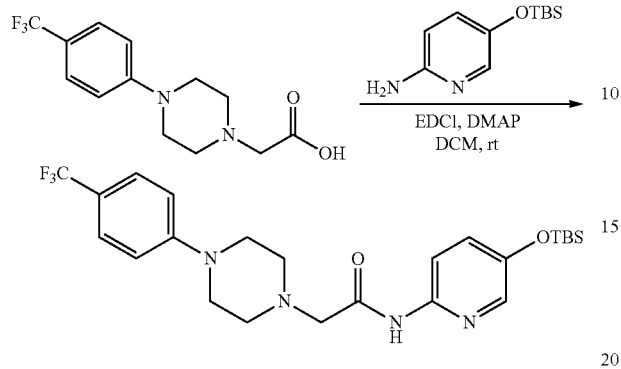

Step 3. Synthesis of N-[5-[(tert-butyldimethylsilyl)oxy]pyridin-2-yl]-2-[4-[4-(trifluoromethyl)phenyl]piperazin-1-yl]acetamide To a solution of the product from the previous step (228 mg, 0.79 mmol, 1.0) in CH$_2$Cl$_2$ (20 mL) was added 5-[(tert-butyldimethylsilyl)oxy]pyridin-2-amine (224 mg, 1.00 mmol), EDC.HCl (230 mg, 1.20 mmol), and DMAP (122 mg, 1.00 mmol). The resulting mixture was stirred for 4 h at RT, then quenched with the addition of water. The resulting solution was extracted with EtOAc and the combined organic layers were concentrated under vacuum. The residue was purified by silica gel column chromatography using EtOAc/petroleum ether (1/2) to afford 150 mg (38%) of the title compound as a white solid. LC-MS: (ES, m/z): 495.4

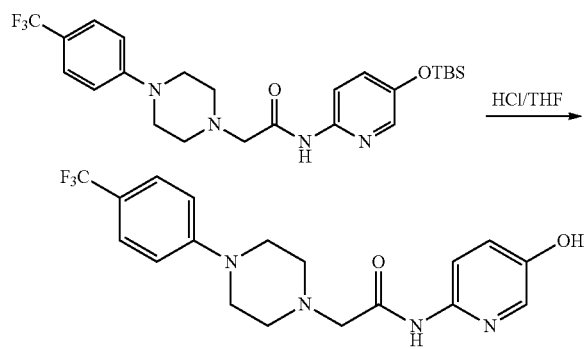

Step 4. Synthesis of N-(5-hydroxypyridin-2-yl)-2-[4-[4-(trifluoromethyl)phenyl]piperazin-1-yl]acetamide A solution of the product from the previous step (150 mg, 0.30 mmol) and 2N HCl (1 mL) in THF (2 mL) was stirred for 2 h at rt, then concentrated under vacuum. The crude product was purified by Prep-HPLC under the following conditions (2 #SHIMADZU (HPLC-01)): Column, XBridge Prep OBD C18 Column, 30??150 mm 5 um; mobile phase, Water (10 MMOL/L NH$_4$HCO$_3$) and ACN (20.0% ACN up to 49.0% in 8 min); This resulted in 72.0 mg (62%) of the title compound as a white solid.

LC-MS: (ES, n/z): 381.0

$^1$H NMR (300 MHz, DMSO-d$_6$) δ 9.75 (s, 1H), 9.70 (s, 1H), 7.96-7.80 (m, 2H), 7.48 (d, J=8.4 Hz, 2H), 7.25-7.15 (m, 1H), 7.05 (d, J=8.5 Hz, 2H), 3.35-3.30 (m, 4H), 3.19 (s, 2H), 2.67-2.64 (m, 4H).

Example 48

1-(4-fluorophenyl)-N-(5-hydroxypyridin-2-yl)piperidine-3-carboxamide

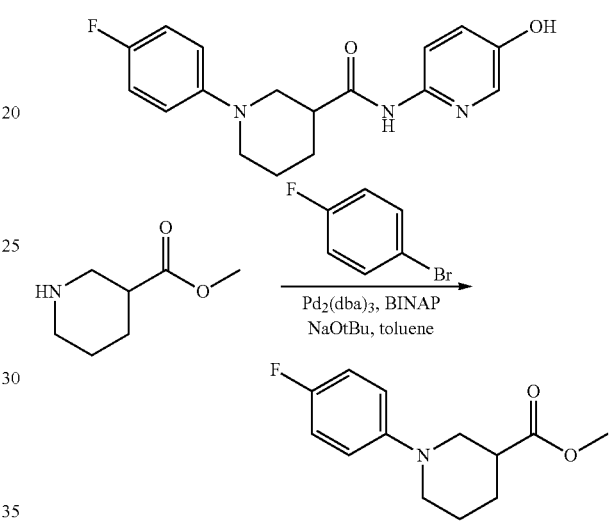

Step 1. Synthesis of methyl 1-(4-fluorophenyl)piperidine-3-carboxylate

A solution of 1-bromo-4-fluorobenzene (1 g, 5.71 mmol, 1.00 eq), methyl piperidine-3-carboxylate (820 mg, 5.73 mmol, 1.00 eq), NaOtBu (850 mg, 8.85 mmol, 1.50 eq), BINAP (0.07 g, 0.01 eq), Pd$_2$(dba)$_3$ (110 mg, 0.12 mmol, 0.01 eq) in toluene (10 mL) was stirred for 16 h at 80° C., then cooled and extracted with 2×30 mL of EtOAc. The combined organic layers were concentrated under vacuum. The residue was purified with silica gel chromatography using EtOAc/hexane (1/2) to afford 800 mg (59%) of the title compound as a yellow solid. LC-MS: (ES, m/z): 238.3

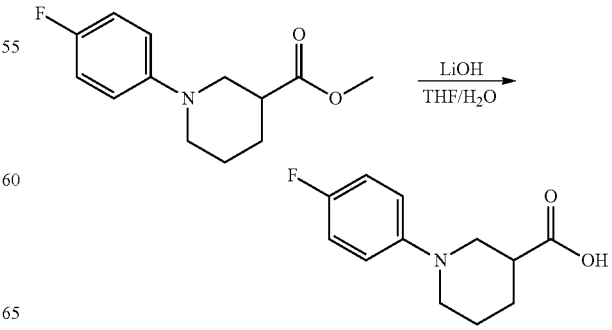

Step 2. Synthesis of 1-(4-fluorophenyl)piperidine-3-carboxylic acid

A solution of the product from the previous step (800 mg, 3.37 mmol, 1.00 eq) and LiOH (324 mg, 13.53 mmol, 4.00 eq) in THF/H₂O/MeOH (5 Ml/5 mL/5 mL) was stirred for 2 h at rt. The pH adjusted to 3 with 2 N HCl. The resulting solution was extracted with 30 mL EtOAc, and the organic layers were combined and concentrated under vacuum, affording 600 mg (80%) of the title compound as a brown solid. LC-MS: (ES, m/z): 224.3

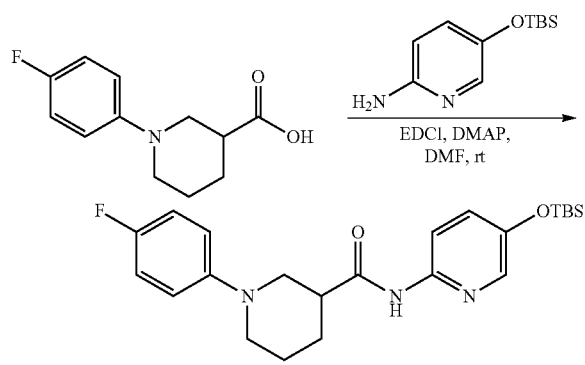

Step 3. Synthesis of N-[5-[(tert-butyldimethylsilyl)oxy]pyridin-2-yl]-1-(4-fluorophenyl)piperidine-3-carboxamide A solution of the product from the previous step (223 mg, 1.00 mmol, 1.00 eq), 5-[(tert-butyldimethylsilyl)oxy]pyridin-2-amine (224 mg, 1.00 mmol, 1.00 eq), EDCl (230 mg, 1.20 mmol, 1.20 eq), DMAP (122 g, 998.61 mmol, 1.00 eq) in CH₂Cl₂ (5 mL) was stirred for 2 h at rt. The resulting solution was extracted with 30 mL EtOAc, and the combined organic layers were concentrated under vacuum. The residue was purified with silica gel chromatography using EtOAc/hexane (1/2) to afford 200 mg (47%) of the title compound as an off-white solid. LC-MS: (ES, m/z): 430.2

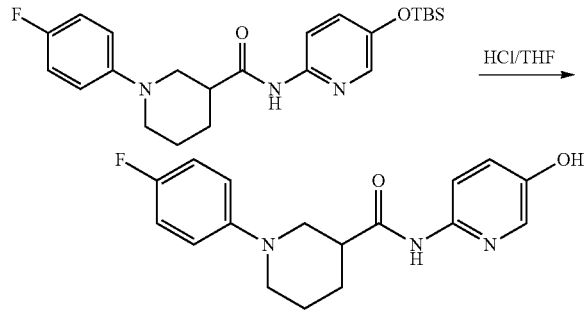

Step 4. Synthesis of 1-(4-fluorophenyl)-N-(5-hydroxypyridin-2-yl)piperidine-3-carboxamide To a solution of the product from the previous step (200 mg, 0.47 mmol, 1.00 eq) in THF (3 mL) was added 2N HCl (1 mL) dropwise with stirring. The resulting solution was stirred for 2 h at rt. The resulting mixture was concentrated under vacuum. The crude product (200 mg) was purified by Prep-HPLC with the following conditions (2 #SHIMADZU (HPLC-01)): Column, XBridge Shield RP18 OBD Column, 30×150 mm, 5 um; mobile phase, Water (10 MMOL/L NH₄HCO₃) and ACN (30.0% ACN up to 53.0% in 8 min); Detector, UV 254/220 nm. This resulted in 39.2 mg (27%) of the title compound as an off-white solid.

LC-MS: (ES, m/z): 315.9

¹H NMR (300 MHz, DMSO-d₆) δ 10.26 (s, 1H), 9.08 (s, 1H), 7.90 (d, J=8.9 Hz, 1H), 7.83 (d, J=2.9 Hz, 1H), 7.16 (dd, J=8.9, 3.0 Hz, 1H), 7.08-6.90 (m, 4H), 3.66 (d, J=7.5 Hz, 1H), 3.51 (d, J=12.1 Hz, 1H), 2.75 (d, J=7.3 Hz, 2H), 2.60 (dt, J=11.4, 6.0 Hz, 1H), 1.88 (d, J=7.7 Hz, 1H), 1.77-1.68 (m, 1H), 1.57 (d, J=9.2 Hz, 2H).

Example 49

Synthesis of 2-[1-(4-fluorophenyl) piperidin-4-yl]-N-(5-hydroxypyridin-2-yl)acetamide

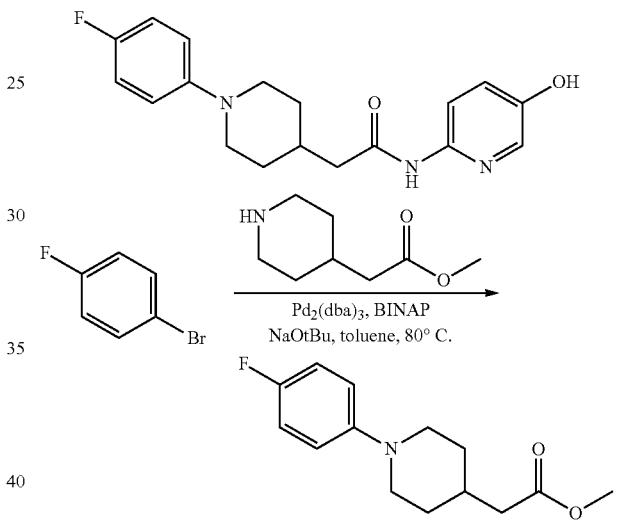

Step 1. Synthesis of methyl 2-[1-(4-fluorophenyl)piperidin-4-yl]acetate

A solution of 1-bromo-4-fluorobenzene (1 g, 5.71 mmol, 1.00 eq), methyl 2-(piperidin-4-yl)acetate (900 mg, 5.72 mmol, 1.00 eq), NaOtBu (850 mg, 8.85 mmol, 1.50 eq), BINAP (0.07 g, 0.01 eq), Pd₂(dba)₃ (110 mg, 0.12 mmol, 0.01 eq) in toluene (10 mL) was stirred for 16 h at 80° C. The resulting solution was cooled to rt and extracted with 30 mL of EtOAc. The combined organic layers combined were concentrated under vacuum. The residue was purified with silica gel chromatography using EtOAc/hexane (1/2) to afford 800 mg (56%) of the title compound as an off-white solid. LC-MS: (ES, m/z): 252

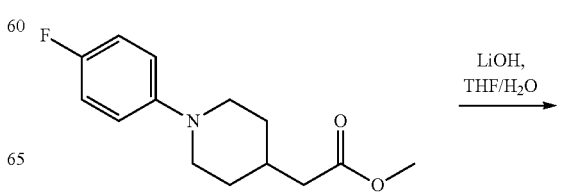

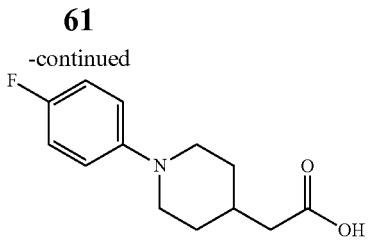

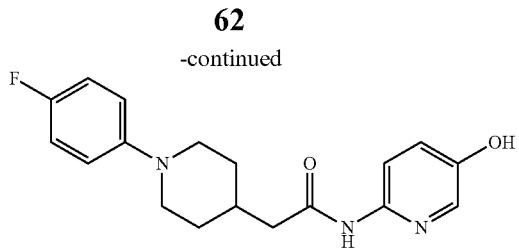

Step 2. Synthesis of 2-[1-(4-fluorophenyl)piperidin-4-yl]acetic acid

A solution of the product from the previous step (800 mg, 3.18 mmol, 1.00 eq) and LiOH (324 mg, 13.53 mmol, 4.00 eq) in THF/H$_2$O/MeOH (5 mL/5 mL/5 mL) was stirred for 2 h at rt. The pH was adjusted to 3 with 2 M HCl. The resulting solution was extracted with 2×30 mL of EtOAc and the combined organic layers were concentrated under vacuum, affording 700 mg (93%) of the title compound as an off-white solid.

LC-MS: (ES, m/z): 238

Step 4. Synthesis of 2-[1-(4-fluorophenyl) piperidin-4-yl]-N-(5-hydroxypyridin-2-yl)acetamide To a solution of the product from the previous step (200 mg, 0.45 mmol, 1.00 eq) in THF (3 mL) was added HCl (2M, 1 ml) dropwise with stirring. The resulting solution was stirred for 2 h at rt. The resulting mixture was concentrated under vacuum. The crude product (200 mg) was purified by Prep-HPLC with the following conditions (2 #SHIMADZU (HPLC-01)): Column, XBridge Prep C18 OBD Column, 30*50 mm, 5 um, 13 nm; mobile phase, Water (0.1% FA) and ACN (2.0% ACN up to 46.0% in 8 min); Detector, UV 254/220 nm. This resulted in 78.1 mg (53%) of the title compound as an off-white solid.

LC-MS: (ES, m/z): 330

$^1$H NMR (300 MHz, DMSO-d$_6$) δ 10.17 (s, 1H), 9.63 (s, 1H), 7.91 (d, J=8.9 Hz, 1H), 7.82 (d, J=2.9 Hz, 1H), 7.16 (dd, J=8.9, 3.0 Hz, 1H), 7.07-6.92 (m, 2H), 6.97-6.83 (m, 2H), 3.60-3.47 (m, 2H), 2.58 (td, J=12.1, 2.5 Hz, 2H), 2.28 (d, J=7.1 Hz, 2H), 1.85 (ddt, J=11.0, 7.4, 3.8 Hz, 1H), 1.71 (dd, J=12.8, 3.1 Hz, 2H), 1.29 (qd, J=12.1, 3.9 Hz, 2H).

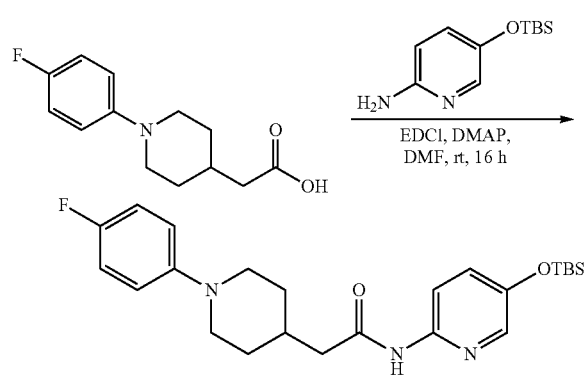

Step 3. Synthesis of N-[5-[(tert-butyldimethylsilyl)oxy]pyridin-2-yl]-2-[1-(4-fluorophenyl)piperidin-4-yl]acetamide A solution of the product from the previous step (250 mg, 1.05 mmol, 1.00 eq), 5-[(tert-butyldimethylsilyl)oxy]pyridin-2-amine (224 mg, 1.00 mmol, 1.00 eq), EDCI (230 mg, 1.20 mmol, 1.20 eq), and DMAP (122 mg, 1.00 eq) in CH$_2$Cl$_2$ (5 mL) was stirred for 2 h at r. The resulting solution was extracted with 2×30 mL of EtOAc, and the combined and organic layers combined were concentrated under vacuum. The residue was purified with silica gel chromatography using EtOAc/hexane (1/2) to afford 200 mg (43%) of the title compound as an off-white solid. LC-MS: (ES, m/z): 444.

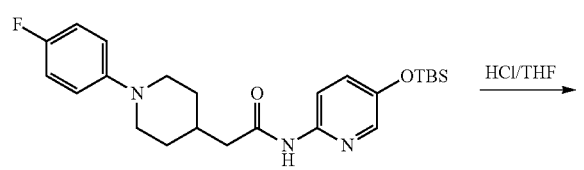

Example 50

2-[4-(4-fluorophenyl)piperazin-1-yl]-N-(5-hydroxypyridin-2-yl)acetamide

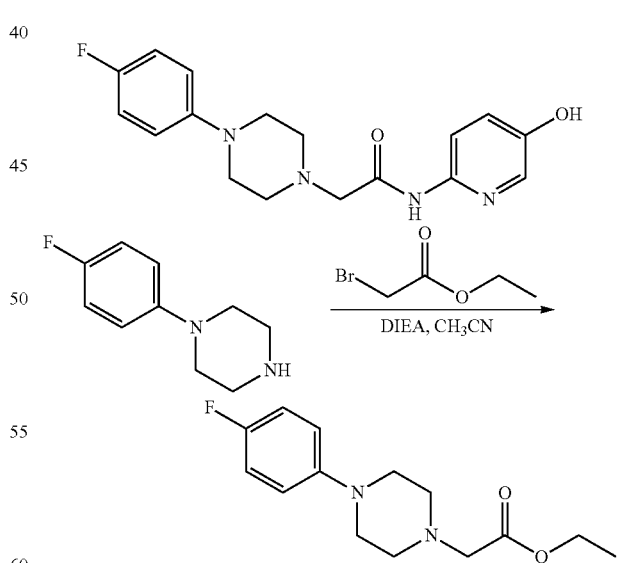

Step 1. Synthesis of ethyl 2-[4-(4-fluorophenyl)piperazin-1-yl]acetate

A solution of 1-(4-fluorophenyl)piperazine (200 mg, 1.11 mmol, 1.00 eq), DIEA (0.614 mL, 3.00 eq), ethyl 2-bromoacetate (222 mg, 1.33 mmol, 1.20 eq) in CH₃CN (5 mL) was stirred for 3 h at rt. The resulting solution was extracted with 3×20 mL of EtOAc, and the combined organic layers were dried over Na₂SO₄ and concentrated under vacuum to afford 230 mg (78%) of the title compound as a light yellow solid. LC-MS: (ES, m/z): 267.20

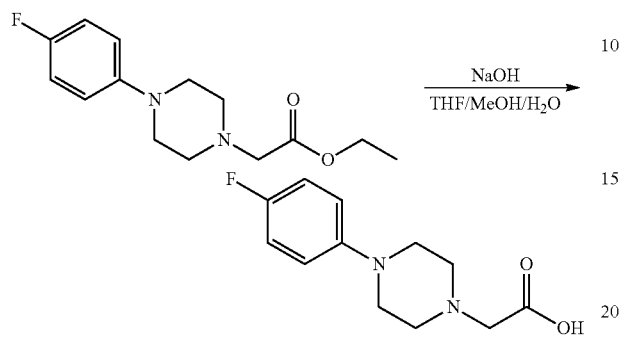

Step 2. Synthesis of 2-[4-(4-fluorophenyl)piperazin-1-yl]acetic acid

A solution of the product from the previous step (200 mg, 0.75 mmol, 1.00 eq) and NaOH (120 mg, 3.00 mmol, 4.00 eq) in THF/MeOH/H₂O (2 mL/2 mL/2 mL) was stirred for 3 h at rt. The pH was adjusted to 5 with 1 M HCl. The resulting solution was extracted with 5×20 mL of EtOAc, and the combined organic layers were dried over Na₂SO₄ and concentrated under vacuum to afford 0.1 g (56%) of the title compound as a light yellow oil. LC-MS (ES, m/z): 239.15

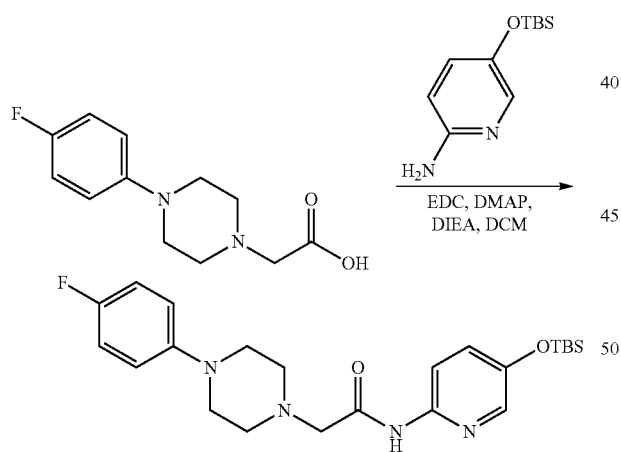

Step 3. Synthesis of N-[5-[(tert-butyldimethylsilyl)oxy]pyridin-2-yl]-2-[4-(4-fluorophenyl)piperazin-1-yl]acetamide To a solution of the product from the previous step (100 mg, 0.42 mmol, 1.00 eq), EDCI (120 mg, 0.62 mmol, 1.50 eq), and DMAP (76 mg, 0.62 mmol, 1.50 eq) in CH₂Cl₂ (5 mL) was added DIEA (0.23 mL, 3.00 eq). The resulting solution was stirred for 30 min, then 5-[(tert-butyldimethylsilyl)oxy]pyridin-2-amine (140 mg, 0.62 mmol, 1.50 eq) was added. The resulting solution was stirred for 3 h at rt.

The resulting mixture was concentrated under vacuum. The residue was purified by prep-TLC with EtOAc/petroleum ether (1/3) to afford 0.1 g (54%) of the title compound as a colorless oil. LC-MS: (ES, m/z): 445.20

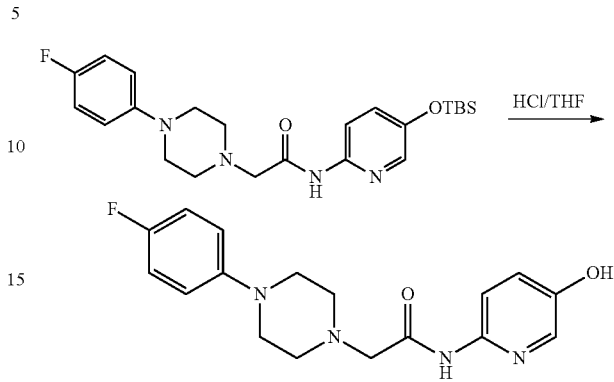

Step 4. Synthesis of 2-[4-(4-fluorophenyl)piperazin-1-yl]-N-(5-hydroxypyridin-2-yl)acetamide A solution of the product from the previous step (100 mg, 0.22 mmol, 1.00 eq) in HCl (2M, 1 mL) and THF (3 mL) was stirred for 2 h at rt. The resulting mixture was concentrated under vacuum. The crude product was purified by Prep-HPLC with the following conditions (2 #SHIMADZU (HPLC-01)): Column, Xselect CSH OBD Column 30*150 mm 5 um, n; mobile phase, Water (0.1% FA) and ACN (2.0% ACN up to 30.0% in 7 min); Detector, UV 254/220 nm. This resulted in 36.4 mg (40%) of the title compound as a white solid.

LC-MS: (ES, m/z): 331.15
¹H NMR (300 MHz, Methanol-d₄) δ 8.00 (d, J=8.9 Hz, 1H), 7.84 (dd, J=3.0, 0.7 Hz, 1H), 7.25 (dd, J=8.9, 3.0 Hz, 1H), 7.09-6.94 (m, 4H), 3.26-3.19 (m, 6H), 2.81-2.75 (m, 4H).

Example 51

2-[1-(4-chlorophenyl)piperidin-4-yl]-N-(5-hydroxypyridin-2-yl)acetamide

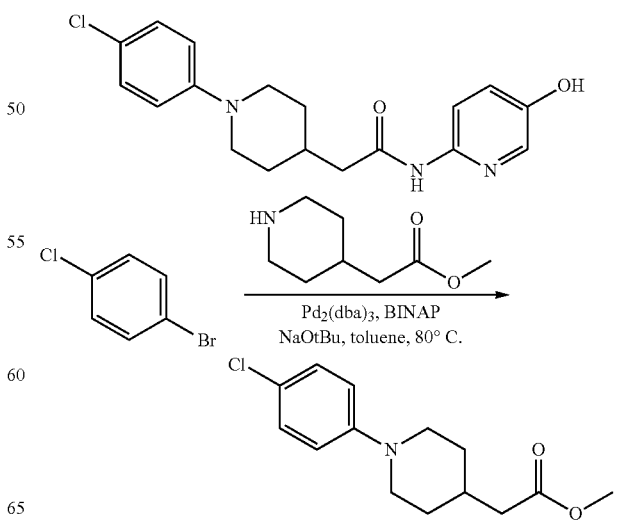

Step 1. Synthesis of methyl 2-[i-(4-chlorophenyl) piperidin-4-yl]acetate

A solution of 1-bromo-4-chlorobenzene (1 g, 5.22 mmol, 1.00 eq), methyl 2-(piperidin-4-yl)acetate (900 mg, 5.72 mmol, 1.00 eq), NaOtBu (0.85 g, 1.50 eq), BINAP (0 g, 0.01 eq), and $Pd_2(dba)_3$ (0 mg, 0.01 eq) in toluene (10 mL) was stirred for 16 h at 80° C. The resulting solution was cooled, then extracted with 2×30 mL of EtOAc. The combined organic layers were concentrated under vacuum. The residue was purified with silica gel column using EtOAc/hexane (1/2) to afford 700 mg (50%) of the title compound as a light brown solid. LC-MS: (ES, m/z): 268

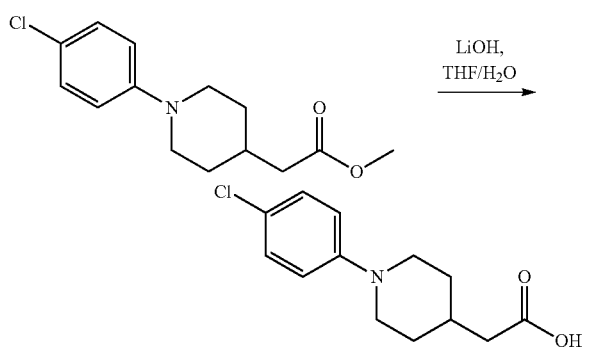

Step 2. Synthesis of 2-[1-(4-chlorophenyl)piperidin-4-yl]acetic acid

A solution of the product from the previous step (700 mg, 2.61 mmol, 1.00 eq) and LiOH (252 mg, 10.52 mmol, 2.00 eq) in $THF/H_2O/MeOH$ (5 mL/5 mL/5 mL) was stirred for 2 h at rt. The pH was adjusted to 2 with 2 M HCl. The resulting solution was extracted with 2×30 mL of EtOAc, and the combined organic layers were concentrated under vacuum to afford 400 mg (60%) of the title compound as a light yellow solid. LC-MS: (ES, m/z): 254

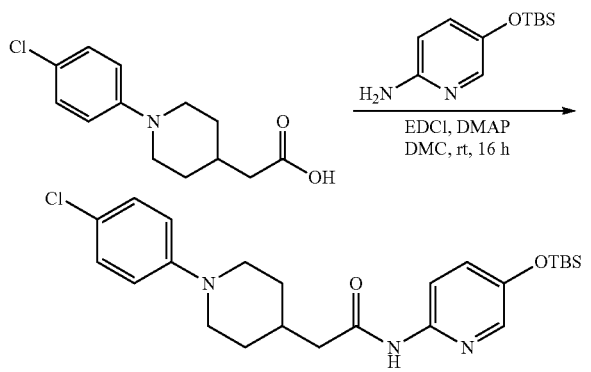

Step 3. Synthesis of N-[5-[(tert-butyldinethylsilyl) oxy]pyridin-2-yl]-2-[1-(4-chlorophenyl)piperidin-4-yl]acetamide A solution of the product from the previous step (253 mg, 1.00 mmol, 1.00 eq), 5-[(tert-butyldimethylsilyl)oxy]pyridin-2-amine (224 mg, 1.00 mmol, 1.00 eq), EDCI (230 mg, 1.20 mmol, 1.20 eq), DMAP (122 mg, 1.00 eq) in $CH_2Cl_2$ (5 mL) was stirred for 2 hr at rt. The resulting solution was extracted with 2×30 mL of $CH_2Cl_2$, and the combined organic layers were concentrated under vacuum. The residue was purified with silica gel chromatography using EtOAc/hexane (1/2) to afford 200 mg (44%) of the title compound as a light yellow solid. LC-MS: (ES, m/z): 460

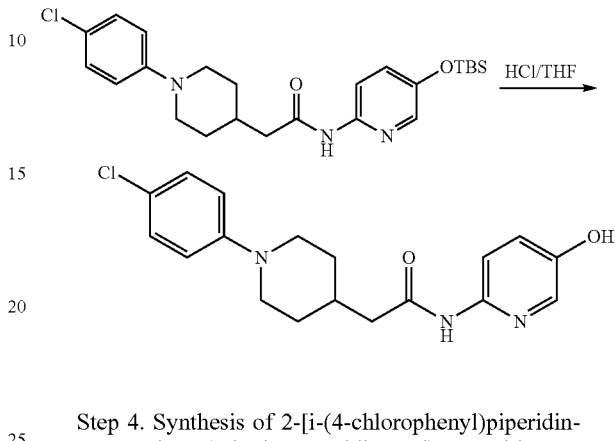

Step 4. Synthesis of 2-[i-(4-chlorophenyl)piperidin-4-yl]-N-(5-hydroxypyridin-2-yl)acetamide To a solution of the product from the previous step (200 mg, 0.43 mmol, 1.00 eq) in THF (3 mL) was added HCl (2 M, 1 mL) dropwise with stirring. The resulting solution was stirred for 2 h at rt. The resulting mixture was concentrated under vacuum. The crude product (200 mg) was purified by Prep-HPLC with the following conditions (2 #SHIMADZU (HPLC-01)): Column, XBridge Prep OBD C18 Column, 30×150 mm 5 um; mobile phase, Water (10 MMOL/L $NH_4HCO_3$) and ACN (10.0% ACN up to 77.0% in 7 min); Detector, UV 254/220 nm. This resulted in 66.9 mg (45%) of the title compound as an off-white solid.

LC-MS: (ES, m/z): 346

$^1$H NMR (300 MHz, DMSO-$d_6$) δ 10.16 (s, 1H), 9.60 (s, 1H), 7.91 (d, J=8.9 Hz, 1H), 7.81 (d, J=2.9 Hz, 1H), 7.22-7.10 (m, 3H), 6.90 (d, J=8.7 Hz, 2H), 3.63 (d, J=12.3 Hz, 2H), 2.64 (t, J=12.0 Hz, 2H), 2.27 (d, J=7.1 Hz, 2H), 1.89 (s, 1H), 1.70 (d, J=12.9 Hz, 2H), 1.26 (q, J=11.3 Hz, 2H).

Example 52

2-[4-(4-chlorophenyl)piperazin-1-yl]-N-(5-hydroxypyridin-2-yl)acetamide

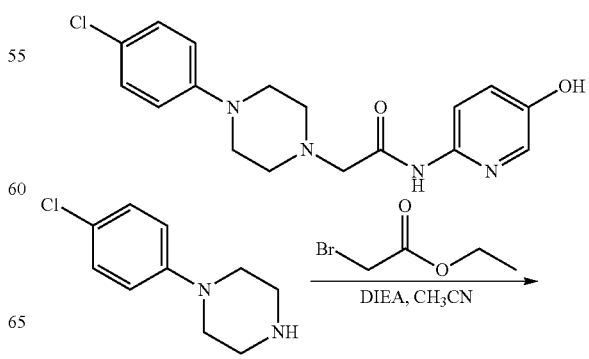

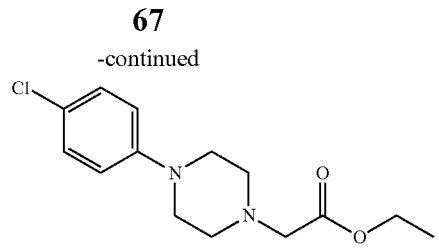

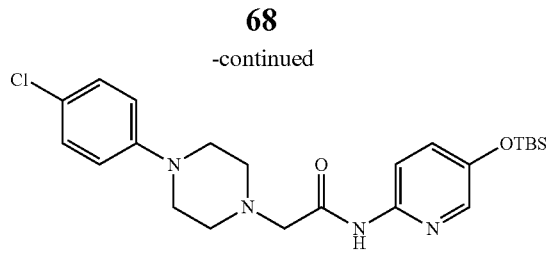

Step 1. Synthesis of ethyl 2-[4-(4-chlorophenyl)piperazin-1-yl]acetate

A solution of 1-(4-chlorophenyl)piperazine (200 mg, 1.02 mmol, 1.00 eq), DIEA (0.564 mL, 3.00 eq), and ethyl 2-bromoacetate (0.136 mL, 1.20 eq) in CH₃CN (5 mL) was stirred for 3 h at rt. The resulting solution was extracted with 3×20 mL of EtOAc, and the combined organic layers were dried over Na₂SO₄ and concentrated under vacuum, to afford 200 mg (70%) of the title compound as a light yellow solid. LC-MS: (ES, m/z): 285.1

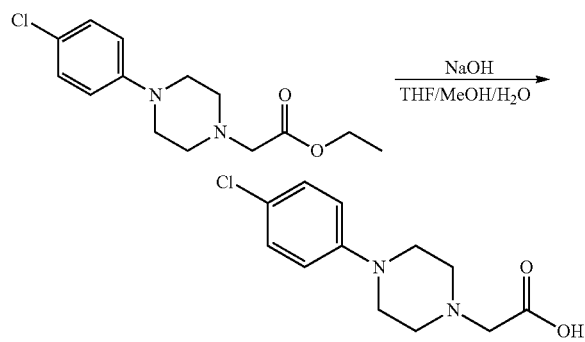

Step 2. Synthesis of 2-[4-(4-chlorophenyl)piperazin-1-yl]acetic acid

A solution of the product from the previous step (200 mg, 0.71 mmol, 1.00 eq) and NaOH (113 mg, 2.83 mmol, 4.00 eq) in THF/MeOH/H₂O (2 mL/2 mL/2 mL) was stirred for 3 h at rt. The pH was adjusted to 5 with 1 M HCl. The resulting solution was extracted with 5×20 mL of EtOAc, and the combined organic layers were dried over Na₂SO₄ and concentrated under vacuum, to afford 0.1 g (56%) of the title compound as a light yellow oil. LC-MS (ES, n/z): 255.10

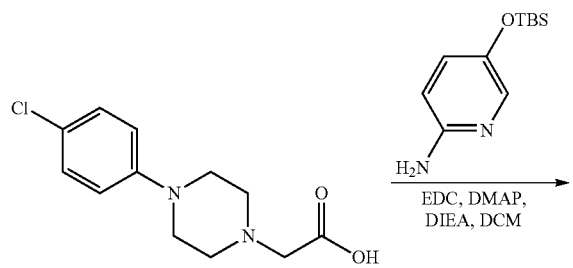

Step 3. Synthesis of N-[5-[(tert-butyldimethylsilyl)oxy]pyridin-2-yl]-2-[4-(4-chlorophenyl)piperazin-1-yl]acetamide To a solution of the product from the previous step (100 mg, 0.39 mmol, 1.00 eq), EDCI (115 mg, 0.60 mmol, 1.50 eq), and DMAP (72 mg, 0.59 mmol, 1.50 eq) in CH₂Cl₂ (5 mL) was added DIEA (0.217 mL, 3.00 eq). The resulting solution was stirred for 30 min, then 5-[(tert-butyldimethylsilyl)oxy]pyridin-2-amine (132 mg, 0.59 mmol, 1.50 eq) was added. The resulting solution was stirred for 3 h at rt. The resulting mixture was concentrated under vacuum. The residue was purified by prep-TLC with EtOAc/petroleum ether (1/3) to afford 0.1 g (55%) of the title compound as a colorless oil. LC-MS: (ES, m/z): 461.3

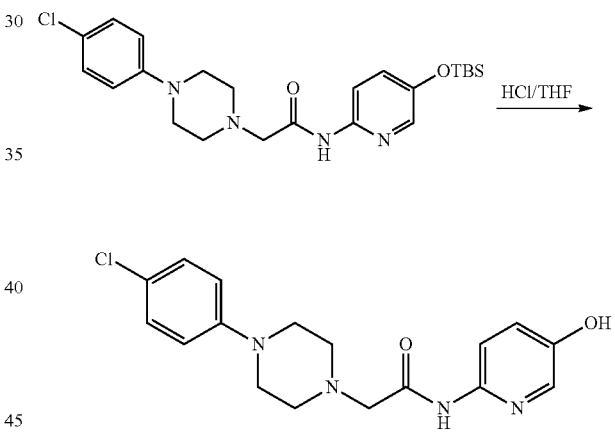

Step 4. Synthesis of 2-[4-(4-chlorophenyl)piperazin-1-yl]-N-(5-hydroxypyridin-2-yl)acetamide A solution of the product from the previous step (100 mg, 0.22 mmol, 1.00 eq) in HCl (2 M, 1 mL) and THF (3 mL) was stirred for 2 h at rt. The resulting mixture was concentrated under vacuum. The crude product (mL) was purified by Prep-HPLC with the following conditions (2 #SHIMADZU (HPLC-01)): Column, Xselect CSH OBD Column 30*150 mm 5 um, n; mobile phase, Water (0.1% FA) and ACN (2.0% ACN up to 40.0% in 8 min); Detector, UV 254/220 nm. This resulted in 30.4 mg (40%) of the title compound as a white solid.

LC-MS: (ES, m/z): 347.0

¹H NMR (300 MHz, DMSO-d₆) δ 9.72 (s, 1H), 8.12 (s, 1H), 7.91 (d, J=8.9 Hz, 1H), 7.83 (d, J=2.9 Hz, 1H), 7.20 (td, J=5.7, 2.7 Hz, 3H), 7.01-6.86 (m, 2H), 3.21-3.17 (m, 6H), 2.65 (t, J=5.0 Hz, 4H).

Example 53

N-(5-hydroxypyridin-2-yl)-1-[4-(trifluoromethyl)phenyl]piperidine-4-carboxamide

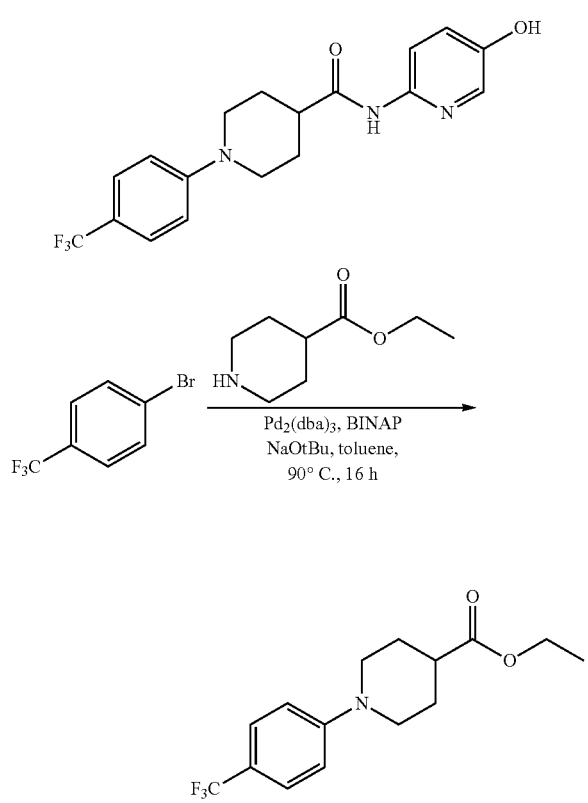

Step 1. Synthesis of ethyl 1-[4-(trifluoromethyl)phenyl]piperidine-4-carboxylate A solution of 1-bromo-4-(trifluoromethyl)benzene (1.1 g, 4.89 mmol, 1.00 eq), ethyl piperidine-4-carboxylate (770 mg, 4.90 mmol, 1.00 eq), NaOtBu (0.71 g, 1.50 eq), BINAP (0.31 g, 0.10 eq), and Pd$_2$(dba)$_3$ (450 mg, 0.49 mmol, 0.10 eq) in toluene (10 mL) was stirred for 16 h at 90° C. The resulting solution was extracted with 2×30 mL of EtOAc, and the combined organic layers were concentrated under vacuum. The residue was purified with silica gel chromatography using EtOAc/hexane (1/2) to afford 1 g (68%) of the title compound as an off-white solid. LC-MS: (ES, m/z): 302

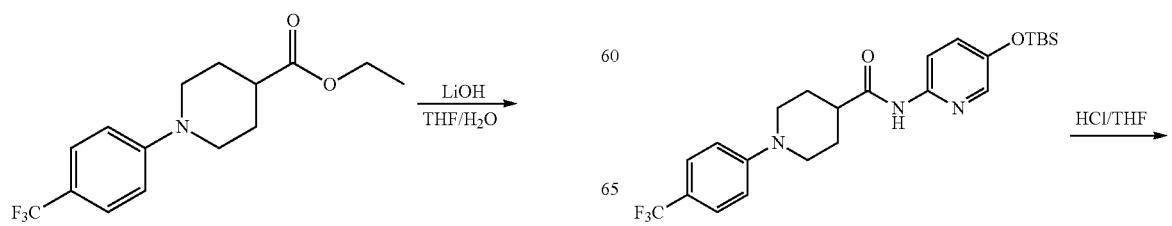

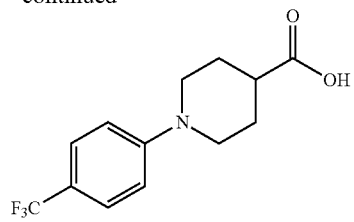

Step 2. Synthesis of 1-[4-(trifluoromethyl)phenyl]piperidine-4-carboxylic acid To a solution of the product from the previous stp (1 g, 3.32 mmol, 1.00 eq) in THF (5 mL), and H$_2$O (5 mL) was added LiOH (480 mg, 20.04 mmol, 6.00 eq). The resulting mixture was stirred for 2 h at rt, then diluted with 30 mL H$_2$O. The resulting solution was extracted with 2×30 mL of EtOAc, and the combined organic layers were concentrated under vacuum to afford 750 mg (83%) of the title compound as an off-white solid. LC-MS: (ES, m/z): 274

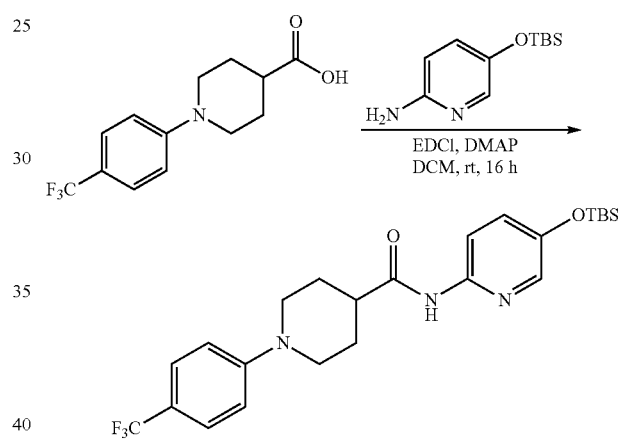

Step 3. Synthesis of N-[5-[(tert-butyldimethylsilyl)oxy]pyridin-2-yl]-1-[4-(trifluoromethyl)phenyl]piperidine-4-carboxamide A solution of the product from the previous step (200 mg, 0.73 mmol, 1.00 eq), 5-[(tert-butyldimethylsilyl)oxy]pyridin-2-amine (164 mg, 0.73 mmol, 4.00 eq), EDCI (169 mg, 0.88 mmol, 1.20 eq), and DMAP (89 mg, 1.00 eq) in CH$_2$Cl$_2$ (5 mL) was stirred for 16 h at rt. The resulting solution was extracted with 2×30 mL of CH$_2$Cl$_2$, and the combined organic layers were concentrated under vacuum. The residue was purified with silica gel chromatography using EtOAc/hexane (1/2) to afford 150 mg (43%) of the title compound as an off-white solid. LC-MS: (ES, n/z): 480

-continued

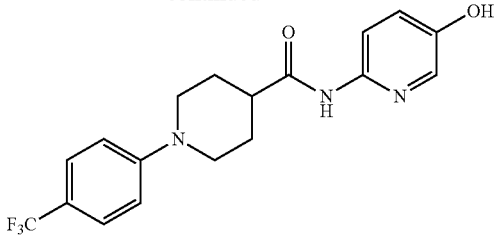

Step 4. Synthesis of N-(5-hydroxypyridin-2-yl)-1-[4-(trifluoromethyl)phenyl]piperidine-4-carboxamide To a solution of the product from the previous step (150 mg, 0.31 mmol, 1.00 eq) in THF (3 mL) was added HCl (2 M, 1 mL) dropwise with stirring. The resulting solution was stirred for 2 h at rt. The resulting mixture was concentrated under vacuum. The crude product (150 mg) was purified by Prep-HPLC with the following conditions (2 #SHIMADZU (HPLC-01)): Column, Xselect CSH OBD Column 30*150 mm 5 um, n; mobile phase, Water (10 MMOL/L NH$_4$HCO$_3$) and ACN (10.0% ACN up to 75.0% in 7 min); Detector, UV 254/220 nm. This resulted in 31.2 mg (27%) of the title compound as an off-white solid.

LC-MS: (ES, m/z): 366

$^1$H NMR (300 MHz, DMSO-d$_6$) δ 10.21 (s, 1H), 9.62 (s, 1H), 7.93-7.79 (m, 2H), 7.46 (d, J=8.6 Hz, 2H), 7.15 (dd, J=8.9, 3.0 Hz, 1H), 7.04 (d, J=8.7 Hz, 2H), 3.90 (dt, J=13.3, 3.6 Hz, 2H), 2.82 (td, J=12.5, 2.7 Hz, 2H), 2.75-2.59 (m, 1H), 1.88-1.75 (m, 2H), 1.65 (qd, J=12.2, 3.9 Hz, 2H).

Example 54

1-(4-fluorophenyl)-N-(5-hydroxypyridin-2-yl)piperidine-4-carboxamide

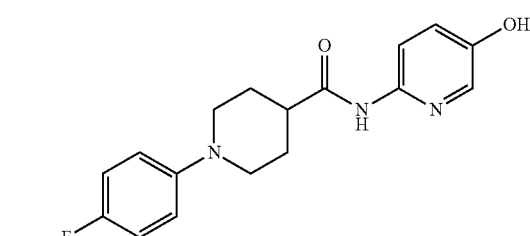

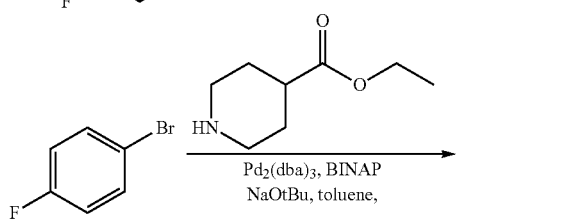

Step 1. Synthesis of ethyl 1-(4-fluorophenyl)piperidine-4-carboxylate

A solution of 1-bromo-4-fluorobenzene (1 g, 5.71 mmol, 1.00 eq), ethyl piperidine-4-carboxylate (900 mg, 9.07 mmol, 1.00 eq), NaOtBu (0.85 g, 1.50 eq), BINAP (0.07 g, 0.01 eq), and Pd$_2$(dba)$_3$ (110 mg, 0.12 mmol, 0.01 eq) in toluene (10 mL) was stirred for 16 h at 80° C. The resulting solution was cooled and extracted with 2×30 mL of EtOAc The combined organic layers were concentrated under vacuum. The residue was purified with silica gel chromatography using EtOAc/hexane (1/2) to afford 900 mg (63%) of the title compound as an off-white solid. LC-MS: (ES, m/z): 252.3

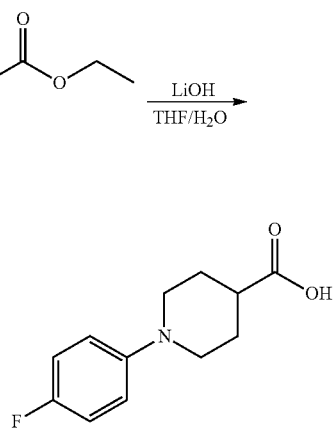

Step 2. Synthesis of 1-(4-fluorophenyl)piperidine-4-carboxylic acid

A solution of the product from the previous step (900 mg, 3.58 mmol, 1.00 eq) and LiOH (343 mg, 14.32 mmol, 4.00 eq) in THF/H$_2$O/MeOH (5 mL/5 mL/5 mL) was stirred for 2 h at rt. The pH was adjusted to 3 with 2 M HCl. The resulting solution was extracted with 2×30 mL of EtOAc, and the combined organic layers ere concentrated under vacuum, to afford 700 mg (88%) of the title compound as an off-white solid. LC-MS: (ES, m/z): 224.3

Step 3. Synthesis of N-[5-[(tert-butyldimethylsilyl)oxy]pyridin-2-yl]-1-(4-fluorophenyl)piperidine-4-carboxamide A solution of the product from the previous step (223 mg, 1.00 mmol, 1.00 eq), 5-[(tert-butyldimethylsilyl)oxy]pyridin-2-amine (224 mg, 1.00 mmol, 1.00 eq), EDCI (230 mg, 1.20 mmol, 1.20 eq), and DMAP (122 mg, 1.00 mmol, 1.00 eq) in CH$_2$Cl$_2$ (5 mL) was stirred for 2 h at rt. The resulting solution was extracted with 2×30 mL of CH$_2$Cl$_2$, and the combined organic layers were concentrated under vacuum. The residue was purified with silica gel chromatography using EtOAc/hexane (1/2) to afford 200 mg (47%) of the title compound as an off-white solid. LC-MS: (ES, m/z): 430.3

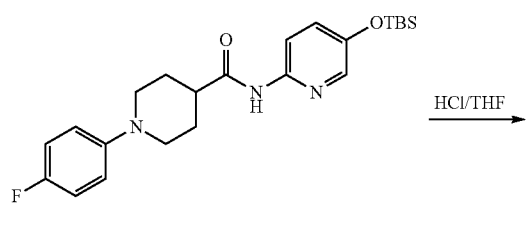

Step 4. Synthesis of 1-(4-fluorophenyl)-N-(5-hydroxypyridin-2-yl)piperidine-4-carboxamide To a solution of the product from the previous step (200 mg, 0.47 mmol, 1.00 eq) in THF (3 mL) was added 2N HCl (1 mL) dropwise with stirring. The resulting solution was stirred for 2 h at rt. The resulting mixture was concentrated under vacuum. The crude product (200 mg) was purified by Prep-HPLC with the following conditions (2 #SHIMADZU (HPLC-01)): Column, XBridge Prep OBD C18 Column, 30×150 mm 5 um; mobile phase, Water (10 MMOL/L NH$_4$HCO$_3$) and ACN (25.0% ACN up to 55.0% in 8 min); Detector, UV 254/220 nm. This resulted in 59.6 mg (41%) of the title compound as an off-white solid.

LC-MS: (ES, m/z): 315.9

$^1$H NMR (300 MHz, DMSO-d$_6$) δ 10.18 (s, 1H), 9.61 (s, 1H), 7.90 (d, J=8.9 Hz, 1H), 7.83 (d, J=2.9 Hz, 1H), 7.16 (dd, J=8.9, 3.0 Hz, 1H), 7.09-6.88 (m, 4H), 3.62 (dt, J=12.4, 3.4 Hz, 2H), 2.68-2.49 (m, 3H), 1.74 (dtd, J=36.4, 12.8, 3.6 Hz, 4H).

Example 55

2-[4-(5-fluoropyridin-2-yl)piperazin-1-yl]-N-(5-hydroxypyridin-2-yl)acetamide

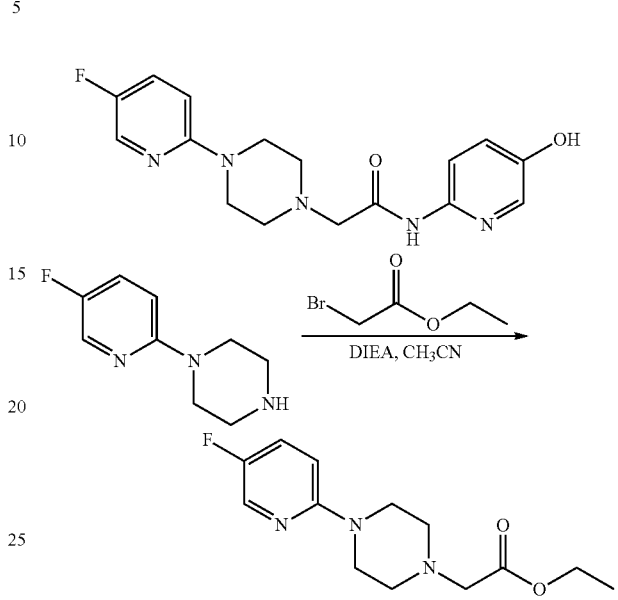

Step 1. Synthesis of ethyl 2-[4-(5-fluoropyridin-2-yl)piperazin-1-yl]acetate A solution of 1-(5-fluoropyridin-2-yl)piperazine (200 mg, 1.10 mmol, 1.00 eq), ethyl 2-bromoacetate (220 mg, 1.32 mmol, 1.20 eq), and DIEA (427 mg, 3.30 mmol, 3.00 eq) in CH$_3$CN (10 mL) was stirred for 2 h at rt. The resulting mixture was concentrated under vacuum to afford 200 mg (68%) of the title compound as a light yellow oil. LC-MS: (ES, m/z): 268.25

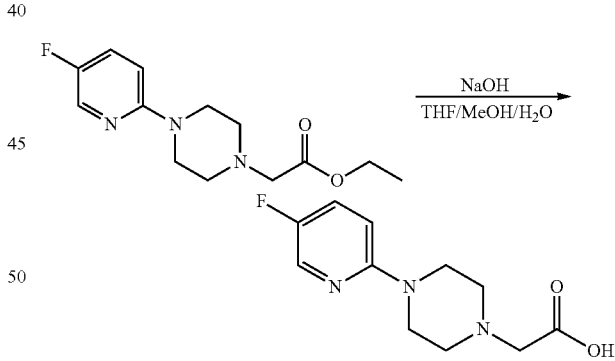

Step 2. Synthesis of 2-[4-(5-fluoropyridin-2-yl)piperazin-1-yl]acetic acid

A solution of the product from the previous step (200 mg, 0.75 mmol, 1.00 eq) and NaOH (120 mg, 3.00 mmol, 4.00 eq) in THF/MeOH/H$_2$O (4 mL/4 mL/2 mL) was stirred for 2 h at rt. The pH value was adjusted to 5 with 1 M HCl. The resulting mixture was concentrated under vacuum. The residue was taken up in DCM (30 mL) and filtered. The filtrate was concentrated under vacuum to afford 100 mg (56%) of the title compound as a colorless oil. LC-MS (ES, m/z): 240.20

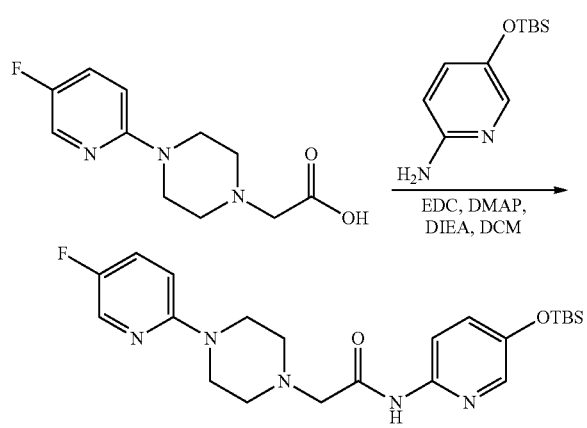

Step 3. Synthesis of N-[5-[(tert-butyldimethylsilyl)oxy]pyridin-2-yl]-2-[4-(5-fluoropyridin-2-yl)piperazin-1-yl]acetamide To a solution of the product from the previous step (100 mg, 0.42 mmol, 1.00 eq), EDCI (120 mg, 0.62 mmol, 1.50 eq), and DMAP (61 mg, 0.50 mmol, 1.20 eq) in CH$_2$Cl$_2$ (10 mL) was added DIEA (0.231 mL, 3.00 eq). The resulting solution was stirred for 30 min, then 5-[(tert-butyldimethylsilyl)oxy]pyridin-2-amine (113 mg, 0.50 mmol, 1.20 eq) was added. The resulting solution was stirred for 3 h at rt. The resulting solution was extracted with 3×30 mL of CH$_2$Cl$_2$, and the combined organic layers were dried over Na$_2$SO$_4$ and concentrated under vacuum. The residue was purified by prep-TLC with EtOAc/petroleum ether (1/1) to afford 140 mg (75%) of the title compound as a colorless oil. LC-MS: (ES, m/z): 446.35

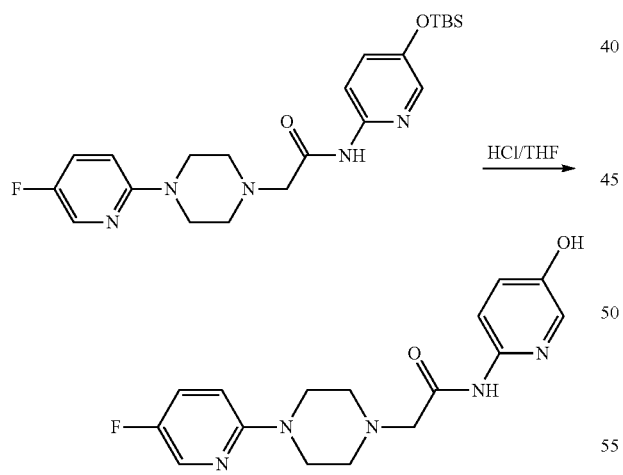

Step 4. Synthesis of 2-[4-(5-fluoropyridin-2-yl)piperazin-1-yl]-N-(5-hydroxypyridin-2-yl)acetamide A solution of the product from the previous step (140 mg, 0.31 mmol, 1.00 eq) in 2N HCl (2 mL) and THF (6 mL) was stirred for 2 h at rt. The resulting mixture was concentrated under vacuum. The crude product was purified by Prep-HPLC under the following conditions (2 #SHIMADZU (HPLC-01)): Column, XBridge Prep OBD C18 Column, 30×150 mm 5 um; mobile phase, Water (0.05% NH$_3$H$_2$O) and ACN (14.0% ACN up to 30.0% in 7 min); Detector, UV 254; 220 nm. This resulted in 31.2 mg (30%) of the title compound as an off-white solid.

LC-MS: (ES, m/z): 332.0

$^1$H NMR (300 MHz, Methanol-d$_4$) δ 8.05-7.95 (m, 2H), 7.89-7.82 (m, 1H), 7.42 (ddd, J=9.3, 8.0, 3.1 Hz, 1H), 7.27 (dd, J=8.9, 3.0 Hz, 1H), 6.87 (dd, J=9.3, 3.4 Hz, 1H), 3.64-3.57 (m, 4H), 3.25 (s, 2H), 2.79-2.71 (m, 4H).

Example 56

2-[1-(5-fluoropyridin-2-yl)piperidin-4-yl]-N-(5-hydroxypyridin-2-yl) acetamide

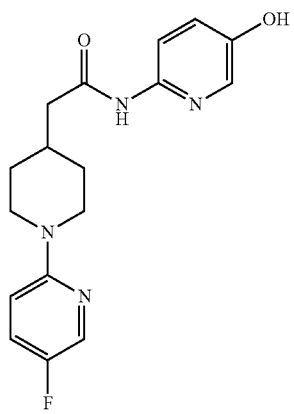

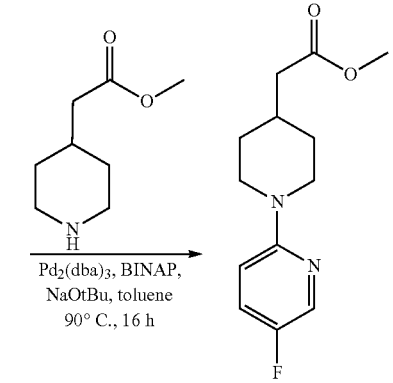

Step 1: Synthesis of methyl 2-[1-(5-fluoropyridin-2-yl)piperidin-4-yl]acetate A solution of 2-bromo-5-fluoropyridine (2 g, 11.36 mmol), methyl 2-(piperidin-4-yl)acetate (2.2 g, 13.99 mmol), NaOtBu (3.3 g), BINAP (0.36 g), and Pd$_2$(dba)$_3$ (520 mg, 0.57 mmol) in toluene (20 mL) was stirred for 16 h at 90° C. The resulting solution was extracted with 2×50 mL of EtOAc, and the combined organic layers combined were concentrated under vacuum and purified with silica gel chromatography using EtOAc/hexane (1/1) to afford 1.6 g (56%) of the title compound as an off-white solid.

LC-MS (ES, m/z): 252.8

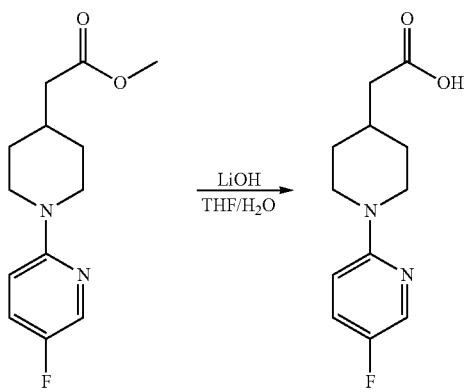 [SMILES: COC(=O)CC1CCN(c2ccc(F)cn2)CC1 ; "LiOH" ; O=C(O)CC1CCN(c2ccc(F)cn2)CC1]

Step 2: Synthesis of 2-[1-(5-fluoropyridin-2-yl)piperidin-4-yl]acetic acid

A solution of the product from the previous step (1 g, 3.96 mmol) and LiOH (570 mg, 23.80 mmol) in THF/H$_2$O (10 mL) was stirred for 4 h at room temperature. The pH was then adjusted to 3 with 2N HCl. The resulting mixture was concentrated under vacuum, and purified with silica gel chromatography using EtOAc/hexane (1/1) to afford 600 mg (64%) of the title compound as an off-white solid.

LC-MS (ES, m/z): 238.9

$^1$H NMR (300 MHz, DMSO-d$_6$) δ 12.05 (s, 1H), 8.04 (d, J=3.1 Hz, 1H), 7.44 (ddd, J=9.3, 8.3, 3.2 Hz, 1H), 6.82 (dd, J=9.4, 3.4 Hz, 1H), 4.22-4.08 (m, 2H), 2.74 (td, J=12.7, 2.6 Hz, 2H), 2.15 (d, J=7.0 Hz, 2H), 1.85 (dqt, J=10.8, 7.1, 3.6 Hz, 1H), 1.76-1.63 (m, 2H), 1.24-1.04 (m, 2H).

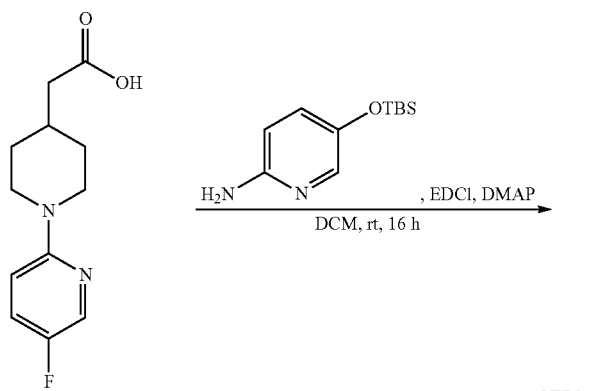

Step 3: Synthesis of N-[5-[(tert-butyldimethylsilyl)oxy]pyridin-2-yl]-2-[1-(5-fluoropyridin-2-yl)piperidin-4-yl]acetamide A solution of the product from the previous step (238 mg, 1.00 mmol), 5-[(tert-butyldimethylsilyl)oxy]pyridin-2-amine (224 mg, 1.00 mmol), EDCI (230 mg, 1.20 mmol), and DMAP (122 mg), in CH$_2$Cl$_2$ (5 mL) was stirred for 16 h at room temperature. The resulting solution was extracted with 2×30 mL EtOAc, and the combined organic layers were concentrated under vacuum and purified with silica gel chromatography using EtOAc/hexane (1/1) to afford 200 mg (45%) of the title compound as an off-white solid.

LC-MS (ES, m/z): 445.4

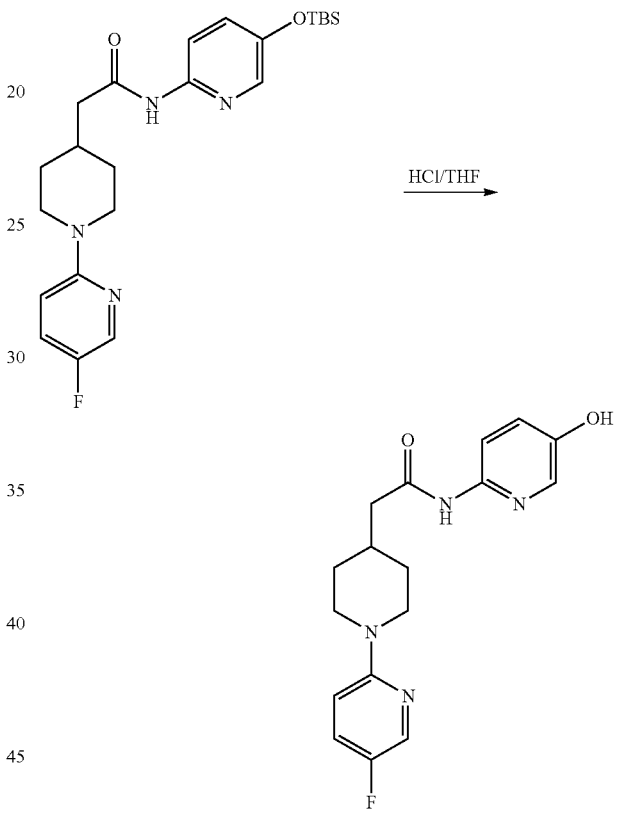

Step 4: Synthesis of 2-[1-(5-fluoropyridin-2-yl)piperidin-4-yl]-N-(5-hydroxypyridin-2-yl) acetamide To a solution of the product from the previous step (200 mg, 0.45 mmol) in THF (4 mL) was added 2 N aq. HCl (2 mL) dropwise with stirring. The resulting solution was stirred for 2 h at room temperature then concentrated under vacuum. The crude product (200 mg) was purified by Prep-HPLC under the following conditions (2 #SHIMADZU (HPLC-01)): Column, XBridge Prep OBD C18 Column, 30×150 mm 5 um; mobile phase, Water (10 MMOL/L NH$_4$HCO$_3$) and ACN (28.0% ACN up to 48.0% in 8 min); Detector, UV 254/220 nm, to afford 113 mg (76%) of the title compound as an off-white solid.

LC-MS (ES, m/z): 331.0

$^1$H NMR (300 MHz, DMSO-d$_6$) δ 10.13 (s, 1H), 9.35 (s, 1H), 8.04 (d, J=3.1 Hz, 1H), 7.90 (d, J=8.9 Hz, 1H), 7.81 (d, J=3.0 Hz, 1H), 7.43 (td, J=8.8, 3.2 Hz, 1H), 7.15 (dd, J=8.9, 3.0 Hz, 1H), 6.82 (dd, J=9.3, 3.4 Hz, 1H), 4.14 (d, J=12.5 Hz, 2H), 2.83-2.68 (m, 2H), 2.26 (d, J=7.1 Hz, 2H), 2.09-1.89 (m, 1H), 1.74-1.62 (m, 2H), 1.17 (qd, J=12.2, 3.9 Hz, 2H).

Example 57

2-[1-(5-chloropyridin-2-yl)piperidin-4-yl]-N-(5-hydroxypyridin-2-yl) acetamide

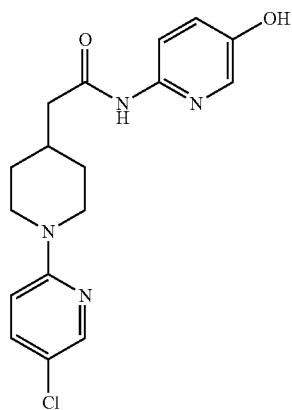

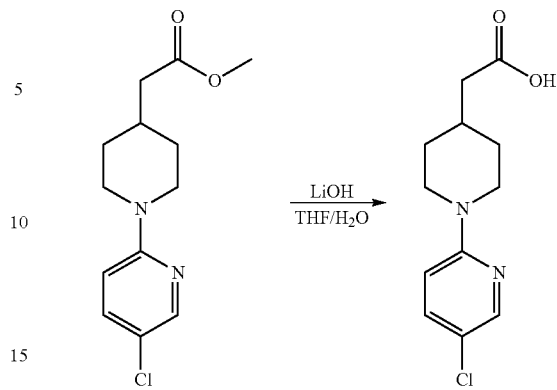

Step 2: Synthesis of 2-[1-(5-chloropyridin-2-yl)piperidin-4-yl]acetic acid

A solution of the product from the previous step (700 mg, 2.60 mmol) and LiOH (376 mg, 15.70 mmol) in THF/H₂O (10 mL) was stirred for 4 h at room temperature. The pH was adjusted to 3 with 2N HCL. The resulting solution was extracted with 5×30 mL of EtOAc, and the combined organic layers were concentrated under vacuum and purified with silica gel chromatography using EtOAc/hexane (1/1) to afford 300 mg (45%) of the title compound as an off-white solid.

LC-MS (ES, m/z): 254.8

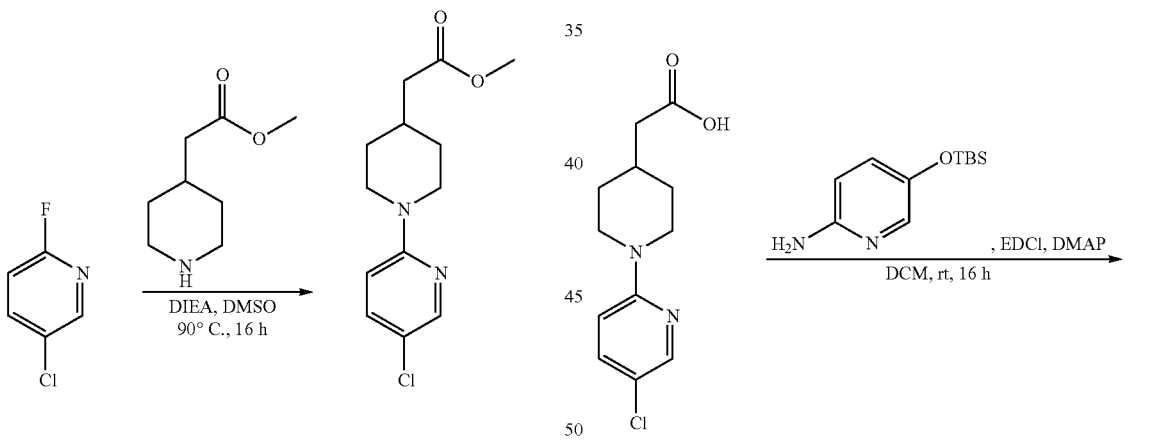

Step 1: Synthesis of methyl 2-[1-(5-chloropyridin-2-yl) piperidin-4-yl]acetate

A solution of 5-chloro-2-fluoropyridine (500 mg, 3.80 mmol), DIEA (1.5 g, 11.61 mmol), methyl 2-(piperidin-4-yl)acetate (599 mg, 3.81 mmol) in DMSO (10 mL) was stirred for 16 h at 90° C. under N₂. The resulting solution was extracted with 2×50 mL of EtOAc, and the combined organic layers were concentrated under vacuum and purified with silica gel chromatography using EtOAc/hexane (1/1) to afford 700 mg (69%) of the title compound as an off-white solid.

LC-MS (ES, m/z): 268.9

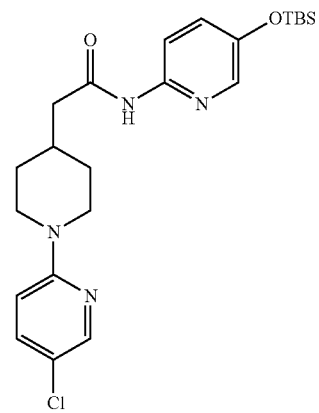

Step 3: Synthesis of N-[5-[(tert-butyldimethylsilyl)oxy]pyridine-2-yl]-2-[1-(5-chloropyridin-2-yl)piperidin-4-yl]acetamide A solution of the product from the previous step (254 mg, 1.00 mmol), 5-[(tert-butyldimethylsilyl) oxy]pyridin-2-amine (224 mg, 1.00 mmol), EDCI (230 mg, 1.20 mmol), and DMAP (122 mg) in CH₂Cl₂ (5 mL) was stirred for 16 h at room temperature. The resulting solution was extracted with 2×30 mL EtOAc and the combined organic layers were concentrated under vacuum and purified with silica gel chromatography using EtOAc/hexane (1/1) to afford 80 mg (17%) of the title compound as an off-white solid.

LC-MS (ES, m/z): 461

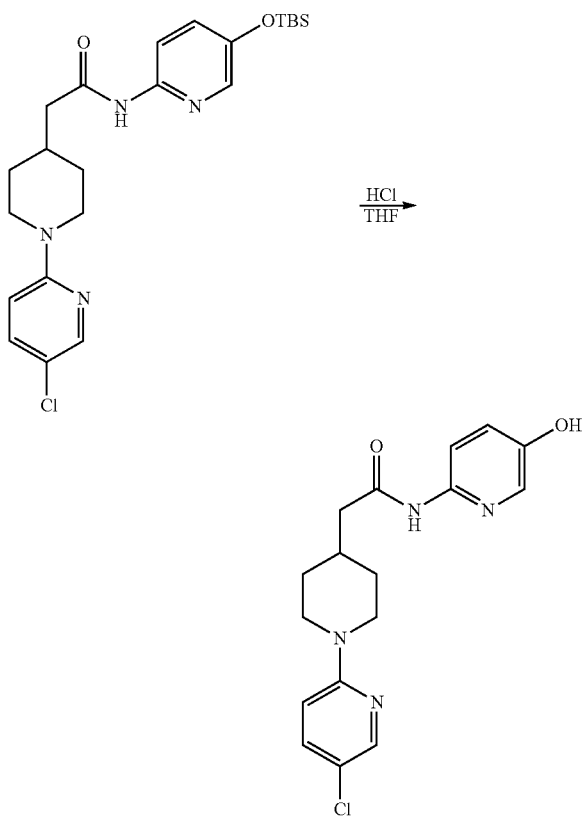

Step 4: Synthesis of 2-[1-(5-chloropyridin-2-yl)piperidin-4-yl]-N-(5-hydroxypyridin-2-yl) acetamide To a solution of the product from the previous step (80 mg, 0.17 mmol) in THF (4 mL) was added 2N HCl (2 mL) dropwise with stirring. The resulting solution was stirred for 2 h at room temperature, then concentrated under vacuum. The crude product (80 mg) was purified by Prep-HPLC with the following conditions (2 #SHIMADZU (HPLC-01)): Column, XBridge Prep OBD C18 Column, 30??150 mm 5 um; mobile phase, Water (10 MMOL/L NH₄HCO₃) and ACN (30.0% ACN up to 54.0% in 8 min); Detector, UV 254/220 nm, to afford 23.9 mg (40%) of the title compound as an off-white solid.

LC-MS (ES, m/z): 347.0

¹H NMR (300 MHz, DMSO-d₆) δ 10.12 (s, 1H), 9.54 (s, 1H), 8.05 (d, J=2.7 Hz, 1H), 7.90 (d, J=8.9 Hz, 1H), 7.81 (d, J=3.0 Hz, 1H), 7.52 (dd, J=9.1, 2.8 Hz, 1H), 7.15 (dd, J=8.9, 2.9 Hz, 1H), 6.83 (d, J=9.3 Hz, 1H), 4.20 (d, J=13.1 Hz, 2H), 2.80 (t, J=12.4 Hz, 2H), 2.26 (d, J=7.1 Hz, 2H), 2.00 (s, 1H), 1.74-1.62 (m, 2H), 1.15 (td, J=13.6, 13.2, 6.8 Hz, 2H).

Example 58

N-(5-hydroxypyridin-2-yl)-biphenyl-2-carboxamide

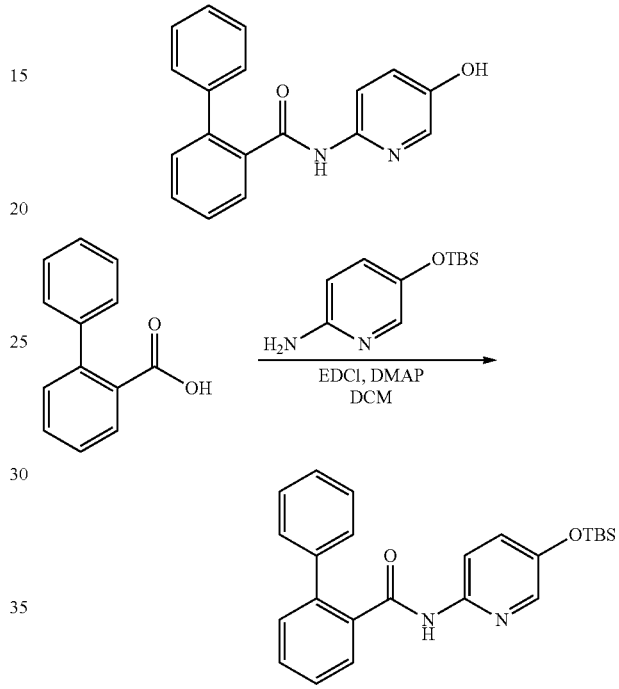

Step 1: Synthesis of N-[5-[(tert-butyldimethylsilyl)oxy]pyridin-2-yl]-biphenyl-2-carboxamide A solution of biphenyl-2-carboxylic acid (198 mg, 1.00 mmol), 5-[(tert-butyldimethylsilyl)oxy]pyridin-2-amine (224 mg, 1.00 mmol), EDCI (230 mg, 1.20 mmol), and DMAP (122 mg), in CH₂Cl₂ (5 mL) was stirred for 16 h at room temperature, then diluted with H₂O and extracted with 2×20 mL of CH₂Cl₂ The combined organic layers were dried over Na₂SO₄, concentrated under vacuum, and purified with prep-TLC using EtOAc/hexane (1/2) to afford 200 mg (49%) of the title compound as a light yellow solid.

LC-MS (ES, m/z): 405.35

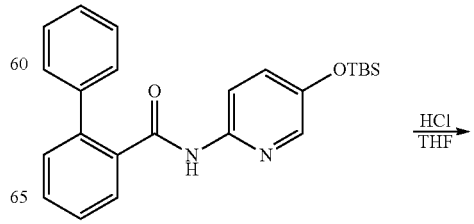

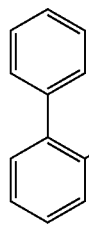

Step 2: Synthesis of N-(5-hydroxypyridin-2-yl)-biphenyl-2-carboxamide

A solution of the product from the previous step (200 mg, 0.49 mmol, 1.00 equiv) in 2 M aq HCl (2 mL) and THF (4 mL) was stirred for 2 h at room temperature, then concentrated under vacuum. The crude product (200 mg) was purified by Prep-HPLC with the following conditions (2 #SHIMADZU (HPLC-01)): Column, XBridge Prep OBD C18 Column, 30×150 mm 5 um; mobile phase, water (10 MMOL/L NH$_4$HCO$_3$) and ACN (10.0% ACN up to 67.0% in 8 min); Detector, UV 254/220 nm, to afford 81.3 mg (57%) of the title compound as an off-white solid.

LC-MS: (ES, m/z): 290.9

$^1$H NMR (300 MHz, DMSO-d$_6$) δ 10.38 (s, 1H), 9.65 (s, 1H), 7.78 (d, J=7.4 Hz, 2H), 7.64-7.03 (m, 10H).

Example 59

Synthesis of N-(5-hydroxypyridin-2-yl)-biphenyl-3-carboxamide

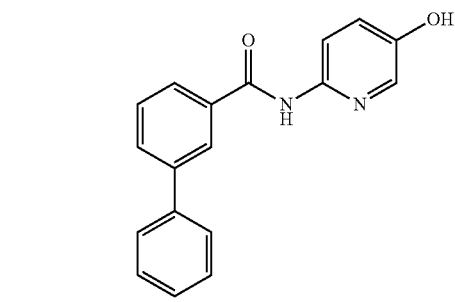

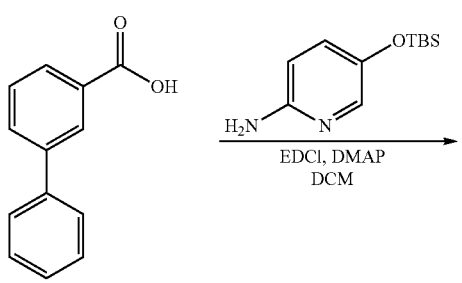

Step 1: Synthesis of N-[5-[(tert-butyldimethylsilyl)oxy]pyridin-2-yl]-biphenyl-3-carboxamide A solution of biphenyl-3-carboxylic acid (198 mg, 1.00 mmol), 5-[(tert-butyldimethylsilyl)oxy]pyridin-2-amine (224 mg, 1.00 mmol), EDCI (230 mg, 1.20 mmol), and DMAP (122 mg, 1.00 mmol) in CH$_2$Cl$_2$ (5 ml) was stirred for 16 h at room temperature, then diluted with H$_2$O and extracted with 2×20 mL of EtOAc. The combined organic layers were dried over Na$_2$SO$_4$, concentrated under vacuum, and purified with prep-TLC using EtOAc/hexane (1/2) to afford 250 mg (61%) of the title compound as a light yellow solid.

LC-MS (ES, m/z): 405.35

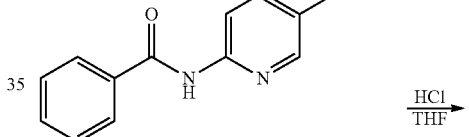

Step 2: Synthesis of N-(5-hydroxypyridin-2-yl)-biphenyl-3-carboxamide

To a solution of the product from the previous step (250 mg, 0.62 mmol) in THF (4 mL) was added of 2 N aq. HCl (2 mL) dropwise with stirring. The resulting solution was stirred for 2 h at room temperature, then concentrated under vacuum. The crude product (250 mg) was purified by Prep-HPLC with the following conditions (2 #SHIMADZU (HPLC-01)): Column, XBridge Prep OBD C18 Column, 30×150 mm 5 um; mobile phase, water (10 MMOL/L NH$_4$HCO$_3$) and ACN (10.0% ACN up to 74.0% in 8 min);

Detector, UV 254/220 nm, to afford 149.4 mg (83%) of the title compound as an off-white solid.
LC-MS (ES, m/z): 291.0
$^1$H NMR (300 MHz, DMSO-d$_6$) δ 10.75 (s, 1H), 9.71 (s, 1H), 8.31 (t, J=1.9 Hz, 1H), 8.11-7.90 (m, 3H), 7.90-7.67 (m, 3H), 7.48 (tt, J=30.0, 7.5 Hz, 4H), 7.26 (dd, J=8.9, 3.0 Hz, 1H).
The following compounds can generally be made using the methods known in the art and described above. It is expected that these compounds when made will have activity in the assays described below.
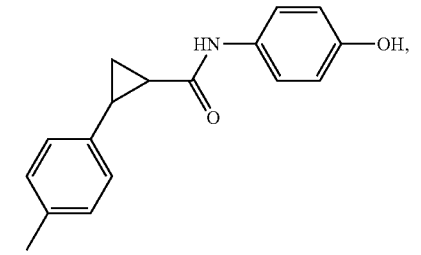
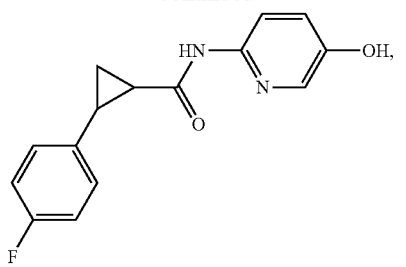
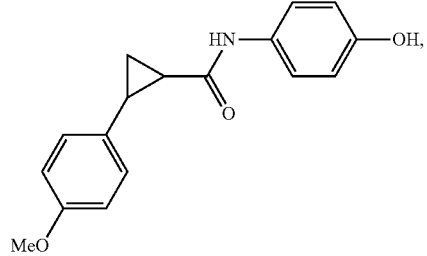
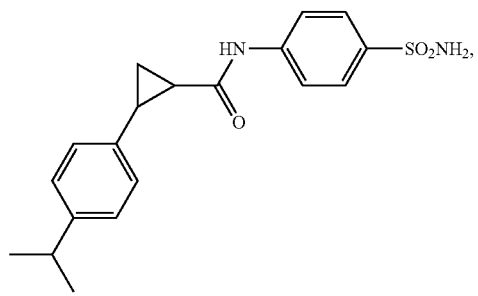
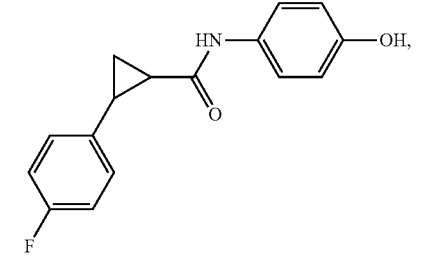
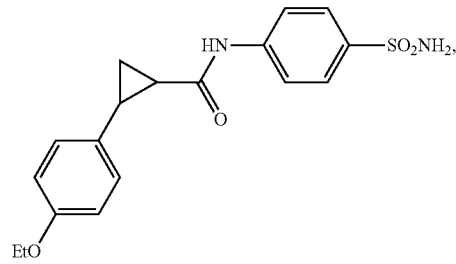
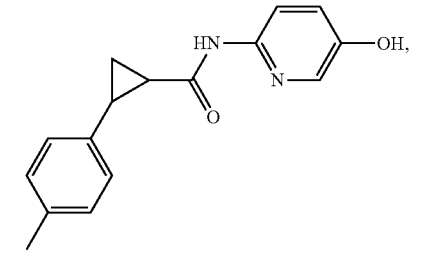
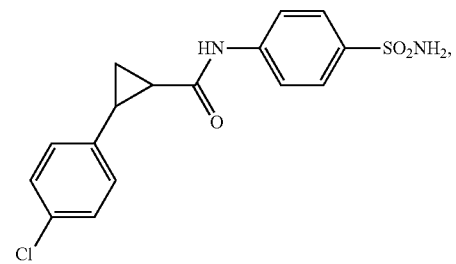
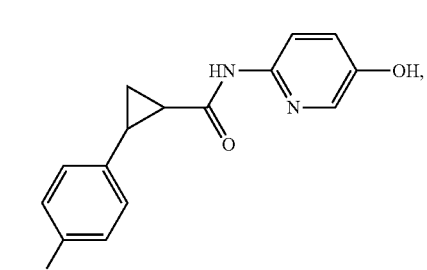
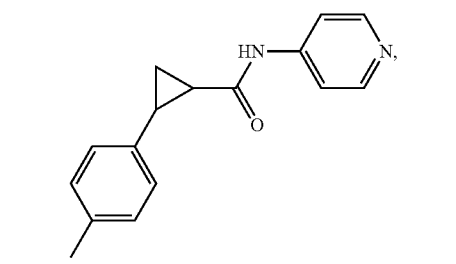
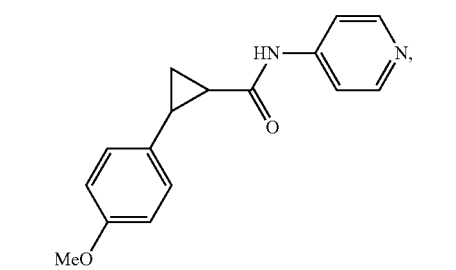

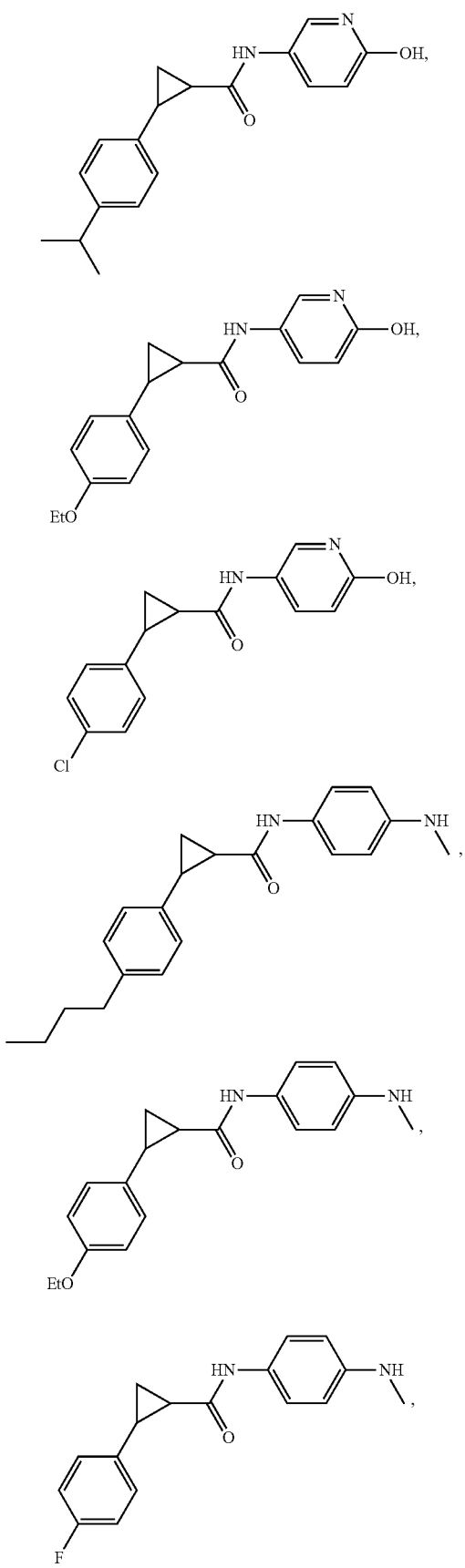
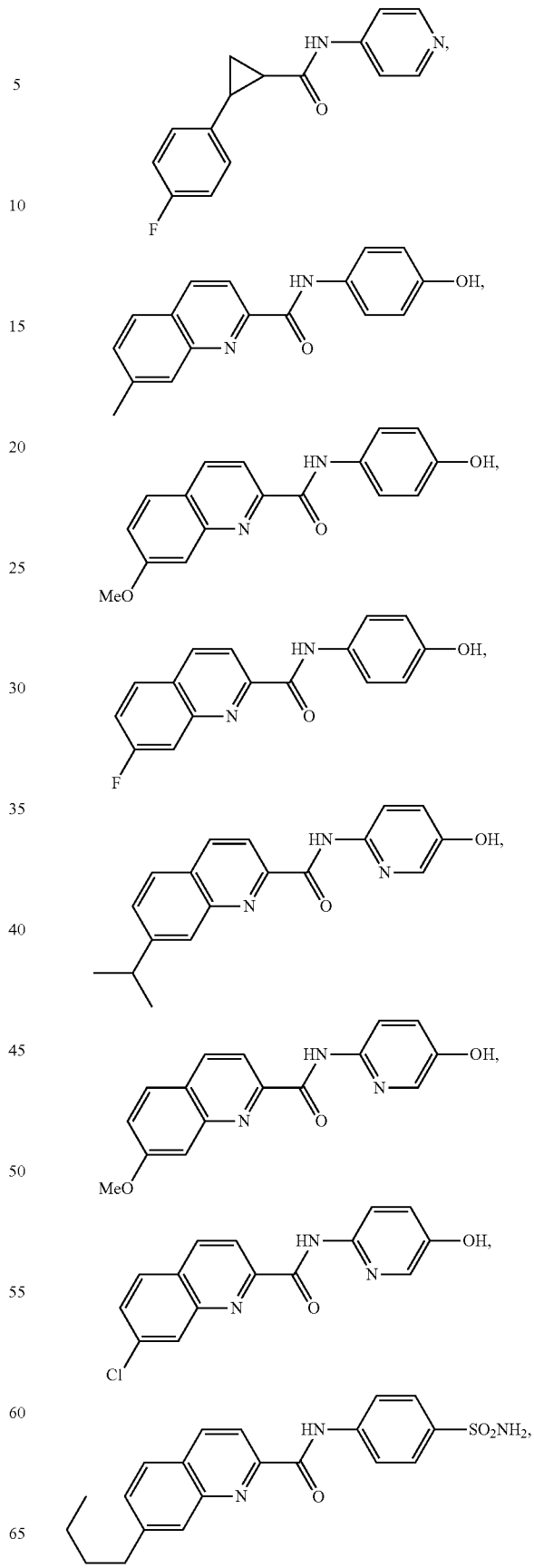

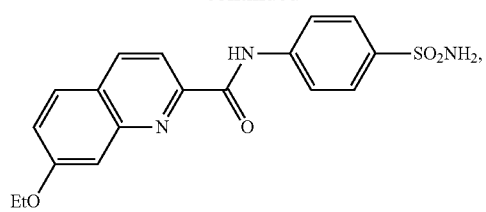
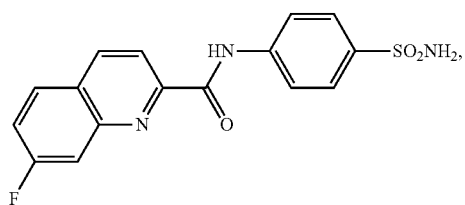
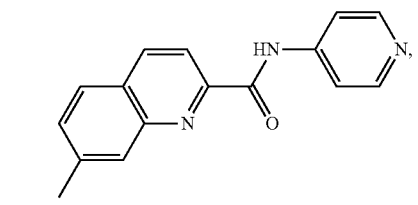
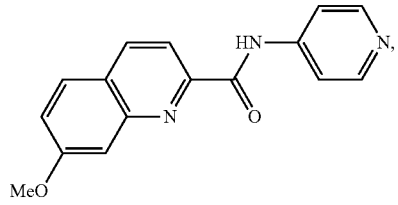
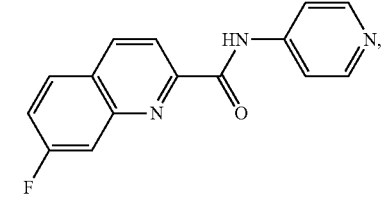
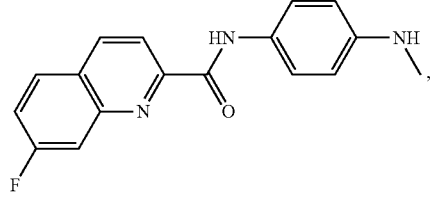
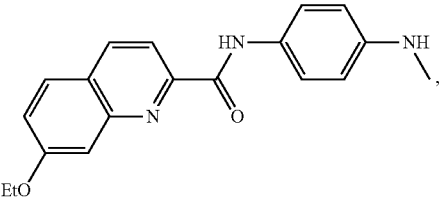
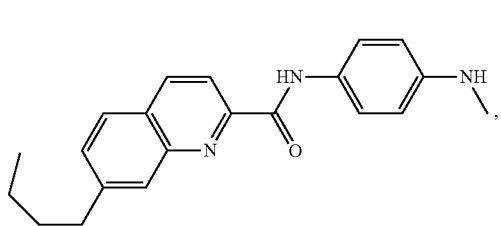
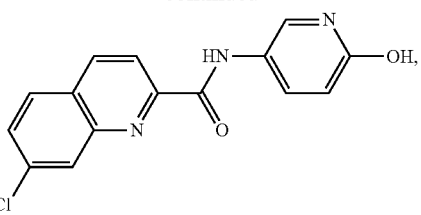
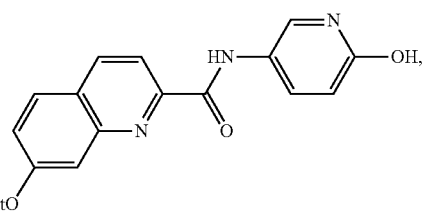
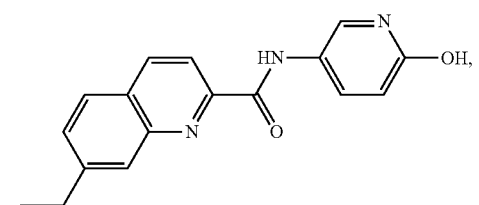
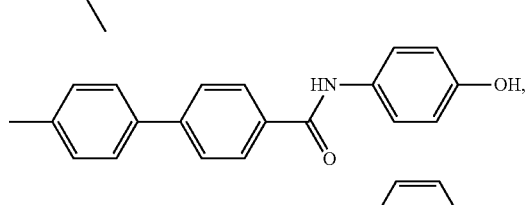
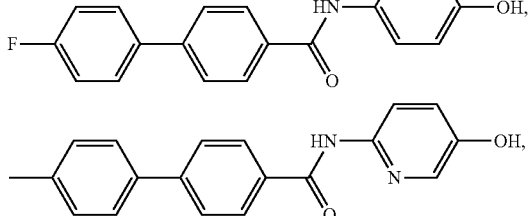
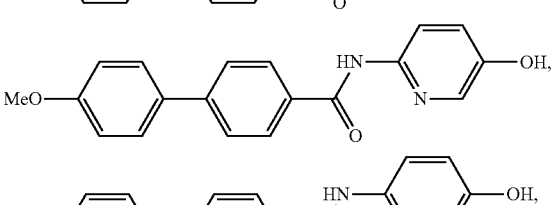
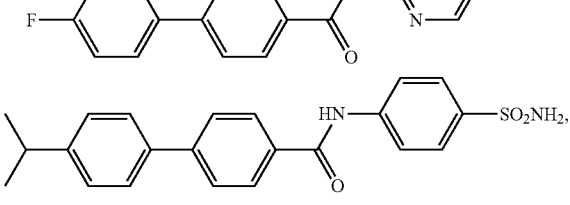
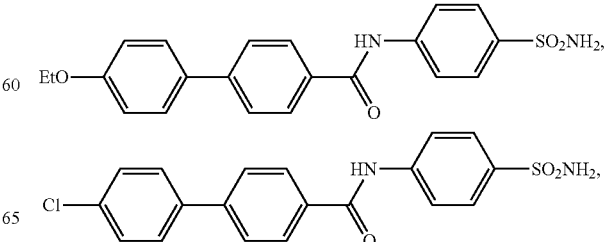

-continued

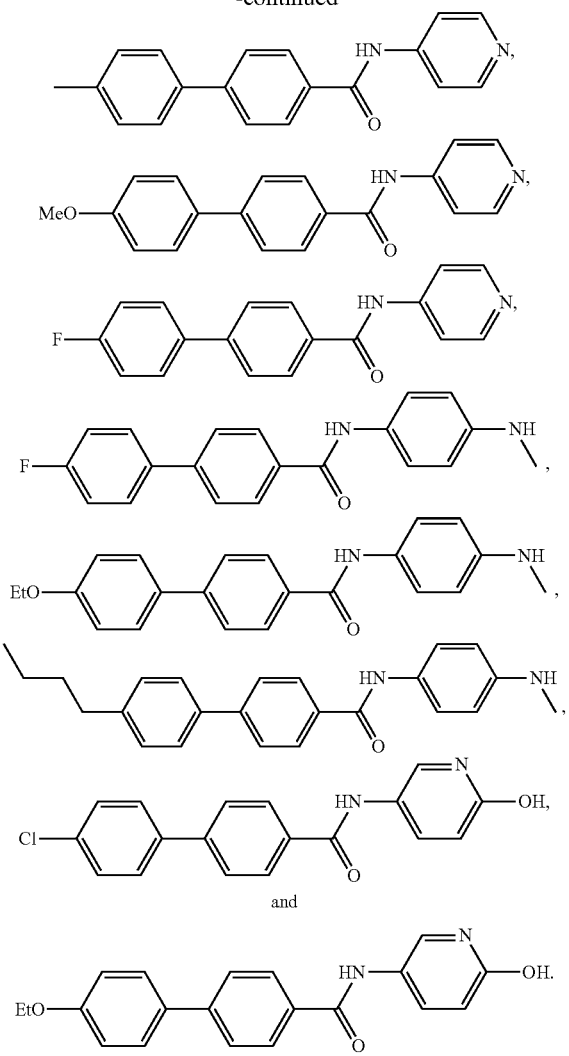

Biological Activity Assays

Des1 Activity Assays

The following are examples of in vitro cellular assays that may be used to evaluate the potential inhibitory activity of compounds disclosed herein against Des1 as well as disease-specific physiological consequences of Des1 inhibition. Jurkat T Cell Measurement of Conversion of Dihydroceramide to Ceramide Jurkat clone E6-1 cells were grown and then seeded at $10^6$ cells/mL in a 96-well plate (400 μL in each well. The cells were administered 100 μL of cell culture media containing 50-μM NBD-C6-dihydroceramide (Des1 substrate), affording a final concentration of substrate of 10 μM. The cells were incubated with substrate at 4° C. for 30 minutes. Following the incubation at 4° C., the cell suspension was centrifuged at 1200 rpm for 3 minutes, and the cell pellet is resuspended in 400 μL of fresh media containing various concentrations of either fenretinide (known Des1 inhibitor control compound) or test article. The final concentrations of control compound and test compounds were tested in a range from 0-10 μM. The cells and compounds were incubated at 37° C. for 3 hours. Following the 3-hour incubation, the plate was centrifuged at 2500 g for 3 minutes at 4° C., followed by collection and transfer of 200 μL of the supernatant to a new 96-well plate with 300 μL of methanol an containing appropriate internal standards for liquid chromatography/tandem mass spectroscopy (LC/MS/MS) analysis (internal standard: 500 nM labetalol and 100 nM alprazolam). The samples were vortexed for 2 minutes followed by centrifugation at 3,220 g for 20 minutes. Following centrifugation, 200 μL of the supernatant was transferred to a new 96-well plate for LC-MS/MS analysis to determine the amount of NBD-C6-ceramide (Des1 product) produced. The assay was typically performed in duplicate. A reduction of at least 30% compared to vehicle control (0 μM test article) is indicative of an active compound, and a reduction of 75% compared to vehicle control is preferred. By way of example, fenretinide exhibits a half-maximal inhibitory concentration (IC50) of 100-250 nM, and a number of the compounds described herein exhibit $IC_{50}$ values <50 nM.

TABLE 2

Biological activity

| Ex. | Des1 % Inhib (10 μM) | Des1 $IC_{50}$, μM | Des1 % Inhib (1 μM) | Des1 % Inhib (0.5 μM) |
|---|---|---|---|---|
| 1 | N.D. | N.D. | N.D. | N.D. |
| 2 | 78 | 0.84 | N.D. | N.D. |
| 3 | 49 | 4.46 | N.D. | N.D. |
| 4 | 85 | 0.44 | N.D. | N.D. |
| 5 | 88 | 0.05 | N.D. | N.D. |
| 6 | 76 | 0.59 | N.D. | N.D. |
| 7 | N.D. | 0.18 | 79.80 | N.D. |
| 8 | N.D. | 0.06 | 85.90 | N.D. |
| 9 | N.D. | 0.010, 0.026 | 93.30 | N.D. |
| 10 | N.D. | 0.23 | 67.20 | N.D. |
| 11 | 20 | >10 | N.D. | N.D. |
| 12 | N.D. | N.D. | N.D. | N.D. |
| 13 | 38 | 8.2 | N.D. | N.D. |
| 14 | 14.8 | >10 | N.D. | N.D. |
| 15 | 87 | 0.09 | N.D. | N.D. |
| 16 | 54 | N.D. | N.D. | N.D. |
| 18 | N.D. | 4.5 | N.D. | N.D. |
| 19 | N.D. | N.D. | 31 | N.D. |
| 20 | N.D. | 0.004 | 95.9 | N.D. |
| 21 | N.D. | N.D. | N.D. | 62.76 |
| 22 | N.D. | 0.014 | 95.4 | N.D. |
| 23 | N.D. | 0.005 | 96.3 | N.D. |
| 24 | N.D. | 0.003 | 96.09 | N.D. |
| 25 | N.D. | N.D. | 4.44 | N.D. |
| 26 | N.D. | 0.240 | 74.5 | N.D. |
| 27 | N.D. | 0.016 | N.D. | N.D. |
| 28 | N.D. | 0.005 | 96.19 | N.D. |
| 29 | N.D. | 0.006 | 95.66 | N.D. |
| 30 | N.D. | N.D. | N.D. | 49.55 |
| 31 | N.D. | 0.001 | N.D. | 91 |
| 32 | N.D. | 0.001 | N.D. | 96.75 |
| 33 | N.D. | N.D. | N.D. | 71.06 |
| 34 | N.D. | 0.130 | N.D. | 85.57 |
| 35 | N.D. | 0.004 | 95.71 | 90.04 |
| 36 | N.D. | N.D. | N.D. | 44.8 |
| 37 | N.D. | 0.021 | N.D. | 93.74 |
| 38 | N.D. | 0.019 | N.D. | 95.37 |
| 39 | N.D. | N.D. | N.D. | 65.92 |
| 40 | N.D. | 0.021 | N.D. | 92.62 |
| 41 | N.D. | 0.088 | N.D. | 81.32 |
| 42 | N.D. | 0.130 | N.D. | 85.5 |
| 43 | N.D. | N.D. | N.D. | 59.32 |
| 44 | N.D. | 0.063 | N.D. | 87.99 |
| 45 | N.D. | 0.023 | N.D. | 94.05 |
| 46 | N.D. | N.D. | N.D. | 96.17 |
| 47 | N.D. | 0.050 | N.D. | N.D. |
| 48 | N.D. | 0.25 | N.D. | 91.32 |
| 49 | N.D. | 0.013 | N.D. | 96.8 |
| 50 | N.D. | 0.14 | N.D. | 92.28 |
| 51 | N.D. | 0.005 | N.D. | 97.27 |
| 52 | N.D. | 0.066 | N.D. | 94.13 |

TABLE 2-continued

Biological activity

| Ex. | Des1 % Inhib (10 µM) | Des1 IC$_{50}$, µM | Des1 % Inhib (1 µM) | Des1 % Inhib (0.5 µM) |
|---|---|---|---|---|
| 53 | N.D. | 0.002 | N.D. | N.D. |
| 54 | N.D. | 0.011 | N.D. | 96.62 |
| 55 | N.D. | N.D. | N.D. | N.D. |
| 56 | N.D. | N.D. | N.D. | N.D. |
| 57 | N.D. | 0.0039 | N.D. | N.D. |
| 58 | N.D. | N.D. | N.D. | N.D. |
| 59 | N.D. | N.D. | N.D. | N.D. |

N.D. = not determined.

C2C12 Myolube Assay of Insulin-Stimulated Phosphorylation of Akt:

C2C12 myotubes are treated with 0.75 mM BSA-conjugated palmitate for 16 hours in the presence or absence of 7 non-zero concentrations of fenretinide (Des1 inhibitor control compound) or various test articles, followed by a 10-minute stimulation with insulin (100 nM). Cells are subsequently harvested and boiled in reducing SDS sample buffer and subjected to SDS-PAGE followed by detection of phosphorylated Akt, total Akt, and a suitable loading control (e.g. actin or GAPDH) by western blot using fluorescently-conjugated secondary antibodies. Band intensities are quantitated by an Odyssey imaging system (Li-COR), but could also be performed using HRP-conjugated secondary antibodies/enhanced chemiluminescence or by colorimetric readout.

Moreover, while currently contemplated for SDS-PAGE/immunoblot format, this assay could be adapted to ELISA or in-cell western (immunocytochemistry) formats for higher throughput testing of compounds. An increase of 30% compared to vehicle control (0 µM test article) is indicative of an active compound, and an increase of 50% compared to control is preferred. By way of example, fenretinide exhibits a half-maximal effective concentration (EC50) for increasing insulin-stimulated Akt phosphorylation in the presence of palmitate of 600 nM. Des1 inhibitors disclosed herein are expected to be effective in this assay.

Rodent High Fat Dietary Model of Insulin Resistance, Dyslipidemia, and NAFLD/NASH:

A standard model of human hyperlipidemia and insulin resistance is the mouse fed a high fat diet for several weeks. Test compounds are evaluated in this model as agents to restore insulin sensitivity and lower blood lipids. The chronic high fat diet is fed to mice to simulate a standard Western diet which is elevated in calories from high fat and carbohydrate intake. This and similar models of dietary induced obesity, insulin insensitivity and elevated serum lipids and cholesterol are used as mouse and rat models of human pathology including hyperlipidemia, type II diabetes, atherosclerosis, obesity, cardiovascular and liver disease. These models have been used as excellent predictors of efficacy in human clinical trials (PPAR and FXR agonists). Key endpoints used to assess therapeutic activity of candidate Des1 inhibitors including fasting blood glucose, insulin, triglycerides, cholesterol, and hepatosteatosis. Glucose and insulin tolerance studies can also be performed. Glycosylated hemoglobin can also be measured as a more chronic marker of hyperglycemia. Hepatosteatosis (fatty liver) can be assessed by Oil Red O staining of liver sections as well as by quantitative determination of liver triglycerides. Des1 inhibitors are expected to demonstrate efficacy in this assay, improving insulin sensitivity, lowering blood lipids, reducing or preventing the development of hepatosteatosis, and/or generally demonstrating efficacy in measures of pathology relevant to dyslipidemia, type II diabetes, atherosclerosis, obesity, cardiovascular diseases, and/or liver diseases such as NASH or NAFLD.

Measurement of In Vivo Activity in a Models of Atherosclerosis:

A key workhorse rodent model of atherosclerosis is the high fat diet-fed ApoE−/− (ApoE knockout) mouse, which develops atherosclerotic lesions which can be measured in various aspects of the aorta. By way of example, male ApoE−/− mice of 8 weeks of age are fed a high fat diet for 30 days to establish atherosclerotic lesions. A control group of animals are terminated to assess aortic lesion status following the 30 days of high fat dieting. Subsequently, two groups of mice are switched to a standard chow diet for another 60 days, during which the animals are dosed with either vehicle, a candidates Des1 inhibitor, or a reference control compound (e.g. myriocin). Following the 60 days of dosing, mice are fasted overnight, and perfusion-fixed aortas are dissected to enable lesion analysis of the aortic sinus, aortic arch, and celiac branchpoint of the abdominal aorta. Morphometric analysis of these three aortic sites is conducted after the tissues are subjected to Verhoeff staining (Glaros et al. (2008) Myriocin slows the progression of established atherosclerotic lesions in apolipoprotein E gene knockout mice. J. Lipid Res. 49, 324-331).

Des1 inhibitors disclosed herein would be anticipated to prevent the development of or effect the regression of established atherosclerotic lesions.

Measurement of In Vitro Cellular Anti-Cancer Activity:

PC3 prostate cancer, MCF7 ER+ breast cancer cells, or various other cancer cell lines are cultured in DMEM (containing 10% fetal calf serum and penicillin-streptomycin). A frozen aliquot of cells is resuspended in 5 mL of warm media and centrifuged for 5 mins at 200 g. The supernatant is aspirated and the cell pellet resuspended in 5 mL media. Cells are then grown in tissue culture flasks at 37° C. with 5% $CO_2$ and passaged when 80-90% confluent 4 times before use. Cells are then incubated for 5 mins with Trypsin to separate from cell culture flanks. Before treatment with drug compounds, cells are plated at 2,500 cells/well in 96-well plates and incubated at 37° C. with 5% $CO_2$ in a humidified incubator for 24 hours prior. Fenretinide (Des1 control inhibitor) or various test articles are diluted in media to final concentrations ranging from 10 µM down to 0 µM, with DMSO as a vehicle control (final DMSO concentration of 0.1%). Cell culture supernatants are aspirated and replaced with media containing either fenretinide or various test articles. Drug treatments are performed in duplicate wells. Cells are incubated with drug compounds at 37° C. with 5% $CO_2$ in a humidified incubator for 72 hours prior to determination of cell viability. Following the 72-hour incubation with compounds, cell culture supernatants are then aspirated from wells and replaced with 100 µL of CellTiter Glo solution. Triplicate cell-free control wells containing only CellTiter solution are also included in each assay. Cells are then incubated at 37° C. with 5% $CO_2$ in a humidified incubator for 1 hour at which time absorbance is read at 490 nm by microplate reader instrument. Background absorbance (taken from cell-free control wells) is subtracted from each reading. To determine percentage inhibition of cell viability, absorbance readings for each drug treatment are expressed as a fraction of the vehicle control (0.1% DMSO) readings. For each drug concentration the mean (+/−SEM) is calculated and graphed using GraphPad Prism or other suitable scientific graphing package. A sigmoidal curved is fitted to the data and used to calculate the IC50 of each compound. A reduction of cancer cell viability by at least 30% compared to vehicle control (0 µM test article) is indicative of an active compound, and a reduction of 50% compared to control is preferred. Des1 inhibitors disclosed herein are expected to be effective in reducing cancer cell viability and thus to be effective in the treatment of cancer.

Measurement of In Vivo Anti-Cancer Activity:

Human tumor xenografts in immunocompromised mice (e.g. athymic nude mice), implanted either orthotopically or ectopically, represent the workhorse models for predicting the clinical efficacy of candidate anti-cancer agents. By way of example, in the case of ER+ breast cancer, ovariectomized estrogenized (0.72 mg/60 days 170-estradiol (E2) time-released sc pellet) NU/NU mice (~6 weeks of age) are injected with $5 \times 10^6$ MCF7 cells (a human cell line derived from an ER+ breast cancer) into the axial mammary fat pad. Tumors are measured by caliper three times per week until tumor volume (($L^2 \cdot W$)/2) reaches 0.2 cm$^3$, followed by randomization of mice into treatment groups with test compounds in the presence or absence of standard-of-care agents (e.g. tamoxifen). Active Des1 inhibitors would be anticipated to show tumor growth inhibition or regression over a 28-day treatment period, indicative of potential anti-cancer activity of test compounds.

In addition, test compounds can also be assessed for potential anti-cancer activity in syngeneic and/or genetically-engineered mouse models of various tumors in order to have the benefit of having a fully intact immune system (e.g. MC38 model of colorectal cancer or KPC model of pancreatic ductal adenocarcinoma). Candidate Des1 inhibitors may inhibit the activity and/or recruitment of various cell types (e.g. myeloid-derived suppressor cells, regulatory T cells) which lead to immunosuppression in the tumor microenvironment, and thus have synergistic activity with various immune check-point inhibitors, including monoclonal antibody therapeutics targeting PD1, PD-L1, CTLA-4, CD47, and OX40, as well as small molecules targeting indoleamine-2,3-dioxygenase 1 or arginase-1, which are used to reawaken the immune system to enable immunological attack of the tumor. Such therapy would be anticipated to generate anti-tumor immunity and potentially a durable anti-tumor memory response.

Des1 inhibitors disclosed herein are expected to be effective as single agents as well as in combination with standard-of-care therapy in the treatment of cancer.

Measurement of Activity in In Vivo Model of Cystic Fibrosis:

Genetic ablation of the cystic fibrosis transmembrane conductance regulator (CFTR) in mice recapitulates a number of the clinical manifestations of cystic fibrosis observed in patients, and has become a workhorse pharmacology model of this disease. As ceramide has been demonstrated to accumulate in the lungs of mouse knockouts of CFTR (CFTR-KO) and to create a pro-inflammatory environment, measuring the ratio of lung arachidonic acid (AA—a lipid precursor to pro-inflammatory mediators) to docosahexaenoic acid (DHA). A high AA/DHA ratio is indicative a pro-inflammatory environment. Fenretinide, a known Des1 inhibitor, has previously been demonstrated to normalize this ratio (and hence reduce inflammation) in the lungs of CFTR-KO mice, as well as reduce susceptibility to infection with *Pseudomonas aeruginosa* (Guilbault et al. 2009 Cystic fibrosis fatty acid imbalance is linked to ceramide deficiency and corrected by fenretinide. Am. J. Respir. Cell Mol. Biol. 41, 100-106; Guilbault et al. 2008 Fenretinide corrects newly found ceramide deficiency in cystic fibrosis. Am. J. Respir. Cell Mol. Biol. 38, 47-56). Consequently, candidate Des1 inhibitors could be tested in this CFTR-KO mouse model of cystic fibrosis with key endpoints being the AA/DHA ratio as well as the inflammatory response to, and ability to clear, *Pseudomonas aeruginosa* challenge. Longer term, mice lacking CFTR develop substantial pulmonary fibrosis which can be assessed histologically (e.g. Sirius Red or trichrome staining of lung tissue) of by quantitative assessment of hydroxyproline in lung tissue. Des1 inhibitors disclosed herein would be anticipated to normalize the ratio of lung AA to DHA, normalize the ratio of circulating AA to DHA, reduce lung inflammation, and reduce lung fibrosis.

Measurement of In Vitro Cellular Anti-Fibrotic Activity:

Normal and SSc (diffuse systemic sclerosis) skin fibroblasts are cultured in DMEM supplemented with 10% FBS and 1% antibiotic antimycotic solution. Cells are incubated with serum-free media for 24 hours before specific treatments, including fenretinide (Des1 inhibitor control compound) and various test articles at concentrations ranging from 10 µM down to 0 µM (DMSO vehicle control, 0.1%) for 12-24 hours at 37° C. Smad3 (a downstream signaling intermediate of the TGFβ pathway) as well as collagen (COL1A1) are measured as in vitro surrogates of a pro-fibrotic state. A reduction of at least 30% compared to vehicle control (0 µM test article) is indicative of an active compound, and a reduction of 50% compared to control is preferred. Des1 inhibitors disclosed herein are expected to be effective in reducing measures and markers of fibrosis.

Measurement of In Vivo Anti-Fibrotic Activity:

Various rodent models exist for assessing potential in vivo anti-fibrotic activity of test compounds, including those representing fibrosis of the lungs, kidney, liver, and skin/connective tissues. By way of example, and in the case of liver fibrosis, rodents (mice or rats) are injected with a $CCl_4$, a hepatotoxin, followed by randomization of animals into treatment groups (using pirfenidone as a reference control compound) and assessment at 6-8 weeks post-$CCl_4$ injection. Key measures of liver fibrosis to assess potential therapeutic efficacy of test compounds include liver function tests (e.g. AST, ALT, bilirubin), hydroxyproline content in the liver, and Sirius Red staining of liver histological sections. An active Des1 inhibitor would be anticipated to substantially reduce the level of Sirius Red staining in the liver, as well as hydroxyproline level. Des1 inhibitors disclosed herein would be expected to reduce fibrosis of various organs, including liver, lung, kidney, heart, and skin.

Measurement of Disease-Modifying Activity in Multiple Sclerosis:

There are numerous mouse models of multiple sclerosis (MS), including those in which animals are immunized with myelin oligodendrocyte glycoprotein (MOG) (chronic progressive model) and proteolipoprotein (PLP (relapsing/remitting model), as well as others which rely on adoptive cellular transfer technologies. By way of example, and in the case of the MOG chronic progressive model, chronic progressive EAE develops in C57BL/6 mice after immunization with an emulsion of $MOG_{35-55}$/CFA or $MOG_{1-125}$/CFA followed by injection of pertussis toxin. This model is used to test the potential of compounds to prevent or mitigate EAE disease. It can be run with the compound dosed from the time of immunization (prophylactic treatment), or with the aim of reversing the course of disease and facilitating recovery by dosing the compound from the time of EAE onset (therapeutic treatment). The model uses female C57BL/6 mice of age 10 to 14 weeks at the start of the study. Typically, EAE develops 8-18 days after immunization.

EAE development is usually followed for 4 weeks (28 days) after immunization. Compounds can be assessed for their ability to reduce the severity or incidence of disease (both by scoring of limb weakness/paralysis and behavior, as well as by histopathology of the spinal card including extent of demyelination) in comparison to reference control compounds (e.g. fingolimod). An active Des1 inhibitor would be anticipated to reduce the severity of disease (clinical score), the extent of spinal cord demyelination, inflammatory cell infiltrates into the spinal cord, and number of apoptotic cells in the spinal cord. Active Des1 inhibitors could be combined with other therapeutics for multiple sclerosis, including fingolimod (and other sphingosine-1-phosphate receptor modulators), teriflunomide, dimethyl fumarate, PAD4 inhibitors, anti-CD20 and anti-CD52 mAbs, natalizumab, glatiramer acetate, and interferon-β. Des1 inhibitors disclosed herein would be expected to have disease-modifying activity or provide symptomatic relief in multiple sclerosis.

Measurement of Disease Modifying Anti-Rheumatic Drug (DMARD) Activity:

The collagen-induced arthritis (CIA) model is considered a suitable model for studying potential drugs active in human rheumatoid arthritis because of the many immunological and pathological similarities to human rheumatoid arthritis (RA), the involvement of localized major histocompatibility, complete class-II-restricted T helper lymphocyte activation, and the similarity of histological lesions. Features of this CIA model that are similar to that found in RA patients include: erosion of cartilage and bone at joint margins (as can be seen in radiographs), proliferative synovitis, symmetrical involvement of small and medium-sized peripheral joints in the appendicular, but not the axial, skeleton. The compounds disclosed herein can be tested for activity against autoimmune arthritis (e.g. reduction in severity or incidence of disease) using the protocols described in Rosloniec E F et al., "Collagen☐Induced Arthritis," *Current Protocols in Immunology*, Unit 15.5 (1993). Compounds can be assessed for their ability to reduce the severity or incidence of disease (both by examination of the external appearance of the joints as well as their architecture by histopathology) in comparison to reference control compounds (e.g. dexamethasone). An active Des1 inhibitor would be anticipated to reduce severity and or incidence of disease in collagen-induced arthritis models. Active Des1 inhibitors could be administered in combination with various analgesics (including traditional NSAIDs and COX2-selective inhibitors), steroids, methotrexate, gold salts, hydroxychloroquine, PAD4 inhibitors, sulfasalazine, leflunomide, anti-TNFα, inhibitors of janus kinases, abatacept, rituximab, and anakinra. Des1 inhibitors disclosed herein would be expected to have disease-modifying activity or provide symptomatic relief in rheumatoid arthritis.

Measurement of Activity in Alzheimer's Disease

There are various animal models of neurodegenerative diseases, including Alzheimer's disease, Parkinson's disease, Huntington's disease, and amyotrophic lateral sclerosis. A standard mouse model known in the art is TgCRND8, an early-onset disease model that is transgenic for encoding the double mutant form of the amyloid precursor protein 695 (KM670/671NL1V717F) under the control of the PrP gene promoter. These mice develop the cortical $A\beta_{42}$ and hyperphosphorylated Tau protein which resemble some of the clinical features of Alzheimer's disease. Animals are dosed with Des1 inhibitors at 4 weeks of age for 4 months, followed by post-mortem assessment of brain ceramides, $A\beta_{42}$ and hyperphosphorylated Tau protein. An active Des1 inhibitor would be anticipated to lower brain ceramides, as well as the levels of the potentially disease-causing $A\beta_{42}$ and hyperphosphorylated Tau proteins. Des1 inhibitors could potentially be administered in combination with other therapeutics for Alzheimer's disease, including cholinesterase inhibitors and memantine. Des1 inhibitors disclosed herein would be expected to have disease-modifying activity or provide symptomatic relief in Alzheimer's disease.

Measurement of Activity in Amyotrophic Lateral Sclerosis:

The most commonly-used animal model of amyotrophic lateral sclerosis (ALS) is the SOD1-G93A transgenic mouse, with a phenotype which partially recapitulates what is observed clinically in patients. Mice develop paralysis in one or more limbs within a few months (accompanied by decreased longitudinal grip strength), and key disease endpoints include grip strength, as well as assay of lipid peroxidase activity (MDA) in spinal cord, and astrocytosis (GFAP) in ventral thalamus. Animals are dosed with Des1 inhibitors either early in disease (~12 weeks of age) or late in disease (18-20 weeks of age), followed by in-life assessments (grip strength) and post-mortem measurements (lipid peroxidase and astrocytosis). Active compounds would be anticipated to increase grip strength, decrease lipid peroxidase activity in the spinal cord, and decrease astrocytosis in the brain. Des1 inhibitors could also be dosed in combination with other therapeutics for ALS, including riluzole and/or edavarone. Des1 inhibitors disclosed herein would be expected to have disease-modifying activity or provide symptomatic relief in ALS.

Measurement of Activity in Models of Lipid Storage Disorders:

A representative lipid storage disorder in which a Des1 inhibitor would be anticipated to be efficacious is Farber disease, caused by the lack of activity of the lysosomal ceramide-degrading enzyme known as acid ceramidase (ASAH1). Mouse models in which ASAHI mutated (e.g. P362R is an inactivating point mutation in the ASAHI gene) recapitulate a number of key features of Farber disease, and serve as a readily-available system for assessing potential efficacy of drug candidates. There is a characteristic massive accumulation of ceramide into tissues, with corresponding infiltration of macrophages and elevated levels of various cytokines (e.g. MCP1) detectable in the circulation. Key assessments of potential Des1 inhibitor activity in this model include: levels of ceramide in liver, spleen, kidney, and heart; mass of spleen; plasma MCP1 level; and histopathology of liver and spleen to assess macrophage infiltration. Des1 inhibitors could also be dosed in combination with enzyme replacement therapy (e.g. recombinant human acid ceramidase).

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A method of inhibiting dihydroceramide desaturase (Des) activity in a biological sample comprising contacting the biological sample with a compound of Formula I:

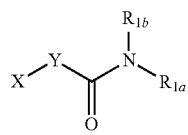

(I)

or a salt thereof, wherein:

R$_{1a}$ and R$_{1b}$ are independently selected from hydrogen, cycloalkylalkyl, aryl, and heteroaryl, and is optionally substituted with 1, 2, or 3 R$_2$ groups, or R$_{1a}$ and R$_{1b}$ together with the intervening atoms, form a 5-7 membered heterocyclic ring, and is optionally substituted with 1, 2, or 3 R$_2$ groups;

at least one of R$_{1a}$ and R$_{1b}$ is not hydrogen;

X is selected from ethenyl, alkyl, aryl, biaryl, (aryl)cycloalkyl, (aryl)heterocycloalkyl, (aryl)heteroaryl, cycloalkyl, (cycloalkyl)aryl, (cycloalkyl)cycloalkyl, (cycloalkyl)heterocycloalkyl, (cycloalkyl)heteroaryl, heterocycloalkyl, (hetercycloalkyl)aryl, (heterocycloalkyl)cycloalkyl, (heterocycloalkyl)heteroaryl, (heterocycloalkyl)heterocycloalkyl, heteroaryl, (heteroaryl)aryl, (heteroaryl)cycloalkyl, (heteroaryl)heterocycloalkyl, and (heteroaryl)heteroaryl, any of which is optionally substituted with 1, 2, 3, or 4 R$_3$ groups;

Y is selected from —CHR$_4$—, —CHR$_4$CHR$_4$—, and —CR$_4$=CR$_4$;

each R$_2$ is independently selected from alkyl, alkoxy, amino, cycloalkyl, heterocycloalkyl, (heterocycloalkyl)alkyl, halogen, hydroxy, S-sulfonamido, and oxo, and is optionally substituted with 1, 2, or 3 R$_5$ n is selected from 1, 2, 3, 4, and 5;

each R$_3$ is independently selected from alkyl, alkoxy, cyano, haloalkyl, hydroxy, halogen, and oxo; and each R$_4$ is independently selected from hydrogen, alkyl, alkylamino, halo, and hydroxyl; and each R$_5$ is independently selected from hydroxy and alkoxy.

2. The method as recited in claim 1, wherein exactly one of R$_{1a}$ and R$_{1b}$ is hydrogen; and exactly one of R$_{1a}$ and R$_{1b}$ is selected from phenyl, pyridinyl, pyridazinyl, pyrimidinyl, pyrazinyl, imidazolyl, quinolinyl, isoquinolinyl, and diazanaphthalenyl, and is optionally substituted with 1 or 2 R$_2$ groups.

3. The method as recited in claim 2, wherein at least one R$_2$ is hydroxyl.

4. The method as recited in claim 3, wherein exactly one of R$_{1a}$ and R$_{1b}$ is selected from

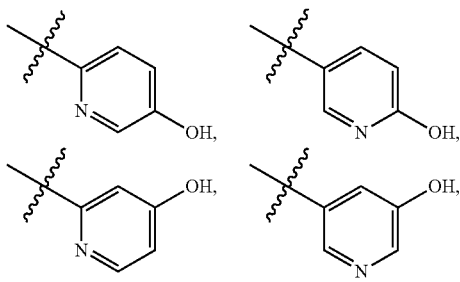

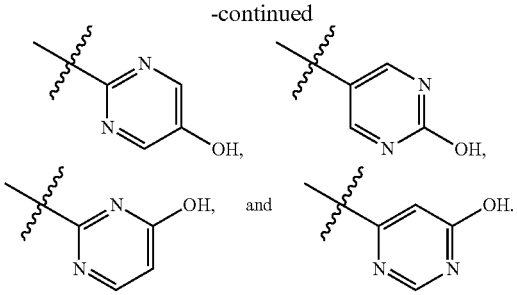

5. The method as recited in claim 4, wherein exactly one of R$_{1a}$ and R$_{1b}$ is 5-hydroxypyridin-2-yl.

6. The method as recited in claim 5, wherein X is selected from cycloalkyl, (cycloalkyl)phenyl, phenyl, (phenyl)cycloalkyl, (phenyl)piperidinyl, (phenyl)piperazinyl, pyridinyl, (pyridinyl)cycloalkyl, (pyridinyl)phenyl, (pyridinyl)piperidinyl, (pyridinyl)piperazinyl, biphenyl, naphthyl, quinolinyl, isoquinolinyl, benzofuranyl, indolyl, indazolyl, and benzotriazolyl, any of which is optionally substituted with 1, 2, or 3 R$_3$ groups.

7. The method as recited in claim 1, wherein exactly one of R$_{1a}$ and R$_{1b}$ is selected from phenyl and 5-hydroxypyridin-2-yl.

8. The method as recited in claim 7, wherein X is selected from aryl, biaryl, cycloalkyl, heteroaryl, and heterocycloalkyl, any of which is optionally substituted with 1, 2, or 3 R$_3$ groups.

9. The method as recited in claim 8, wherein

X is phenyl, and is optionally substituted with 1 or 2 R$_3$ groups; and

R$_4$ is hydrogen.

10. The method as recited in claim 1, wherein

X is alkyl, and is optionally substituted with 1, 2, 3, or 4 R$_3$ groups; and each R$_3$ is independently selected from alkoxy, cyano, hydroxy, halogen, and oxo.

11. The method as recited in claim 10, wherein

X is C$_{1-8}$alkyl, and is optionally substituted with 1 or 2 R$_3$ groups; and each R$_3$ is independently selected from alkoxy, hydroxy, and halogen.

12. The method as recited in claim 11, wherein

X is C$_{1-8}$alkyl, and is optionally substituted with 1 or 2 alkoxy groups.

13. The method as recited in claim 12, wherein exactly one of R$_{1a}$ and R$_{1b}$ is H, and exactly one of R$_{1a}$ and R$_{1b}$ is selected from

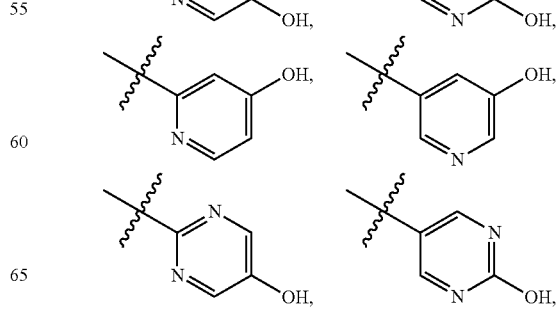

-continued

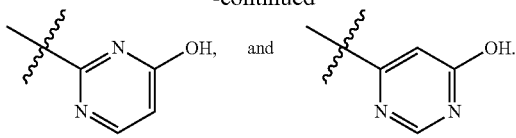

14. The method as recited in claim 13, wherein exactly one of $R_{1a}$ and $R_{1b}$ is 5-hydroxypyridin-2-yl.

15. The method as recited in claim 1, wherein
exactly one of $R_{1a}$ and $R_{1b}$ is hydrogen; and
exactly one of $R_{1a}$ and $R_{1b}$ is selected from 4-hydroxyphenyl and 5-hydroxypyridin-2-yl.

16. The method as recited in claim 15, wherein X is selected from aryl, biaryl, heteroaryl, and cycloalkyl, any of which is optionally substituted with 1, 2, 3, or 4 $R_3$ groups.

17. The method as recited in claim 16, wherein X is selected from phenyl, biphenyl, naphthyl, and cyclohexyl, any of which is optionally substituted with 1 or 2 $R_3$ groups.

18. The method as recited in claim 1, wherein the compound has the structure of Formula IV:

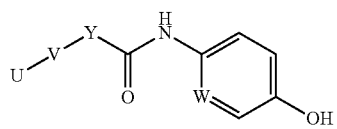

(IV)

or a salt thereof, wherein:
U is selected from aryl, cycloalkyl, heterocycloalkyl, and heteroaryl, any of which is optionally substituted with 1 or 2 $R_3$ groups;
V is selected from a bond, arylene, cycloalkylene, heterocycloalkylene, and heteroarylene, and is optionally substituted with 1 or 2 $R_3$ groups;
W is selected from CH and N;
Y is selected from —CHR$_4$—, —CHR$_4$CHR$_4$—, and —CR$_4$=CR$_4$—;
each $R_3$ is independently selected from alkyl, haloalkyl, hydroxy, alkoxy, haloalkoxy, halogen, cyano, and oxo; and
each $R_4$ is independently selected from hydrogen, alkyl, alkylamino, halo, and hydroxyl.

19. The method as recited in claim 18, wherein Y is —CH$_2$—.

20. The method as recited in claim 19, wherein
U is aryl, and is optionally substituted with 1 or 2 $R_3$ groups; and
each $R_3$ is independently selected from hydroxy, alkoxy, and halogen.

21. The method as recited in claim 20, wherein V is selected from

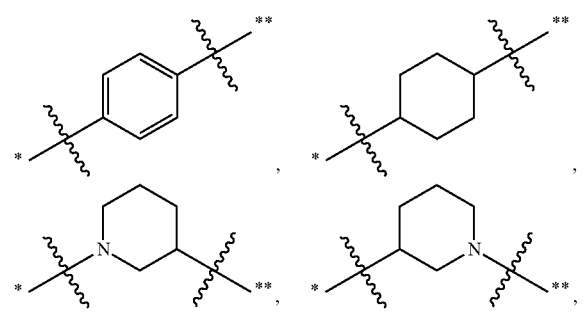

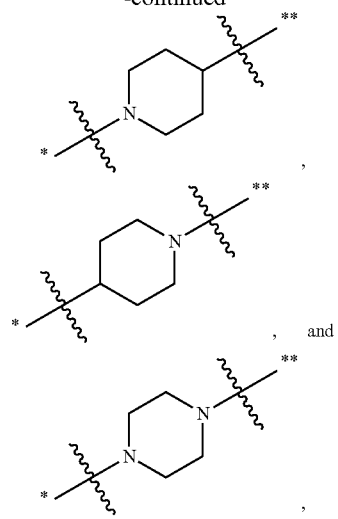

wherein:
* represents the point of attachment to Y; and
** represents the point of attachment to U.

22. The method as recited in claim 19, wherein U is selected from cycloalkyl, heterocycloalkyl, and heteroaryl, and is optionally substituted with 1 or 2 $R_3$ groups.

23. The method as recited in claim 22, wherein V is selected from

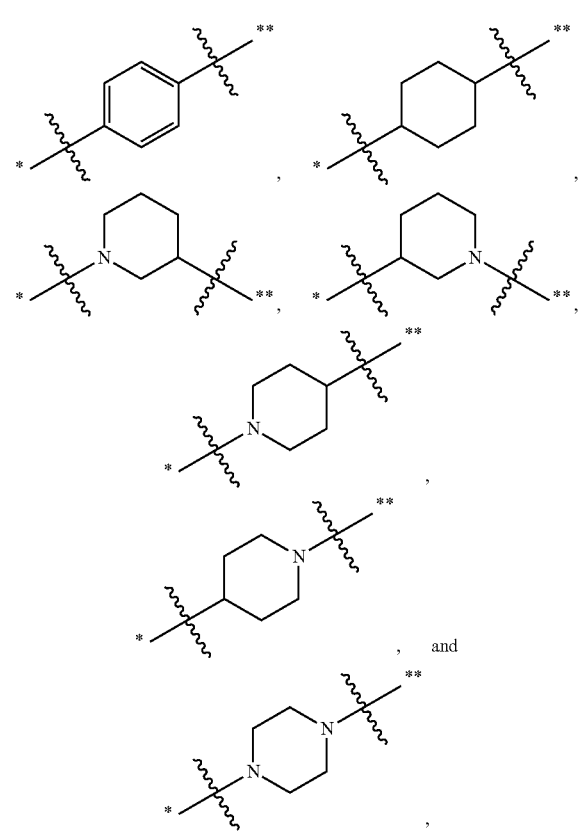

wherein:
* represents the point of attachment to Y; and
** represents the point of attachment to U.

24. The method as recited in claim 23, wherein W is N.

25. The method as recited in claim 18, wherein:
W is N;
U is selected from aryl, cycloalkyl, heterocycloalkyl, and heteroaryl, any of which is substituted with 1 or 2 $R_3$ groups;
V is bond; and each $R_3$ is independently selected from alkyl, haloalkyl, hydroxy, alkoxy, haloalkoxy, halogen, cyano, and oxo.

26. The method as recited in claim 25, wherein Y is selected from a bond and —$CH_2$—.

27. The method as recited in claim 26, wherein
U is aryl, and is optionally substituted with 1 or 2 $R_3$ groups; and
each $R_3$ is independently selected from hydroxy, alkoxy, and halogen.

28. The method as recited in claim 1, wherein the compound has the structure of Formula V:

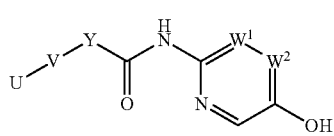

(V)

or a salt thereof, wherein:
U is selected from cycloalkyl, heterocycloalkyl, aryl, and heteroaryl, any of which is optionally substituted with 1 or 2 $R_3$ groups;
V is selected from

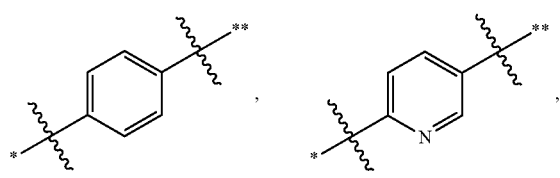
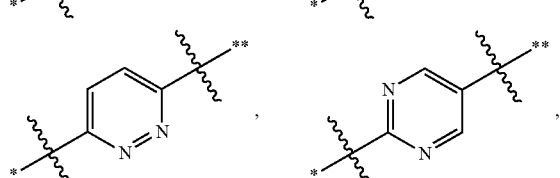
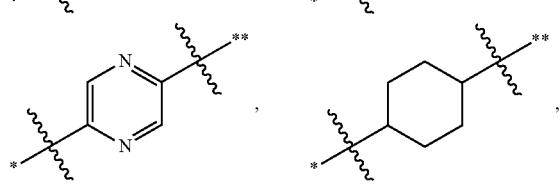
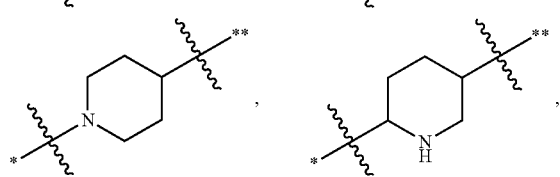
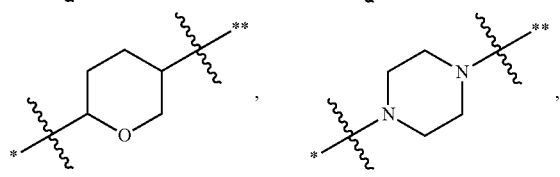
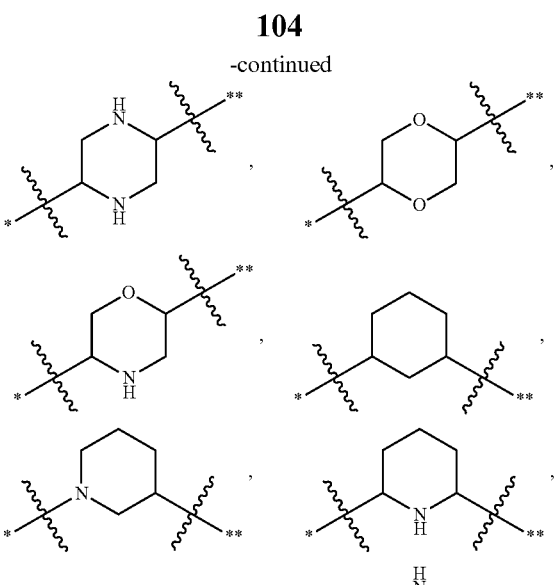

wherein either:
* represents the point of attachment to Y; and ** represents the point of attachment to U, or:
* represents the point of attachment to U; and ** represents the point of attachment to Y;
$W^1$ and $W^2$ are independently selected from CH and N;
Y is selected from —$CHR_4$—, —$CHR_4CHR_4$—, and —$CR_4=CR_4$—;
each $R_3$ is independently selected from alkyl, haloalkyl, hydroxy, alkoxy, haloalkoxy, halogen, and cyano; and
each $R_4$ is independently selected from hydrogen, alkyl, alkylamino, halo, and hydroxyl.

29. The method as recited in claim 28, wherein U is selected from monocyclic aryl, monocyclic cycloalkyl, monocyclic heterocycloalkyl, and monocyclic heteroaryl, any of which is optionally substituted with 1 or 2 $R_3$ groups.

30. The method as recited in claim 29, wherein U is selected from phenyl, pyridyl, pyrazinyl, pyrimidinyl, pyrazinyl, cyclohexyl, piperidinyl, and piperazinyl, any of which is optionally substituted with 1 or 2 $R_3$ groups.

31. The method as recited in claim 30, wherein U is selected from

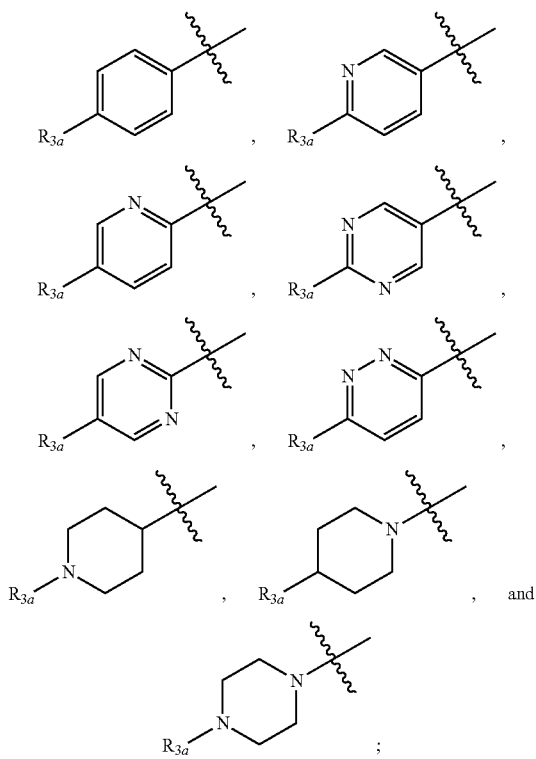

and $R_{3a}$ is selected from hydrogen, alkyl, haloalkyl, hydroxy, alkoxy, haloalkoxy, halogen, and cyano.

32. The method as recited in claim 1, wherein the compound has the structure of Formula VI:

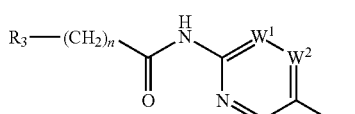

(VI)

or a salt thereof, wherein:

n is selected from 4, 5, 6, 7, 8, 9, and 10;

$W^1$ and $W^2$ are independently selected from CH and N; and $R_3$ is selected from $C_{2-10}$alkyl, haloalkyl, hydroxy, alkoxy, haloalkoxy, halogen, and cyano.

33. The method as recited in claim 32, wherein $W^1$ and $W^2$ are CH.

34. The method as recited in claim 33, wherein $R_3$ is selected from $C_{2-10}$alkyl, hydroxy, $C_{1-4}$alkoxy, and haloalkoxy.

35. The method as recited in claim 34, wherein $R_3$ is selected from $C_{2-10}$alkyl and $C_{1-4}$alkoxy.

36. The method as recited in claim 1, wherein the compound has the structure of Formula VII:

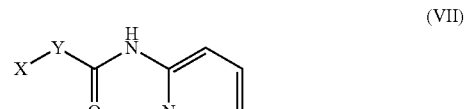

(VII)

or a salt thereof, wherein:

X is selected from

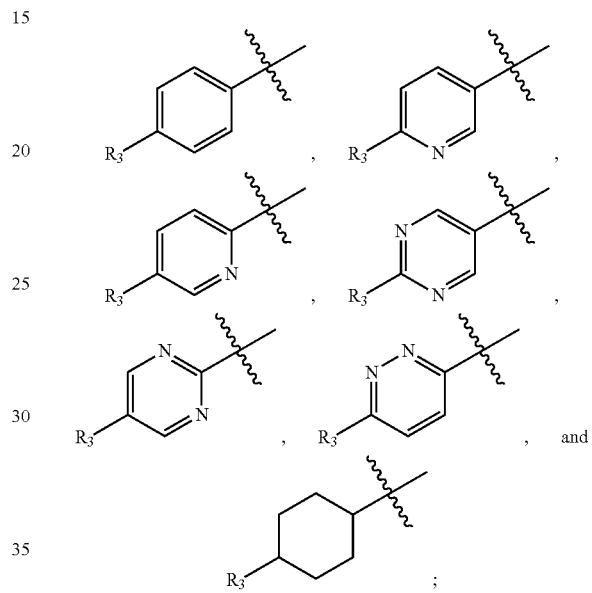

Y is selected from —CHR$_4$—, —CHR$_4$CHR$_4$—, and —CR$_4$=CR$_4$—;

$R_3$ is selected from alkyl, haloalkyl, hydroxy, alkoxy, haloalkoxy, halogen, cyano, and oxo; and each $R_4$ is independently selected from hydrogen, alkyl, alkylamino, halo, and hydroxyl.

37. The method as recited in claim 36, wherein Y is a bond.

38. The method as recited in claim 37, wherein $R_3$ is selected from alkyl, haloalkyl, hydroxy, alkoxy, and haloalkoxy.

39. The method as recited in claim 1, wherein the compound is chosen from

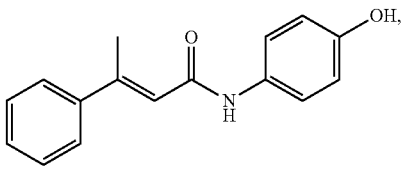

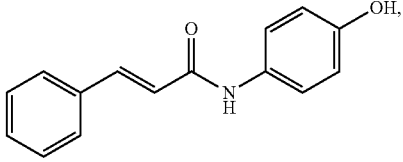

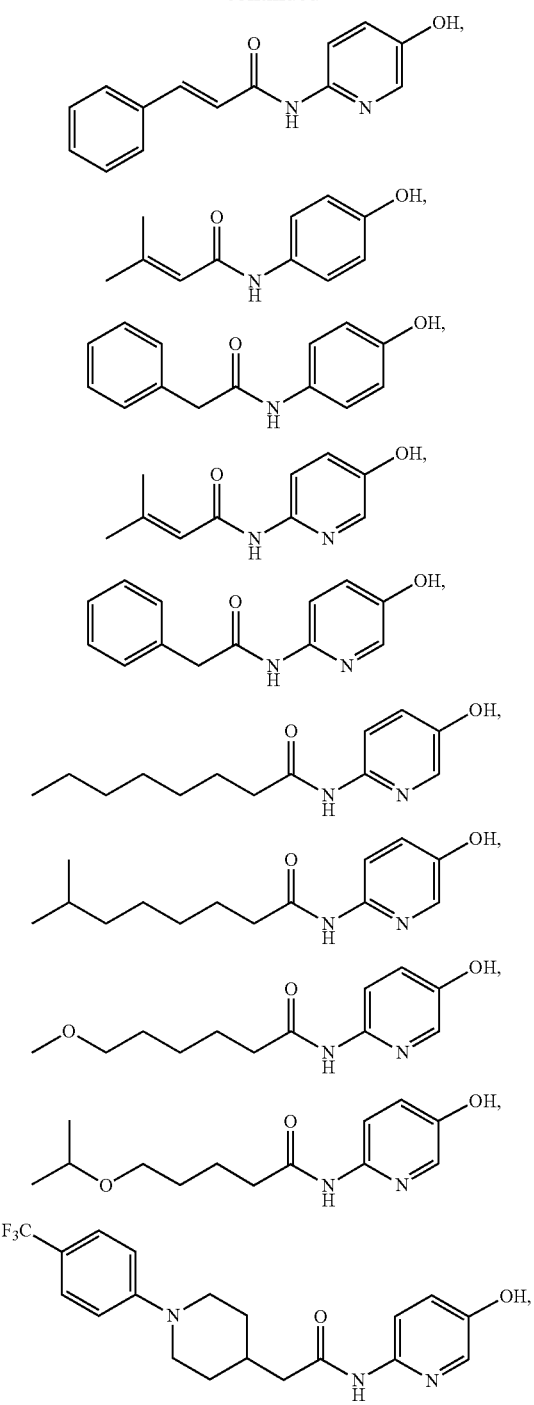

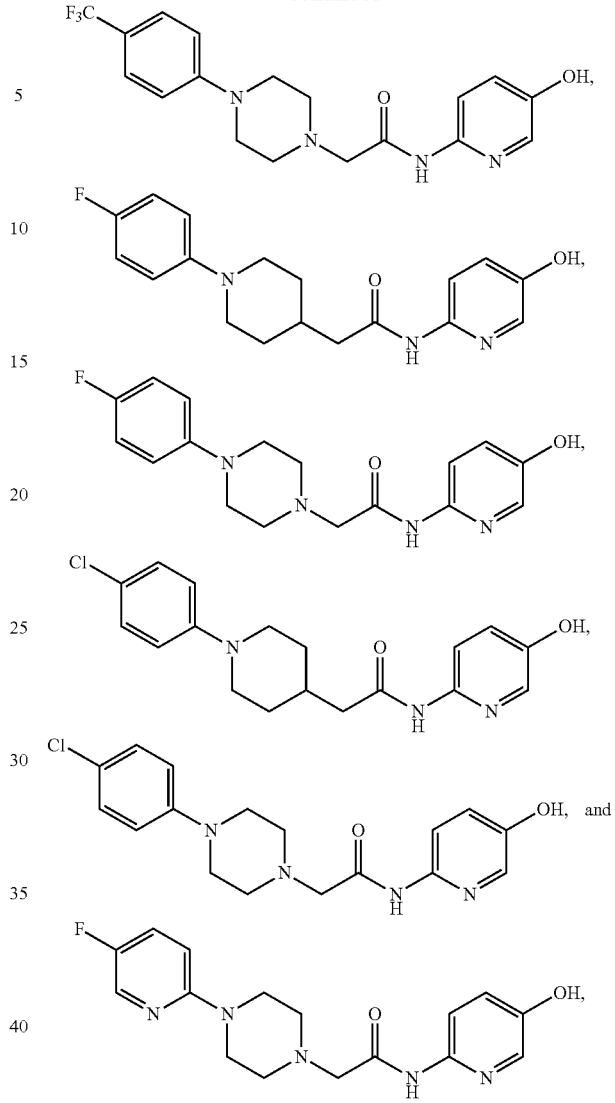

or a salt thereof.

40. The method as recited in claim 1, wherein the compound is contacted with a human.

41. The method as recited in claim 40, wherein the human has a Des1-mediated disorder.

42. The method as recited in claim 41, wherein the Des1-mediated disorder is a metabolic disorder, a lipid storage disorder, an autoimmune or chronic inflammatory disease, a cardiovascular disease, ischemia/reperfusion injury, fibrosis or a related disease, or cancer.

* * * * *

UNITED STATES PATENT AND TRADEMARK OFFICE
CERTIFICATE OF CORRECTION

PATENT NO. : 11,771,684 B2
APPLICATION NO. : 17/477953
DATED : October 3, 2023
INVENTOR(S) : Donna L. Romero et al.

Page 1 of 6

It is certified that error appears in the above-identified patent and that said Letters Patent is hereby corrected as shown below:

In the Specification

In Column 1, Line 9, delete "US2017/066172," and insert -- PCT/US2017/066172, --.

In Column 1, Line 35, delete "sphinogoid" and insert -- sphingoid --.

In Column 6, Line 8, delete "groups;" and insert -- groups. --.

In Column 7, Lines 61-67, delete " " and insert -- --.
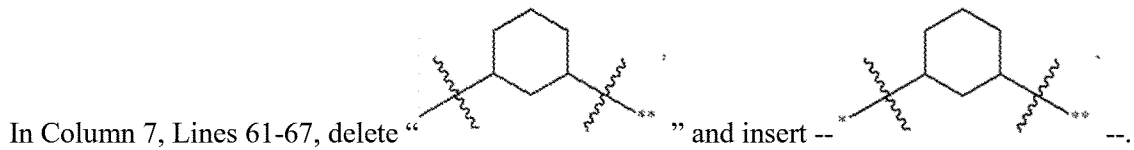

In Column 8, Lines 2-6, delete " " and insert -- --.
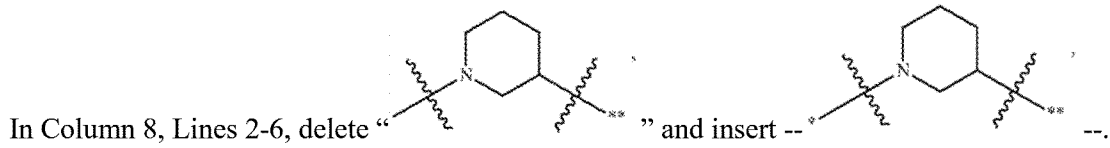

In Column 8, Lines 2-6, delete " " and insert -- --.
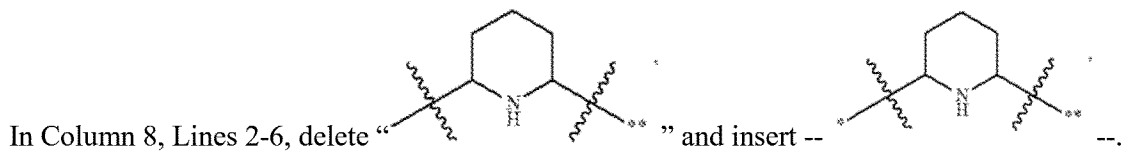

In Column 8, Lines 8-11, delete " " and insert -- --.
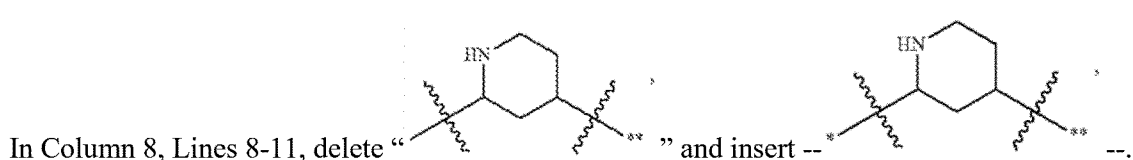

Signed and Sealed this
Thirtieth Day of January, 2024

*Katherine Kelly Vidal*

Katherine Kelly Vidal
*Director of the United States Patent and Trademark Office*

In Column 8, Lines 8-11, delete "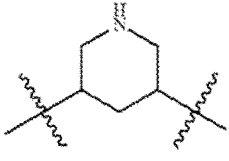" and insert -- 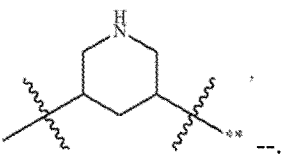 --.

In Column 8, Lines 13-16, delete "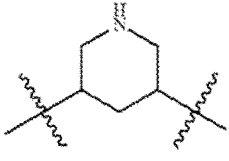" and insert -- 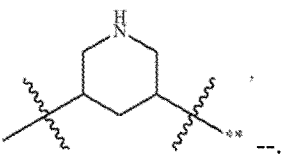 --.

In Column 8, Lines 13-16, delete "" and insert --  --.

In Column 8, Lines 18-21, delete "" and insert --  --.

In Column 8, Lines 18-21, delete "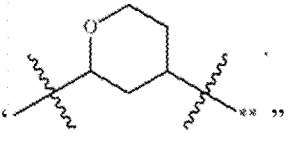" and insert -- 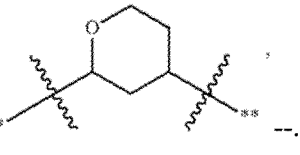 --.

In Column 8, Lines 23-27, delete "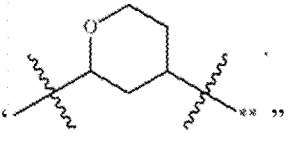" and insert -- 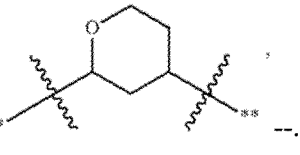 --.

In Column 8, Lines 23-27, delete "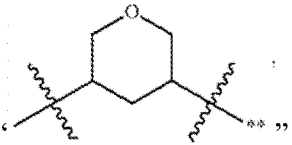" and insert -- 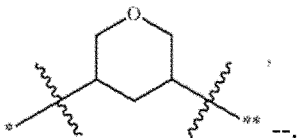 --.

In Column 11, Line 35, delete "fornyl," and insert -- formyl, --.

In Column 11, Line 43, delete "ethenylene" and insert -- ethylene --.

In Column 14, Line 12, delete "tetrahydronapthyl," and insert -- tetrahydronaphthyl, --.

In Column 15, Line 38, delete "benzimnidazolyl," and insert -- benzimidazolyl, --.

In Column 15, Line 42, delete "chromonyl," and insert -- chromyl, --.

CERTIFICATE OF CORRECTION (continued)
U.S. Pat. No. 11,771,684 B2

In Column 15, Line 62, delete "3,5-isomers)." and insert -- 3,5- isomers). --.

In Column 16, Line 23, delete "dihy-dropyridinyl," and insert -- dihydropyridinyl, --.

In Column 18, Line 8, delete "trimethysilyl," and insert -- trimethylsilyl, --.

In Column 20, Line 18, delete "M;" and insert -- μM; --.

In Column 22, Line 3, delete "3-phenylproprionate," and insert -- 3-phenylpropionate, --.

In Column 29, Line 13, delete "edavarone." and insert -- edaravone. --.

In Column 30, Line 18, delete "perinodopril," and insert -- perindopril, --.

In Column 30, Line 21, delete "terteo-thiorphan," and insert -- tardeo-thiorphan, --.

In Column 30, Line 25, delete "tehnisartan" and insert -- telmisartan --.

In Column 30, Line 27, delete "quadrature." and insert -- .quadrature. --.

In Column 30, Line 39, delete "anastrazole, fadrazole," and insert -- anastrozole, fadrozole, --.

In Column 30, Line 46, delete "meturedopa," and insert -- meturedepa, --.

In Column 30, Line 46, delete "uredopa;" and insert -- uredepa; --.

In Column 30, Line 47, delete "methylamelamines" and insert -- methylmelamines --.

In Column 30, Line 53, delete "phenesterine," and insert -- phentermine, --.

In Column 30, Line 56, delete "aclacinomysins," and insert -- aclacinomycins, --.

In Column 30, Line 56, delete "authramycin," and insert -- azithromycin, --.

In Column 30, Line 58, delete "caminomycin," and insert -- carminomycin, --.

In Column 30, Line 59, delete "detorubicin," and insert -- doxorubicin, --.

In Column 31, Line 7, delete "frolinic" and insert -- folinic --.

In Column 31, Line 13, delete "podophyllinic" and insert -- podophyllin --.

In Column 31, Line 19, delete "gemeitabine;" and insert -- gemcitabine; --.

In Column 31, Line 26, delete "(DMFO);" and insert -- (DFMO); --.

CERTIFICATE OF CORRECTION (continued)
U.S. Pat. No. 11,771,684 B2

In Column 32, Line 9, after "consisting" insert -- of --.

In Column 32, Line 23, delete "benzotropine," and insert -- benztropine, --.

In Column 36, Line 65, delete "A: Water" and insert -- A:Water --.

In Column 38, Line 45, delete "EtOAc" and insert -- EtOAc: --.

In Columns 39-40, Line 26, delete "phcnyl)-" and insert -- phenyl)- --.

In Columns 43-44, Line 5, delete "napthamide" and insert -- naphthamide --.

In Columns 43-44, Line 52, delete "napthamide" and insert -- naphthamide --.

In Columns 47-48, Line 58, delete "(m,3H)." and insert -- (m, 3H). --.

In Columns 47-48, Line 61, delete "d6)5" and insert -- d6) δ --.

In Columns 49-50, Line 30, delete "(m,3H)," and insert -- (m, 3H), --.

In Columns 51-52, Line 13, delete "yI)-" and insert -- yl)- --.

In Columns 51-52, Line 35, delete "5" and insert -- δ --.

In Column 54, Line 44, delete "[l-" and insert -- [1- --.

In Column 55, Line 12, delete "butyldinethylsilyl)" and insert -- butyldimethylsilyl) --.

In Column 55, Lines 47-48, delete "yl] acetamide" and insert -- yl]acetamide --.

In Column 56, Line 37, delete "ethyl" and insert -- Ethyl --.

In Column 56, Line 43, delete "n/z):" and insert -- m/z): --.

In Column 58, Line 3, delete "n/z):" and insert -- m/z): --.

In Column 59, Line 6, delete "Ml/" and insert -- mL/ --.

In Column 61, Line 52, delete "r." and insert -- rt. --.

In Column 62, Line 16, delete "ml)" and insert -- mL) --.

In Column 65, Line 1, delete "[i-" and insert -- [1- --.

In Column 65, Line 60, delete "butyldinethylsilyl)" and insert -- butyldimethylsilyl) --.

CERTIFICATE OF CORRECTION (continued)
U.S. Pat. No. 11,771,684 B2

In Column 66, Line 24, delete "[i-" and insert -- [1- --.

In Column 67, Line 52, delete "n/z):" and insert -- m/z): --.

In Column 70, Line 15, delete "stp" and insert -- step --.

In Column 70, Line 44, delete "oxy] pyridin" and insert -- oxy]pyridin --.

In Column 70, Line 56, delete "n/z):" and insert -- m/z): --.

In Column 72, Line 45, delete "ere" and insert -- are --.

In Column 78, Line 50, delete "[l-" and insert -- [1- --.

In Column 79, Line 10, delete "yl) acetamide" and insert -- yl)acetamide --.

In Column 79, Line 54, delete "[I-" and insert -- [1- --.

In Column 80, Line 20, delete "[l-" and insert -- [1- --.

In Column 80, Line 26, delete "HCL." and insert -- HCl. --.

In Column 81, Line 6, delete "butyldimethylsilyl) oxy]" and insert -- butyldimethylsilyl)oxy] --.

In Column 81, Line 50, delete "[l-" and insert -- [1- --.

In Column 81, Line 51, delete "yl) acetamide" and insert -- yl)acetamide --.

In Column 84, Line 21, delete "ml)" and insert -- mL) --.

In Column 93, Line 15, delete "Myolube" and insert -- Myotube --.

In Column 95, Line 15, delete "17θ" and insert -- 17β --.

In Column 96, Line 53, delete "(PLP" and insert -- (PLP) --.

In Column 97, Line 43, delete "and or" and insert -- and/or --.

In Column 98, Line 27, delete "edavarone." and insert -- edaravone. --.

In Column 98, Line 36, delete "ASAHI" and insert -- ASAH1 --.

In Column 98, Line 37, delete "ASAHI" and insert -- ASAH1 --.

CERTIFICATE OF CORRECTION (continued)
U.S. Pat. No. 11,771,684 B2

In the Claims

In Column 99, Line 17, in Claim 1, delete "$R_{1b}$" and insert -- $R_{1b}$, --.

In Column 99, Line 32, in Claim 1, delete "—$CHR_4$—,—$CHR_4CHR_4$—," and insert -- —$CHR_4$—, —$CHR_4CHR_4$—, --.